(12) United States Patent
Cady et al.

(10) Patent No.: US 11,441,167 B2
(45) Date of Patent: Sep. 13, 2022

(54) COMPOSITIONS AND METHODS FOR RAPID IDENTIFICATION AND PHENOTYPIC ANTIMICROBIAL SUSCEPTIBILITY TESTING OF BACTERIA AND FUNGI

(71) Applicant: Roche Molecular Systems, Inc., Pleasanton, CA (US)

(72) Inventors: Kyle C. Cady, Santa Clara, CA (US); Brett Hanson, Milpitas, CA (US); Paulino Abdon, Los Gatos, CA (US); Ryan Chan, San Jose, CA (US); Patrick Lin, San Jose, CA (US); Rochak Mehta, Fremont, CA (US); Troy Rabang, Campbell, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 16/950,160

(22) Filed: Nov. 17, 2020

(65) Prior Publication Data
US 2021/0147898 A1     May 20, 2021

Related U.S. Application Data

(60) Provisional application No. 62/938,144, filed on Nov. 20, 2019.

(51) Int. Cl.
| | |
|---|---|
| *C12P 19/34* | (2006.01) |
| *C12Q 1/18* | (2006.01) |
| *C12Q 1/689* | (2018.01) |
| *C12Q 1/6895* | (2018.01) |
| *C12Q 1/6897* | (2018.01) |
| *C12Q 1/6851* | (2018.01) |
| *C12Q 1/686* | (2018.01) |

(52) U.S. Cl.
CPC .......... *C12Q 1/18* (2013.01); *C12Q 1/689* (2013.01); *C12Q 1/6895* (2013.01); *C12Q 1/6897* (2013.01); *C12Q 1/686* (2013.01); *C12Q 1/6851* (2013.01); *C12Q 2561/101* (2013.01); *C12Q 2561/113* (2013.01); *C12Q 2565/1015* (2013.01); *C12Q 2600/136* (2013.01)

(58) Field of Classification Search
CPC .. C12Q 1/18; C12Q 2561/113; C12Q 1/6851; C12Q 1/686
See application file for complete search history.

(56) References Cited

U.S. PATENT DOCUMENTS

| | | |
|---|---|---|
| 7,763,426 B2 | 7/2010 | Haake et al. |
| 9,970,063 B2 | 5/2018 | Chattopdhyay |
| 10,233,483 B2 | 3/2019 | Talebpour et al. |
| 10,655,188 B2 | 5/2020 | Jarvius et al. |
| 2007/0196818 A1 | 8/2007 | O'Hara |
| 2009/0136953 A1 | 5/2009 | Gold et al. |
| 2011/0200984 A1 | 8/2011 | O'Hara |
| 2012/0100528 A1* | 4/2012 | Jenkins .................. C12Q 1/708 435/5 |
| 2013/0230860 A1* | 9/2013 | Park ........................ B03C 1/288 435/6.12 |
| 2017/0321257 A1 | 11/2017 | Andini et al. |
| 2018/0187237 A1 | 7/2018 | Belenky |
| 2019/0032104 A1 | 1/2019 | Lowery, Jr. et al. |
| 2019/0127778 A1 | 5/2019 | LaBaer et al. |
| 2020/0010874 A1 | 1/2020 | Wang et al. |
| 2020/0024663 A1 | 1/2020 | Nakamura et al. |
| 2020/0263224 A1 | 8/2020 | Churchill et al. |

FOREIGN PATENT DOCUMENTS

| | | |
|---|---|---|
| WO | 2003035905 A2 | 5/2003 |
| WO | 2005042778 A1 | 5/2005 |
| WO | 2015000079 A1 | 1/2015 |
| WO | 2018165080 A1 | 9/2018 |
| WO | 2019036715 A1 | 2/2019 |
| WO | 2019075264 A1 | 4/2019 |
| WO | 2019217333 A1 | 11/2019 |

OTHER PUBLICATIONS

Andini, N. et al., "A 'Culture' Shift: Broad Bacterial Detection, Identification, and Antimicrobial Susceptibility Testing Directly from Whole Blood", Clinical Chemistry 64:10 1453-1462 (2018).
Athamanolap, P. et al., "Machine Learning-Assisted Digital PCR and Melt Enables Broad Bacteria Identification and Pheno-Molecular Antimicrobial Susceptibility Test", BioRxiv preprint online Mar. 24, 2019; doi: http://dx.doi.org/10.1101/587543.
Beuving, J. et al., "Antibiotic Susceptibility Testing of Grown Blood Cultures by Combining Culture and Real-Time Polymerase Chain Reaction Is Rapid and Effective", PLOS ONE vol. 6, Issue 12, e27689 (2011).
Beuving, J. et al., "Impact of same-day antibiotic susceptibility testing on time to appropriate antibiotic treatment of patients with bacteraemia: a randomised controlled trial", Eur J Clin Microbiol Infect Dis, 34:831-838 (2015).
Blaschke, A.J. et al., "Rapid Identification of Pathogens from Positive Blood Cultures by Multiplex PCR using the FilmArray System", Diagn Microbiol Infect Dis. December ; 74(4): 349-355 (2012).
Chen, L. et al., "Direct-qPCR Assay for Coupled Identification and Antimicrobial Susceptibility Testing of Neisseria gonorrhoeae", ACS Infect Dis Sep. 14; 4(9): 1377-1384 (2018).

(Continued)

*Primary Examiner* — Kenneth R Horlick
(74) *Attorney, Agent, or Firm* — David J. Chang

(57) ABSTRACT

The present invention relates to compositions and methods for the use of polymerase chain reaction (PCR) as a reporter assay for rapid and simultaneous bacterial identification and phenotype testing for antimicrobial susceptibility (AST). The current invention uses a strategy that has shown the ability for multiplexing and for handling polymicrobial samples for antimicrobial susceptibility testing.

5 Claims, 62 Drawing Sheets

Specification includes a Sequence Listing.

(56) References Cited

OTHER PUBLICATIONS

Choi, H.J. et al., "Improved PCR for identification of Pseudomonas aeruginosa", Appl Microbiol Biotechnol 97:3643-3651 (2013).

Humphries, H.M. et al., "Understanding and Addressing CLSI Breakpoint Revisions: a Primer for Clinical Laboratories" Journal of Clinical Microbiology, vol. 57 Issue 6 e00203-19 (2019).

Luo, J. et al., "Parallel susceptibility testing of bacteria through culture-quantitative PCR in 96-well plates", International Journal of Infectious Diseases 70 86-92( 2018).

Maxson, T. et al., "Rapid antibiotic susceptibility testing from blood culture bottles with species agnostic real-time polymerase chain reaction", PLOS ONE, https://doi.org/10.1371/journal.pone.0209042 Dec. 13, 2018.

McConnell, M.J. et al., "Quantitative Real-Time PCR for Detection of Acinetobacter baumannii Colonization in the Hospital Environment", Journal of Clinical Microbiology, vol. 50 No. 4, 1412-1414 (2012).

Mezger, A. et al., "A General Method for Rapid Determination of Antibiotic Susceptibility and Species in Bacterial Infections", Journal of Clinical Microbiology, vol. 53 No. 2 425-432 (2015).

Rolain, J.M. et al., "Real-time PCR for universal antibiotic susceptibility testing", Journal of Antimicrobial Chemotherapy 54, 538-541 (2004).

Royo-Cebreco, C. et al., "Afresh look at polymicrobial bloodstream infection in cancer patients", PLOS ONE | https://doi.org/10.1371/journal.pone.0185768 Oct. 24, 2017.

Takahashi, H. et al.,"Development of quantitative real-time PCR for detection and enumeration of Enterobacteriaceae", International Journal of Food Microbiology, 246 92-97 (2017).

Turnridge, J. et al., "Setting and Revising Antibacterial Susceptibility Breakpoints", Clinical Microbiology Reviews, vol. 20, No. 3, 391-408 (2007).

Velez, D.O. et al., "Massively parallel digital high resolution melt for rapid and absolutely quantitative sequence profiling", Nature Scientific Reports, 7:42326 DOI: 10.1038/srep42326 (2017).

Zhang, W. et al., "Quick identification and quantification of Proteus mirabilis by polymerase chain reaction (PCR) assays", Ann Microbiol 63:683-689 (2013).

Zhang, Y. et al., "A 'culture' shift: Application of molecular techniques for diagnosing polymicrobial infections", Biotechnology Advances 37 476-490 (2019).

Shin, DJ et al., "Emerging Analytical Techniques for Rapid Pathogen Identification and Susceptibility Testing", Annu. Rev. Anal. Chem. (2019),12:41-67.

Giacobbe, DR et al., "Rapid microbiological tests for bloodstream infections due to multidrug resistant Gram-negative bacteria: therapeutic implications", Clinical Microbiology and Infection (2020), 26:713-722.

Harris, M and Fasolino, T, "New and emerging technologies for the diagnosis of urinary tract infections", J Lab Med (2022), 46(1): 3-15.

Athamanolap, P. et al., "Nanoarray Digital Polymerase Chain Reaction with High-Resolution Melt for Enabling Broad Bacteria Identification and Pheno-Molecular Antimicrobial Susceptibility Test", Anal. Chem. (2019), 91:12784-12792.

\* cited by examiner

FIG. 30-1

| Antimicrobial | Class | Enterobacterales Sens. < \| Int. \| Res. > | P. aeruginosa Sens. < \| Int. \| Res. > | Acinetobacter spp. Sens. < \| Int. \| Res. > | S. maltophilia Sens. < \| Int. \| Res. > |
|---|---|---|---|---|---|
| Ertapenem | Carbapenem | 0.5 \| 1 \| 2 | -- \| -- \| -- | -- \| -- \| -- | -- \| -- \| -- |
| Meropenem | Carbapenem | 1 \| 2 \| 4 | 2 \| 4 \| 8 | 2 \| 4 \| 8 | -- \| -- \| -- |
| Imipenem | Carbapenem | 1 \| 2 \| 4 | 2 \| 4 \| 8 | 2 \| 4 \| 8 | -- \| -- \| -- |
| Amoxocillin/ Clavulanate | Beta-lactam Combination | 8/4 \| 16/8 \| 32/16 | -- \| -- \| -- | -- \| -- \| -- | -- \| -- \| -- |
| Ceftazidime/ Avibactam | Beta-lactam Combination | 8/4 \| -- \| 16/4 | 8/4 \| -- \| 16/4 | -- \| -- \| -- | -- \| -- \| -- |
| Ceftolozane/ Tazobactam | Beta-lactam Combination | 2/4 \| 4/4 \| 8/4 | 4/4 \| 8/4 \| 16/4 | -- \| -- \| -- | -- \| -- \| -- |
| Ampicillin/ Sulbactam | Beta-lactam Combination | 8/4 \| 16/8 \| 32/16 | -- \| -- \| -- | 8/4 \| 16/8 \| 32/16 | -- \| -- \| -- |
| Piperacillin/ Tazobactam | Beta-lactam Combination | 16/4 \| 32/4-64/4 \| 128/4 | 16/4 \| 32/4-64/4 \| 128/4 | 16/4 \| 32/4-64/4 \| 128/4 | -- \| -- \| -- |
| Aztreonam | Monobactam | 4 \| 8 \| 16 | 8 \| 16 \| 32 | -- \| -- \| -- | -- \| -- \| -- |
| Ampicillin | Beta-lactam | 8 \| 16 \| 32 | -- \| -- \| -- | -- \| -- \| -- | -- \| -- \| -- |
| Cefazolin | Cephalosporin | 2 \| 4 \| 8 | -- \| -- \| -- | -- \| -- \| -- | -- \| -- \| -- |
| Cefepime | Cephalosporin | 2 \| 4-8 \| 16 | 8 \| 16 \| 32 | 8 \| 16 \| 32 | -- \| -- \| -- |
| Cefotaxime | Cephalosporin | 1 \| 2 \| 4 | -- \| -- \| -- | 8 \| 16-32 \| 64 | -- \| -- \| -- |
| Ceftazidime | Cephalosporin | 4 \| 8 \| 16 | 8 \| 16 \| 32 | 8 \| 16 \| 32 | 8 \| 16 \| 32 |

| | | | | |
|---|---|---|---|---|
| Ceftriaxone | Cephalosporin | 1 \| 2 \| 4 | -- \| -- \| -- | 8 \| 16-32 \| 64 |
| Amikacin | Aminoglycoside | 16 \| 32 \| 64 | 16 \| 32 \| 64 | 16 \| 32 \| 64 |
| Gentamicin | Aminoglycoside | 4 \| 8 \| 16 | 4 \| 8 \| 16 | 4 \| 8 \| 16 |
| Tobramycin | Aminoglycoside | 4 \| 8 \| 16 | 4 \| 8 \| 16 | 4 \| 8 \| 16 |
| Ciprofloxacin | Fluoroquinolone | 0.25 \| 0.5 \| 1 | 0.5 \| 1 \| 2 | 1 \| 2 \| 4 |
| Levofloxacin | Fluoroquinolone | 0.5 \| 1 \| 2 | 1 \| 2 \| 4 | 2 \| 4 \| 8 |
| Trimethoprim/ Sulfamethoxazole | Sulfonamide | 2/38 \| -- \| 4/76 | -- \| -- \| -- | 2/38 \| -- \| 4/76 |
| Fosfomycin | Fosfomycin | 64 \| 128 \| 256 | -- \| -- \| -- | -- \| -- \| -- |
| Cefiderocol | Sideromycin | 4 \| 8 \| 16 | 4 \| 8 \| 16 | 4 \| 8 \| 16 |
| Minocycline | Tetracycline | 4 \| 8 \| 16 | 4 \| 8 \| 16 | 4 \| 8 \| 16 |

FIG. 30-2

| Antimicrobial | Class | S. aureus and lugdunensis Sens \| Int \| Res | S. epidermidis Sens \| Int \| Res | Enterococcus spp. Sens \| Int \| Res | S. pneumoniae Sens \| Int \| Res | Streptococcus β-Hemolytic Sens \| Int \| Res | Viridans Streptococcus Sens \| Int \| Res |
|---|---|---|---|---|---|---|---|
| Vancomycin | Glycopeptide | 2 \| 4-8 \| 16 | 4 \| 8-16 \| 32 | 4 \| 8-16 \| 32 | 1 \| -- \| -- | 1 \| -- \| -- | 1 \| -- \| -- |
| Oxacillin | Beta-lactam | 2 \| -- \| 4 | 0.25 \| -- \| 0.5 | -- \| -- \| -- | -- \| -- \| -- | -- \| -- \| -- | -- \| -- \| -- |
| Ampicillin | Beta-lactam | -- \| -- \| -- | -- \| -- \| -- | 8 \| -- \| 16 | -- \| -- \| -- | 0.25 \| -- \| -- | 0.25 \| 0.5-4 \| 8 |
| Penicillin | Beta-lactam | 0.12 \| -- \| 0.25 | 0.12 \| -- \| 0.25 | 8 \| -- \| 16 | 2 \| 4 \| 8 | 0.12 \| -- \| -- | 0.12 \| 0.25-2 \| 4 |
| Cefoxitin | Cephalosporin | 4 \| -- \| 8 | -- \| -- \| -- | -- \| -- \| -- | -- \| -- \| -- | -- \| -- \| -- | -- \| -- \| -- |
| Cefazolin | Cephalosporin | -- \| -- \| -- | -- \| -- \| -- | -- \| -- \| -- | -- \| -- \| -- | -- \| -- \| -- | -- \| -- \| -- |
| Ceftaroline | Cephalosporin | 1 \| 2-4 \| 8 | 1 \| 2-4 \| 8 | -- \| -- \| -- | 0.5 \| -- \| -- | 0.5 \| -- \| -- | -- \| -- \| -- |
| Ceftriaxone | Cephalosporin | -- \| -- \| -- | -- \| -- \| -- | -- \| -- \| -- | 1 \| 2 \| 4 | 0.5 \| -- \| -- | 1 \| 2 \| 4 |
| Clindamycin | Lincosamide | 0.5 \| 1-2 \| 4 | 0.5 \| 1-2 \| 4 | -- \| -- \| -- | 0.25 \| 0.5 \| 1 | 0.25 \| 0.5 \| 1 | 0.25 \| 0.5 \| 1 |
| Daptomycin | Lipopeptide | 1 \| -- \| -- | 1 \| -- \| -- | E. faecalis 2 \| 4 \| 8 E. faecium 4* \| -- \| 8 | -- \| -- \| -- | 1 \| -- \| -- | 1 \| -- \| -- |
| Linezolid | Oxazolidinone | 4 \| -- \| 8 | 4 \| -- \| 8 | 2 \| 4 \| 8 | 2 \| -- \| -- | 2 \| -- \| -- | 2 \| -- \| -- |
| Gentamicin | Aminoglycoside | 4 \| 8 \| 16 | 4 \| 8 \| 16 | -- \| -- \| -- | -- \| -- \| -- | -- \| -- \| -- | -- \| -- \| -- |
| Levofloxacin | Fluoroquinolone | 1 \| 2 \| 4 | 1 \| 2 \| 4 | 2 \| 4 \| 8 | 2 \| 4 \| 8 | 2 \| 4 \| 8 | 2 \| 4 \| 8 |

FIG. 31

| Antifungal | Class | Candida albicans | | | Candida glabrata | | | Candida krusei | | | Candida tropicalis | | | Candida auris | | |
|---|---|---|---|---|---|---|---|---|---|---|---|---|---|---|---|---|
| | | Sens. | Int. | Res. | Sens. | Int. | Res. | Sens. | Int. | Res. | Sens. | Int. | Res. | Sens. | Int. | Res. |
| Anidulafungin | Echinocandin | 0.25 | 0.5 | 1 | 0.12 | 0.25 | 0.5 | 0.25 | 0.5 | 1 | 0.25 | 0.5 | 1 | -- | -- | -- |
| Caspofungin | Echinocandin | 0.25 | 0.5 | 1 | 0.12 | 0.25 | 0.5 | 0.25 | 0.5 | 1 | 0.25 | 0.5 | 1 | -- | -- | -- |
| Micafungin | Echinocandin | 0.25 | 0.5 | 1 | 0.06 | 0.12 | 0.25 | 0.25 | 0.5 | 1 | 0.25 | 0.5 | 1 | -- | -- | -- |
| Voriconazole | Triazole | 0.12 | 0.25-0.5 | 1 | -- | -- | -- | 0.5 | 1 | 2 | 0.12 | 0.25-0.5 | 1 | -- | -- | -- |
| Fluconazole | Triazole | 2 | 4* | 8 | -- | 32* | 64 | -- | -- | -- | 2 | 4* | 8 | -- | -- | -- |

\* SDD - Susceptible Dose Dependent

FIG. 32

Primers and Probes to Perform Real-Time PCR ID and AST Assay of *Candida* Genus

| Oligonucleotide Type | Oligonucleotide Name | SEQ ID NO: | Sequence | Modifications |
|---|---|---|---|---|
| Forward primers | SEGP1712<br>SEGP1718 | 88<br>91 | CGTTTTCATTAATCAAGAACGAAAGTTA<br>ACAACGGATCTCTTGGTTCTC | |
| Reverse primers | SEGP1713<br>SEGP1719 | 89<br>92 | ACCGATCCCTAGTCGGCATA<br>GCAATGTGCGTTCAAAGATTCGA | |
| Probes | SEGP1716 | 90 | <FAM>AGACTACGA<ZEN>CGGTATCTGATCATCTTCG<br>ATC CC<3IABkFQ> | <FAM>: Fluorophore<br><ZEN>: Quencher<br><3IABkFQ>: 3` Blocker |
| Probes | SEGP1722.1 | 93 | <FAM_Thr>TCGATGAAG<BHQ_2>AACGCAGGCGAAATG<br>CGATACG<Phos> | <FAM_Thr>: Fluorophore<br><BHQ_2>: Quencher<br><Phos>: Phosphate |

FIG. 38

| Primers and Probes that hybridize to *16s rRNA* in bacteria (gram positive and gram negative) | | | |
|---|---|---|---|
| Oligonucleotide Type | Oligonucleotide Name | SEQ ID NO: | Sequence | Modifications |
| Forward primer | SEGP1830 | 94 | TCCTACGGGAGGCAGCAGT | |
| Reverse primer | SEGP1831 | 95 | GGACTACCAGGGTATCTAATCCTGTT | |
| Probe | SEGP1895.1 | 96 | \<CFR_635\>CGTATTACCGCGGCT\<BHQ_2\>GCTGGCAC\<Phos\> | \<CFR_635\>: Fluorophore \<BHQ_2\>: Quencher \<Phos\>: Phosphate |

FIG. 39

| Gram-Negative Bacterial Groups | Channel | Wavelength | Dye |
|---|---|---|---|
| Acinetobacter | 1 | 435-470 | ATTO425/Coumarin |
| P. aeruginosa | 2 | 495-521 | FAM |
| Enterobacterales | 3 | 540-580 | HEX |
| Bacterial 16S | 4 | 610-645 | CFR635/JA270 |
| Generic Internal Control | 5 | 680-700 | Cy5.5 |

FIG. 40B

| Gram (+) Bacterial Groups | Channel | Wavelength | Dye |
|---|---|---|---|
| Streptococcus | 1 | 435-470 | ATTO425/Coumarin |
| Staphylococcus | 2 | 495-521 | FAM |
| Enterococcus | 3 | 540-580 | HEX |
| Bacterial 16S | 4 | 610-645 | CFR635/JA270 |
| Generic Internal Control | 5 | 680-700 | Cy5.5 |

FIG. 41B

Ciprofloxacin

A)

| Species | Resistant | Susceptible |
|---|---|---|
| Abi | 51 | 35 |
| Ecl | 57 | 8 |
| Eco | 74 | 16 |
| Kae | 25 | 58 |
| Kpn | 85 | 13 |
| Pae | 31 | 48 |

B)

| Species | Sensitivity | Specificity | Categorical Agreement |
|---|---|---|---|
| Abi | 96% | 100% | 98% |
| Ecl | 96% | 100% | 97% |
| Eco | 100% | 94% | 99% |
| Kae | 96% | 97% | 96% |
| Kpn | 100% | 100% | 100% |
| Pae | 94% | 100% | 97% |

FIG. 43

Gentamicin

A)

| Species | Resistant | Susceptible |
|---------|-----------|-------------|
| Abi | 26 | 59 |
| Ecl | 38 | 26 |
| Eco | 45 | 47 |
| Kae | 8 | 75 |
| Kpn | 52 | 41 |
| Pae | 12 | 73 |

B)

| Species | Sensitivity | Specificity | Categorical Agreement |
|---------|-------------|-------------|----------------------|
| Abi | 100% | 100% | 100% |
| Ecl | 89% | 100% | 94% |
| Eco | 98% | 98% | 98% |
| Kae | 75% | 97% | 95% |
| Kpn | 94% | 100% | 97% |
| Pae | 92% | 100% | 99% |

Meropenem

A)

| Species | Resistant | Susceptible |
|---|---|---|
| Abi | 45 | 31 |
| Ecl | 53 | 8 |
| Eco | 76 | 13 |
| Kae | 23 | 57 |
| Kpn | 86 | 12 |
| Pae | 54 | 19 |

B)

| Species | Sensitivity | Specificity | Categorical Agreement |
|---|---|---|---|
| Abi | 98% | 87% | 93% |
| Ecl | 81% | 100% | 84% |
| Eco | 87% | 92% | 88% |
| Kae | 78% | 95% | 90% |
| Kpn | 95% | 83% | 94% |
| Pae | 91% | 89% | 90% |

FIG. 47

| Organism | Strain ID | Source | Source ID | Known Resistance Mechanism | Gene Target | | | |
|---|---|---|---|---|---|---|---|---|
| | | | | | blaKPC | blaVIM | blaNDM | blaOXA-48 |
| Klebsiella pneumoniae | 16248 | CDC | AR-0005 | KPC-2 | Pos | Neg | Neg | Neg |
| Enterobacter cloacae | 16313 | CDC | AR-0093 | KPC-6 | Pos | Neg | Neg | Neg |
| Pseudomonas aeruginosa | 17210 | CDC | AR-0100 | VIM-2 | Neg | Pos | Neg | Neg |
| Klebsiella pneumoniae | 16235 | CDC | AR-0040 | VIM-27 | Neg | Pos | Neg | Neg |
| Acinetobacter baumannii | 17398 | CDC | AR-0037 | NDM-1 | Neg | Neg | Pos | Neg |
| Escherichia coli | 16215 | CDC | AR-0055 | NDM-1 | Neg | Neg | Pos | Neg |
| Klebsiella pneumoniae | 16266 | CDC | AR-0160 | OXA-48 | Neg | Neg | Neg | Pos |
| Klebsiella aerogenes | 17413 | CDC | AR-0074 | OXA-48 | Neg | Neg | Neg | Pos |

FIG. 54

COMPOSITIONS AND METHODS FOR RAPID IDENTIFICATION AND PHENOTYPIC ANTIMICROBIAL SUSCEPTIBILITY TESTING OF BACTERIA AND FUNGI

CROSS REFERENCE TO RELATED APPLICATIONS

This application claims the benefit of priority to U.S. Provisional Application No. 62/938,144 filed on Nov. 20, 2019, which is hereby incorporated in its entirety by reference.

REFERENCE TO SEQUENCE LISTING

This application contains a Sequence Listing submitted as an electronic text file named "35710_US1_Sequence_Listing.txt", having a size in bytes of 36 kb, and created on Nov. 12, 2020.

FIELD OF THE INVENTION

The present disclosure relates to the field of molecular diagnostics, and more particularly to the identification and the determination of antimicrobial susceptibility of bacteria from biological samples.

BACKGROUND OF THE INVENTION

There is an urgent need for the development or rapid and convenient methods for the detection, identification and determination of antimicrobial susceptibility of bacterial pathogens in clinical samples to guide the diagnosis and treatment of infectious disease. A good example for this need is in bloodstream infections (BSI). BSI ranks among the top seven causes of death in North America and Europe with an estimated 1.7 million sepsis events/year in the US contributing to 270,000 deaths/year and $14 billion annual US healthcare costs. A decreased time to directed antimicrobial therapy has been shown to improve morbidity and mortality in septic patients, which then results in decreased length of stay (LOS) and lower hospital costs. Faster susceptibility results will also enable more rapid antimicrobial de-escalation leading to less adverse effects and decreased contribution to drug resistance. Therefore, there remains a need for the development of an assay and testing system that will provide rapid phenotypic antimicrobial susceptibility results in BSIs enabling clinicians to provide the most appropriate antimicrobial therapies more quickly leading to improved patient outcomes.

Polymicrobial bloodstream infection (BSI), defined as the presence of at least two different microorganisms found from the blood cultures, has been reported increasingly, with rates ranging from 6% to 32% of all BSI episodes. The mortality rate of hospitalized patients with polymicrobial BSIs ranged from 21% to 63%, approximately twice the rate of those with monomicrobial infections.

Traditional Antimicrobial Susceptibility Testing (AST) is performed by growing a given bacteria in the presence of a given antimicrobial—this can be done in both liquid culture and on solid agar media. The two most common methods of AST are: 1) Microbroth Dilution, and 2) Disk Diffusion (aka Kirby-Bauer). The microbroth dilution method provides both quantitative (Minimum Inhibitory Concentration) and qualitative (Susceptible, Intermediate, and Resistant) results. The disk diffusion method provides only qualitative results.

Microbroth dilution is performed by incubating a given bacteria in the presence of multiple concentrations of antimicrobial. Following incubation, growth/no growth of the bacteria is observed at each concentration of antimicrobial. The lowest concentration at which no growth is observed is the Minimum Inhibitory Concentration (MIC), and has units of ug/mL. Established guidelines provide the "breakpoint" where experimentally determined MIC values for specific bacterial groups or species are interpreted as susceptible, intermediate, or resistant (SIR) to the given antimicrobial.

Disk diffusion is performed by creating a "bacterial lawn" of a given bacteria on solid agar media, and then placing a singular antibiotic disk onto the agar media. The antibiotic in the disk diffuses into the media, and following incubation, a circular zone of inhibition around the disk is created. The diameter of the zone along with information on the bacterial species and antimicrobial is used in conjunction with reference established diameter breakpoints to determine whether the pathogen is susceptible, intermediate, or resistant to the given antimicrobial.

In general, the two most commonly used guidelines for interpreting AST results are guidelines from the: 1) Clinical Laboratory Standards Institute (CLSI), and 2) European Committee on Antimicrobial Susceptibility Testing (EUCAST). The US uses the CLSI guidelines while the European countries use the EUCAST guidelines. The current version from CLSI is M100 ED30, while the current version from EUCAST is Version 10.

SUMMARY OF THE INVENTION

The present invention relates to a polymerase chain reaction (PCR)-based rapid identification and antimicrobial susceptibility testing (ID/AST) System that supports an automated workflow for specific assay panels utilizing PCR technology for the rapid and simultaneous identification and determination of antimicrobial susceptibility of bacteria, directly from biological samples, e.g. from positive blood cultures for use in clinical laboratories. This system also has the capability of utilizing and analyzing samples from other sample types such as urine and respiratory infections. The PCR-based rapid ID/AST System uses the functionalities of instrumentation, consumables, reagents, and data management to provide a workflow from sample processing with reagents to result interpretation. By performing a single PCR assay, target identification and antimicrobial susceptibility results are outputs from the system.

The present invention also relates to a PCR-based rapid ID/AST bloodstream infection (BSI) panel that is an in vitro diagnostic test utilizing PCR Technology for the rapid identification of select bacteria or fungi and performing phenotypic antimicrobial susceptibility testing (AST) on the PCR-based rapid ID/AST system. The PCR-based rapid ID/AST BSI assay can be performed directly on positive blood culture samples, on pre-positive blood cultures, or potentially directly from patient serum. This assay is indicated as an aid in diagnosing and identifying antimicrobial susceptibility of specific pathogens that can cause bacteremia. This panel is designed to analyze the most common BSI Gram-negative and Gram-positive pathogens, with the potential for Fungi. The TaqMan 5' nuclease real-time PCR assay configuration coupled with the ID strategy should provide the capability to provide Minimum Inhibitory Concentration (MIC) and Susceptible, Intermediate and Resistant (SIR) information for polymicrobial samples, monomicrobial samples, and isolate testing as needed. These results should be used in conjunction with other clinical and laboratory findings. Standard laboratory protocols for processing positive blood cultures should be followed to ensure availability of isolates for supplemental testing as needed.

The present invention also relates to PCR-based rapid ID/AST phenotypic screening tests that are in vitro diagnostic tests utilizing PCR Technology for the rapid identification and phenotypic susceptibility testing of a target pathogen or group of pathogens for a single drug, class of drugs, or combination of drugs. The PCR-based rapid ID/AST screening assays are performed either directly from clinical samples or from bacterial/fungal isolates. These assays will indicate the presence of problematic drug resistant pathogens to aid in patient and hospital safety. Examples of these types of tests are for Methicillin-Resistant *Staphylococcus aureus* (MRSA), Vancomycin-Resistant *Staphylococcus aureus* (VRSA), Vancomycin-resistant Enterococci (VRE), Carbapenem-Resistant Enterobacteriaceae (CRE), *Candida auris*, and MDR *Neisseria gonorrhoeae*.

Therefore, one aspect of the present invention relates to a method of performing a single quantitative real-time PCR assay as a reporter in the presence of at least one concentration of at least one antimicrobial or antimicrobial class to simultaneously identify and determine the antimicrobial susceptibility of a group of bacteria or fungi that have similar or identical clinical breakpoints for at least one antimicrobial or one antimicrobial class. In one embodiment, the target group of bacteria or fungi are present in bloodstream infections (BSI, gastrointestinal infections or colonization, respiratory infections or colonization, urinary infections or colonization, nasal infections or colonization, rectal infections or colonization, or wound infections. In one embodiment, identification of the group of bacteria or fungi is by detecting a signal that is specific to the group of bacteria or fungi. In one embodiment, the specific signal is detected by using primer and probe oligonucleotides that hybridize more selectively to a target gene that is from the group of bacteria or fungi than to the target gene that is not from the group of bacteria or fungi. In one embodiment, the target gene is selected from rplP, ompA, tuf, rpoB, ddl, ddlA, fdnG sodA, gyrB, O-antigen acetylase, ecfX, tusA, CPE, sip, and nuc.

In another embodiment, the group of bacteria or fungi represents a taxonomic Order.

In one embodiment, the taxonomic Order is the Order Enterobacterales. In another embodiment, the group of bacteria or fungi comprises a taxonomic Family. In one embodiment, the taxonomic Family is selected from Enterobacteriaceae, Yersiniaceae, Morganellaceae, or a combination of said families. In yet another embodiment, the group of bacteria or fungi comprises a taxonomic Genus. In one embodiment, the taxonomic Genus is selected from *Enterococcus, Candida, Pseudomonas, Acinetobacter, Staphylococcus, Stenotrophomonas, Streptococcus*, and *Escherichia, Klebsiella, Enterobacter, Salmonella, Citrobacter, Serratia, Shigella, Corynebacterium, Micrococcus, Bacillus, Haemophilus, Propionibacterium, Bacteroides, Clostridium, Peptostreptococcus, Fusobacterium, Pasteurella, Lactobacillus, Aerococcus, Prevotella, Burkholderia, Moraxella, Vibrio, Listeria, Plesiomonas, Yersinia, Morganella, Providencia*, or *Proteus*.

In another embodiment, the group of bacteria or fungi represents a taxonomic Species. In one embodiment, the taxonomic Species is selected from *Enterococcus faecalis* (Efs), *Enterococcus faecium* (Efm), *Escherichia coli* (Eco), *Klebsiella pneumoniae* (Kpn), *Klebsiella oxytoca* (Kox), *Enterobacter cloacae* (Ecl), *Enterobacter aerogenes* (Kae), *Citrobacter freundii* (Cfi), *Citrobacter koseri* (Cko), *Morganella morganii* (Mmg), *Providencia stuartii* (Pst), *Proteus mirabilis* (Pms), *Proteus vulgaris* (Pvs), *Candida albicans* (Cal), *Candida auris* (Cau), *Pseudomonas aeruginosa* (Pae), *Acinetobacter baumannii* (Abi), *Acinetobacter pittii* (Api), *Acinetobacter nosocomialis* (Ano), *Haemophilus* influenza, *Listeria monocytogenes, Staphylococcus aureus* (Sau), *Staphylococcus lugdunensis, Staphylococcus epidermidis* (Sep), *Stenotrophomonas maltophilia* (Sma), *Streptococcus pneumoniae* (Spn), *Streptococcus agalactiae* (Sag), *Streptococcus pyogenes* (Spy), *Plesiomonas shigelloides, Vibrio parahaemolyticus, Vibrio vulnificus*, or *Vibrio cholerae*.

In yet another embodiment, the method further comprises a step selected from verifying the identification of the group of bacteria or fungi with additional primer and probe oligonucleotides that hybridize more selectively to a second target gene that is from the group of target bacteria or fungi than to the second target gene that is not from the group of bacteria or fungi or determining a mechanism for an antimicrobial susceptibility phenotype or for a toxin or virulence phenotype, or both verifying and determining steps. In another embodiment, the method further comprises simultaneously identifying and determining the antimicrobial susceptibility of more than one groups of bacteria or fungi wherein each group of bacteria or fungi has similar or identical clinical breakpoints for at least one antimicrobial or one antimicrobial classes.

In another aspect, the present invention relates to a method of performing a single quantitative real-time PCR assay as a reporter in the presence of at least one concentration of at least one antimicrobial or antimicrobial class to simultaneously identify and determine the antimicrobial susceptibility of bacteria of the Enterobacterales Order to an antimicrobial or a class of antimicrobials by using primer and probe oligonucleotides that hybridize more selectively to a target gene that is in the Enterobacterales taxonomic Order than to the target gene that is not in the Enterobacterales taxonomic Order. In one embodiment, the target gene is selected from rplP, gyrB, and rpoB. In one embodiment, the primer and probe oligonucleotides that hybridize more selectively to the target gene that is in the Enterobacterales taxonomic Order than to the target gene that is not in the Enterobacterales taxonomic Order comprise the nucleotide sequences comprising SEQ ID NOs: 1-16. In one embodiment, the primer and probe oligonucleotides that hybridize more selectively to gyrB in the Enterobacterales Order than to gyrB in the non-Enterobacterales Order comprise the nucleotide sequences comprising SEQ ID NOs: 8-10.

In another aspect, the present invention relates to a method of performing a single multiplexed quantitative real-time PCR assay as a reporter in the presence of at least one concentration of at least one antimicrobial or antimicrobial class to simultaneously identify and determine the antimicrobial susceptibility of a plurality of bacterial or fungal strains from a biological sample, i.e. from a polymicrobial biological sample. In one embodiment, the biological sample is selected from whole blood, plasma, serum, red blood cell fraction, saliva, cerebrospinal fluid, semen, stool, urine, nasal swab, wound swab, dermal swab, rectal swab, bile, lymph, sputum, lavage fluid, or a combination thereof. In one embodiment, the biological sample is whole blood, plasma, serum or a combination thereof. In one embodiment, the biological sample is cultured prior to performing the PCR assay. In another embodiment, the biological sample is a bacterial or fungal isolate. In another embodiment, the plurality of bacterial or fungal strains are grouped into at least one group of bacteria or fungi that have similar or identical clinical breakpoints for at least one antimicrobial or antimicrobial class. In one embodiment, the plurality of bacterial or fungal strains are grouped into more than one groups of bacteria or fungi wherein each group of bacteria or fungi has similar or identical clinical breakpoints for at least one antimicrobial or one antimicrobial class.

In another embodiment, the identification of the plurality of bacterial strains utilizes a plurality of strain-specific 5' nuclease (TaqMan) oligonucleotide probes, each labeled with fluorescent dyes that have different emission wavelengths. In one embodiment, one or more of the plurality of strain-specific 5' nuclease (TaqMan) oligonucleotide probes comprises probes that utilize the Temperature Assisted Generation of Signal (TAGS) technology. In another embodiment, the method further comprises a step selected from verifying the identification of the plurality of bacterial or fungal strains, or determining a mechanism for an antimicrobial susceptibility phenotype or for a toxin or virulence phenotype, or both verifying and determining steps.

In another aspect, the present invention relates to a method comprising performing a single quantitative real-time PCR assay in the presence of at least one concentration of at least one antimicrobial or class of antimicrobials to simultaneously identify and determine Susceptible, Intermediate and Resistant (SIR) information for a target bacterial or fungal strain or for a target group of bacteria or fungi to the antimicrobial or the class of antimicrobials wherein the identification of the target strain or target group and the determination of SIR information are derived from one or more mathematical relationships associated with PCR data. In one embodiment, the mathematical relationship is selected from Threshold Cycle (Ct), Slope, Inflection of a sigmoid curve fit, Absolute Fluorescence Intensity (AFI), or Endpoint Relative Intensity (ERI). In another embodiment, the mathematical relationship is a relative expression between different antimicrobial concentrations or different antimicrobials and is selected from $\Delta Ct$, $2^{\wedge}(\Delta Ct)$, $\Delta$Inflection, $\Delta$AFI, or $\Delta$ERI. In one embodiment, the mathematical relationship is a combination of mathematical relationships selected from Threshold Cycle (Ct), Slope, Inflection of a sigmoid curve fit, Absolute Fluorescence Intensity (AFI), or Endpoint Relative Intensity (ERI). In yet another embodiment, the mathematical relationship is a combination of relative expressions between different antimicrobial concentrations or different antimicrobials and is selected from $\Delta Ct$, $2^{\wedge}(\Delta Ct)$, $\Delta$Inflection, $\Delta$AFI, or $\Delta$ERI. In another embodiment, the method further comprises a step of selected from verifying the identification of the target bacterial or fungal strains or target group of bacteria or fungi, or determining a mechanism for an antimicrobial susceptibility phenotype or for a toxin or virulence phenotype, or both verifying and determining steps. In another embodiment, the method further comprises identifying and determining the antimicrobial susceptibility of more than one target bacteria or fungi strains or more than one target groups of bacteria or fungi wherein each target strain or target group has similar or identical clinical breakpoints for at least one antimicrobial or one antimicrobial class.

*moniae, S. pyogenes, E. faecium, E. faecalis, S. aureus,* and *S. epidermidis.* Growth curves are observed for all Gram-positive pathogens.

Figure 1:
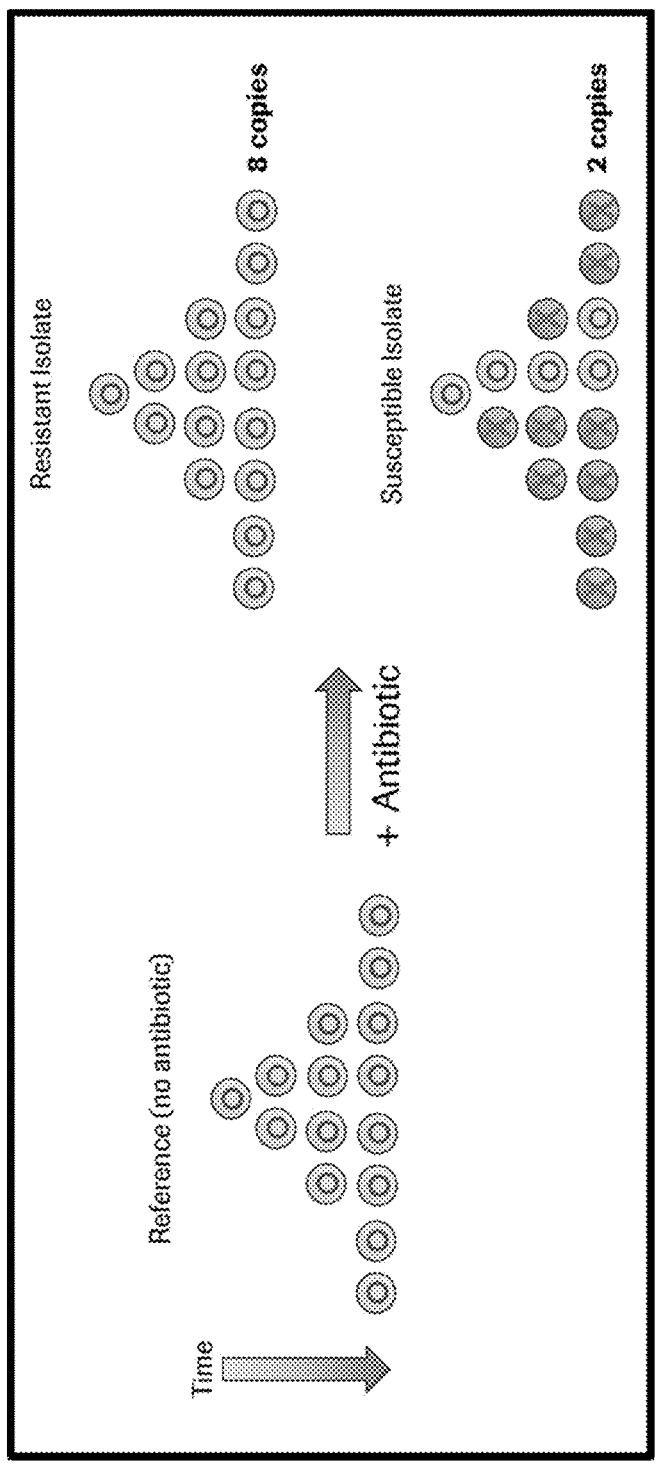
FIG. 1. In the absence of antimicrobial (shown as Reference), bacteria have ongoing genomic DNA replication. In the presence of an antimicrobial, resistant bacteria will replicate with similar number of genome copies as the Reference, while susceptible bacteria will experience inhibition of replication resulting in fewer copies. This difference in growth provides a phenotypic readout that can be determined by qPCR.
Figure 2:
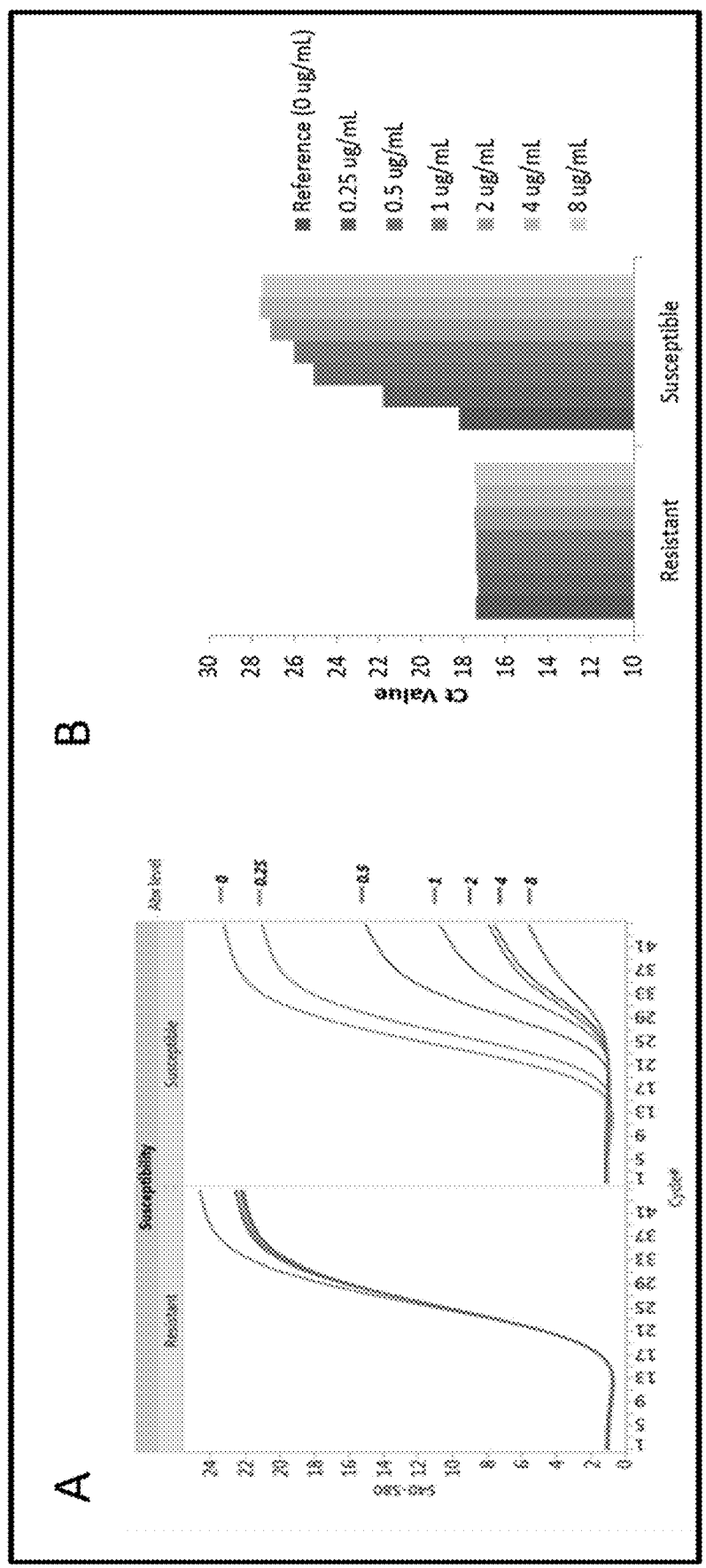
FIG. 2. A The raw qPCR data is depicted as growth curves where fluorescence (e.g. from a TaqMan probe) is measured at each PCR cycle. For the resistant isolate, the growth curve appears similar irrespective of incubation for four hours at different antimicrobial concentrations, whereas in the susceptible isolate, a dose-dependent decrease in fluorescent intensity and increase in the number of cycles required for the signal to cross background (threshold) level, which is commonly referred as the Cycle threshold or Ct value. B The same qPCR data is represented based on the Ct value, where a resistant isolate has little or no change in Ct value as a function of antimicrobial concentration, while a susceptible isolate has a dose dependent increase in Ct value by detecting a smaller number of replicating bacteria.

FIGS. 30-1 and 30-2. Established Minimum Inhibitory Concentration (MIC) breakpoints for Gram-negative bacterial organisms as determined by the Clinical and Laboratory Standards Institute (CLSI) document M100 ED 30. Breakpoints are used to interpret MIC results from Antimicrobial Susceptibility Testing, and to classify "groupings" of organisms as either Susceptible, Intermediate, or Resistant to a given antimicrobial. Groupings of organisms can be at differing levels, including, but not limited to, species, genus, order, or a specific biochemical property.

FIG. 31. Established Minimum Inhibitory Concentration (MIC) breakpoints for Gram-positive bacterial organisms as determined by the Clinical and Laboratory Standards Institute (CLSI) document M100 ED 30. Breakpoints are used to interpret MIC results from Antimicrobial Susceptibility Testing, and to classify "groupings" of organisms as either Susceptible, Intermediate, or Resistant to a given antimicrobial. Groupings of organisms can be at differing levels, including, but not limited to, species, genus, order, or a specific biochemical property.

FIG. 32. Established Minimum Inhibitory Concentration (MIC) breakpoints for fungal organisms (yeast) as determined by the Clinical and Laboratory Standards Institute (CLSI) document M60 ED 1. Breakpoints are used to interpret MIC results from Antifungal Susceptibility Testing (AFST), and to classify "groupings" of organisms as either Susceptible, Intermediate, or Resistant to a given antifungal. Groupings of organisms can be at differing levels, including, but not limited to, species, genus, order, or a specific biochemical property. Of note is that while AFST is recommended for *Candida auris,* neither CLSI or CDC currently have established breakpoints for the species; instead, AFST results from closely related *Candida* spp. and expert opinion are used to determine the susceptibility of *C. auris* isolates to a given antifungal.

Figure 33:
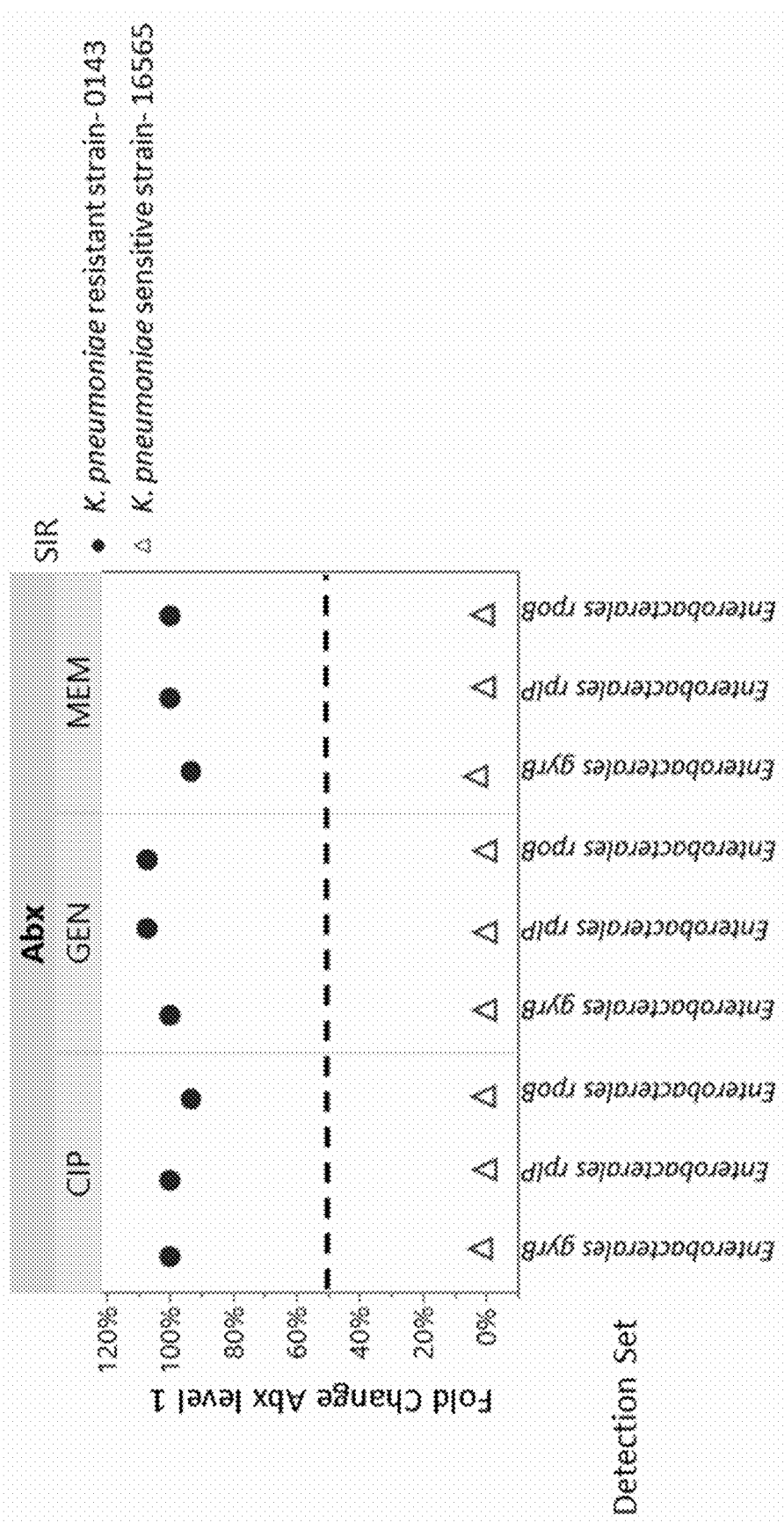

FIG. 33. Rapid Identification and phenotypic antimicrobial susceptibility testing of Enterobacterales utilizing three distinct target genes (gyrB, rplP, and rpoB) and three classes of antibacterial agents: fluoroquinolone (CIP), aminoglycoside (GEN), and carbapenem (MEM).

Figure 34:
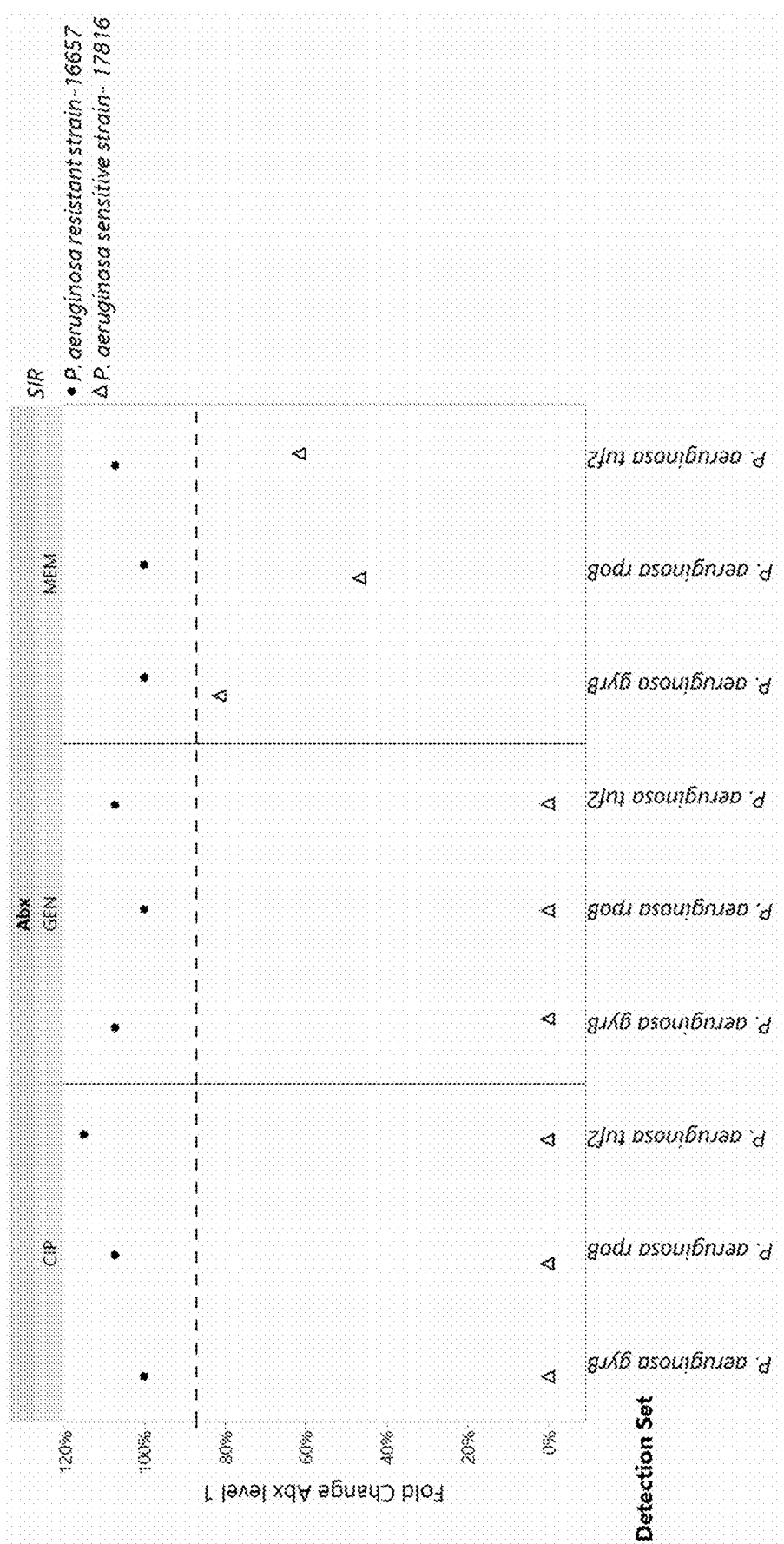

FIG. 34. Rapid Identification and phenotypic antimicrobial susceptibility testing of *P. aeruginosa* utilizing three distinct target genes (tuf, gyrB, rpoB) and three classes of antibacterial agents: fluoroquinolone (CIP), aminoglycoside (GEN), and carbapenem (MEM).

Figure 35:
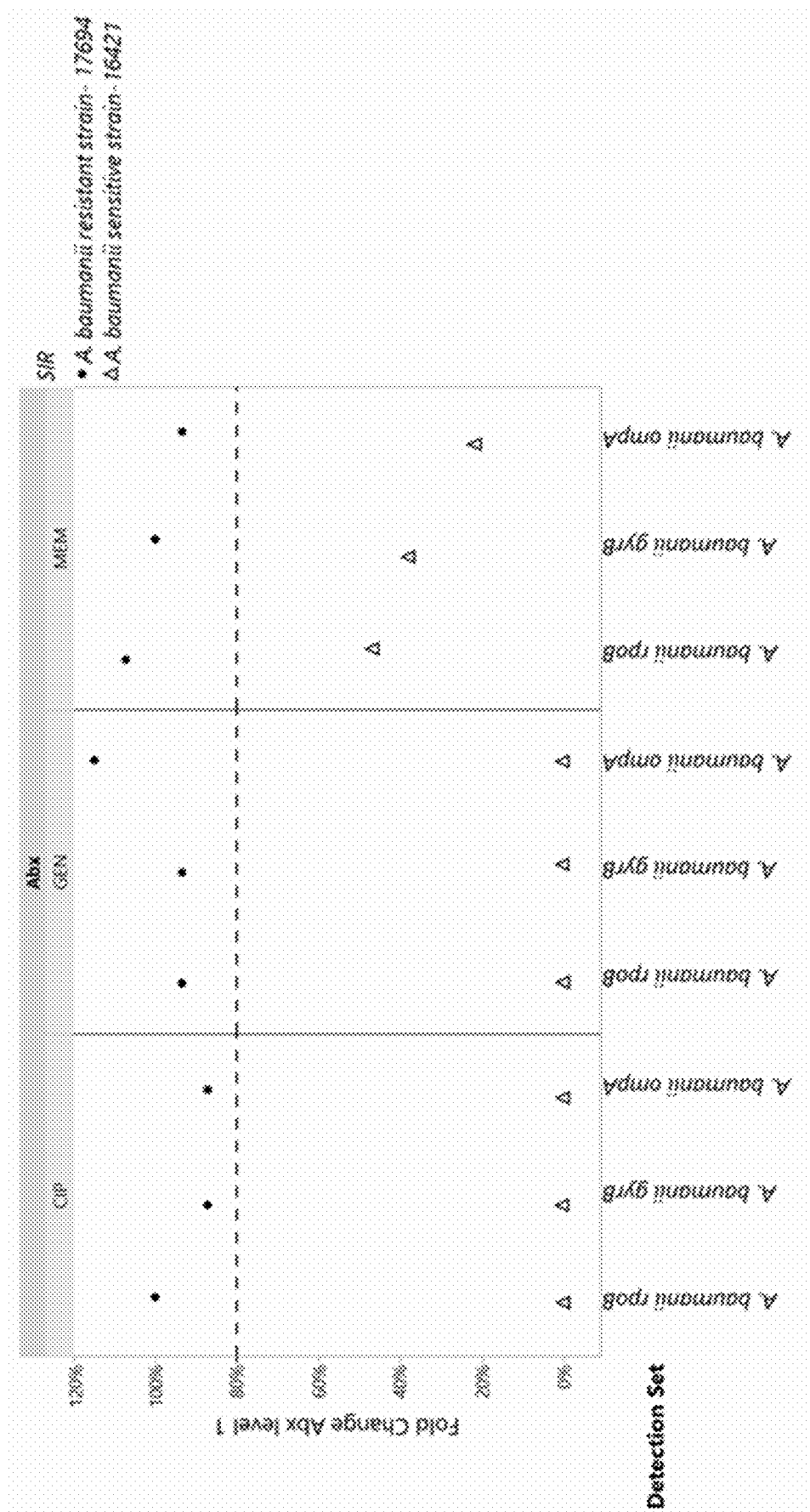

FIG. 35. Rapid Identification and phenotypic antimicrobial susceptibility testing of *Acinetobacter* utilizing three distinct target genes (ompA, rpoB, and gyrB) and three classes of antibacterial agents: fluoroquinolone (CIP), aminoglycoside (GEN), and carbapenem (MEM).

Figure 36:
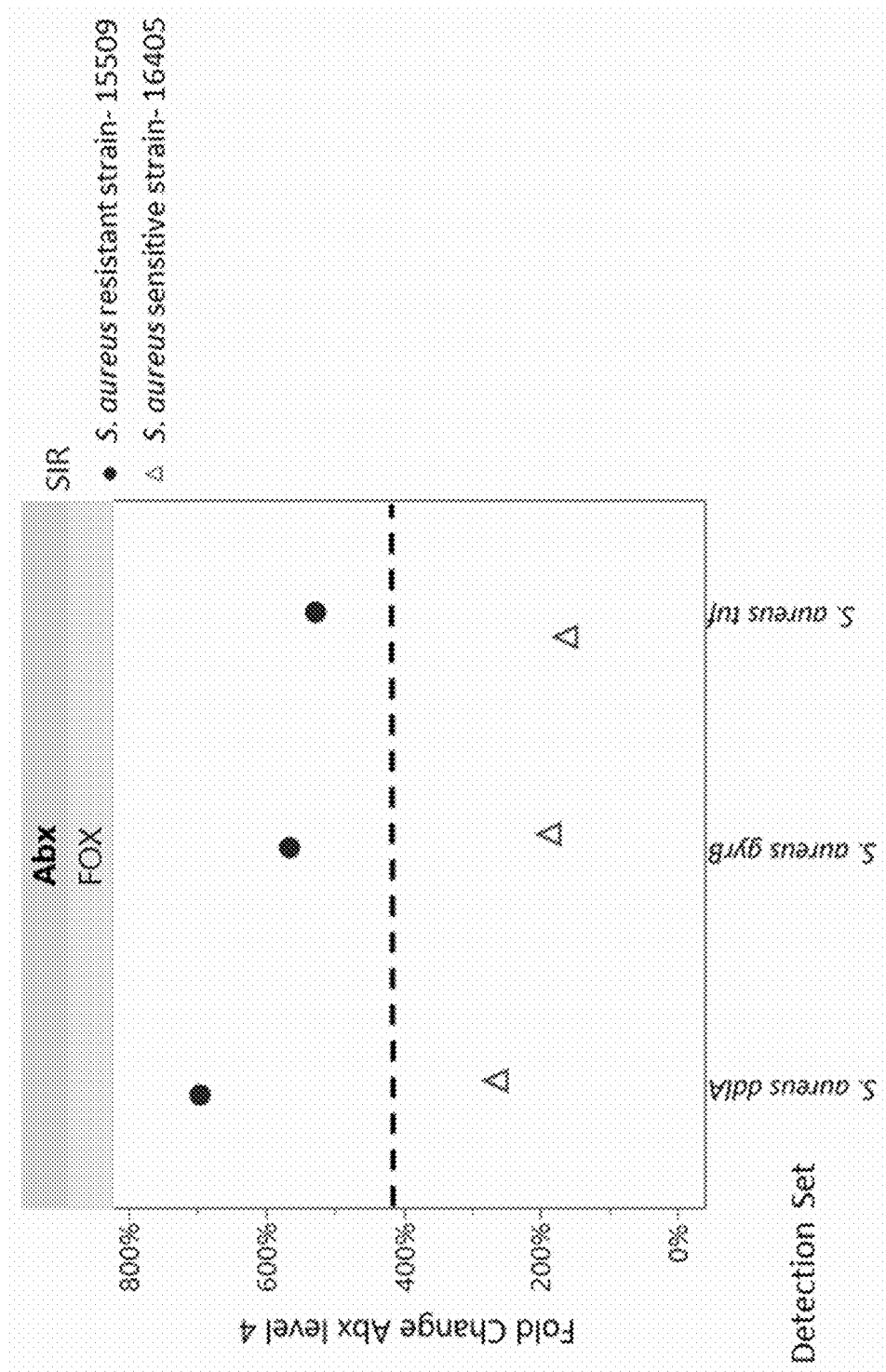

FIG. 36. Rapid Identification and phenotypic antimicrobial susceptibility testing of *S. aureus* utilizing three distinct target genes (gyrB, ddlA, tuf) and one class of antibacterial agent: cephalosporin (FOX).

Figure 37:
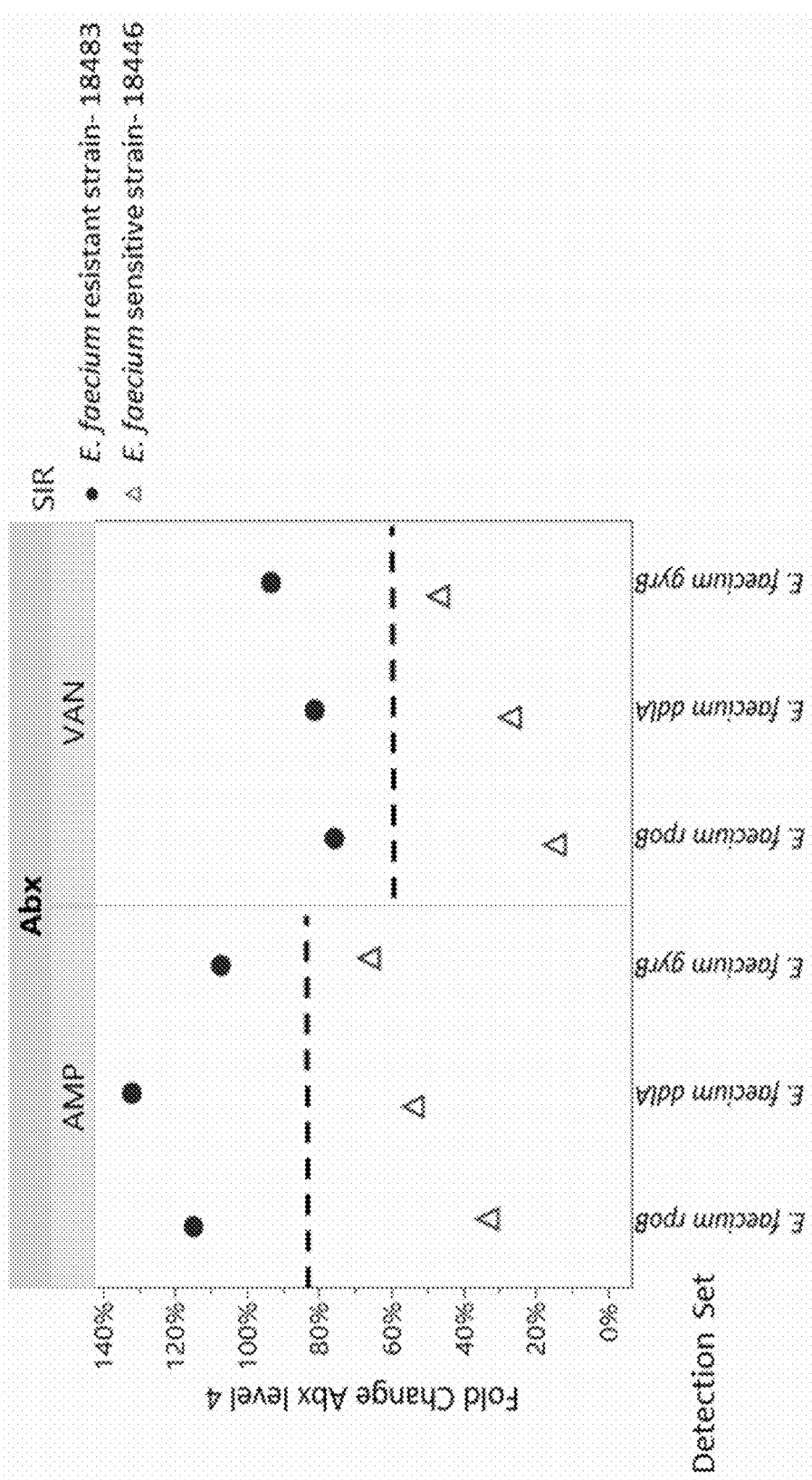

FIG. 37. Rapid Identification and phenotypic antimicrobial susceptibility testing of *Enterococcus faecium* utilizing three distinct target genes (rpoB, ddl, and gyrB) and two classes of antibacterial agents: beta-lactam (AMP) and glycopeptide (VAN).

FIG. 38. Primers and Probes that target the RDN18 and RDN58 genes to be used for rapid identification and phenotypic antimicrobial susceptibility testing of *Candida.*

FIG. 39. Primers and Probes that target the 16 s gene to be used for rapid identification and phenotypic antimicrobial susceptibility testing of any given Gram-negative or Gram-positive bacteria.

Figure 40A:
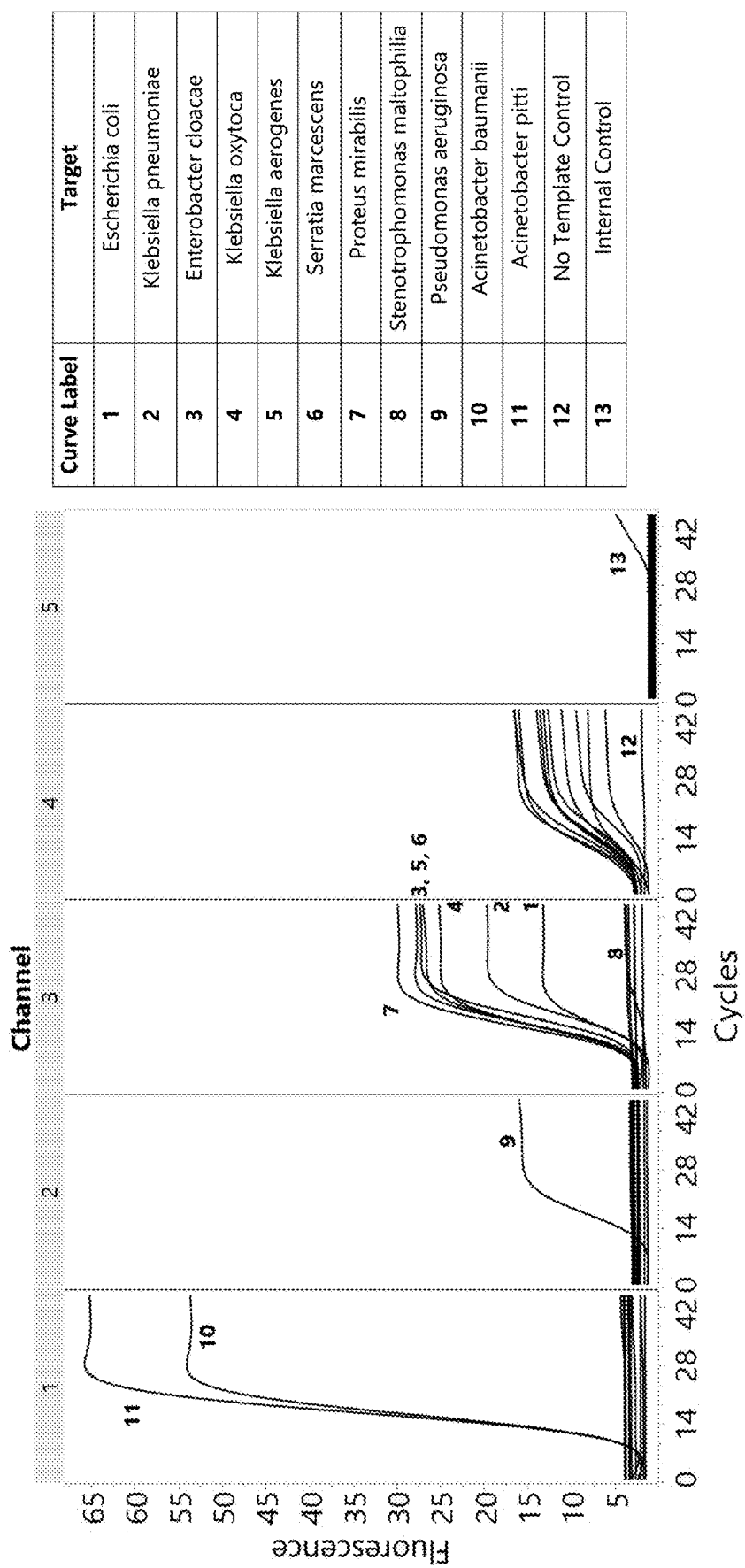

FIG. 40A. Inclusivity and exclusivity performance of a Gram-negative pathogen PCR multiplex master mix. FIG. 40B. Breakpoint groups, channels and dye wavelengths and names of the multiplex PCR assay.

Figure 41A:
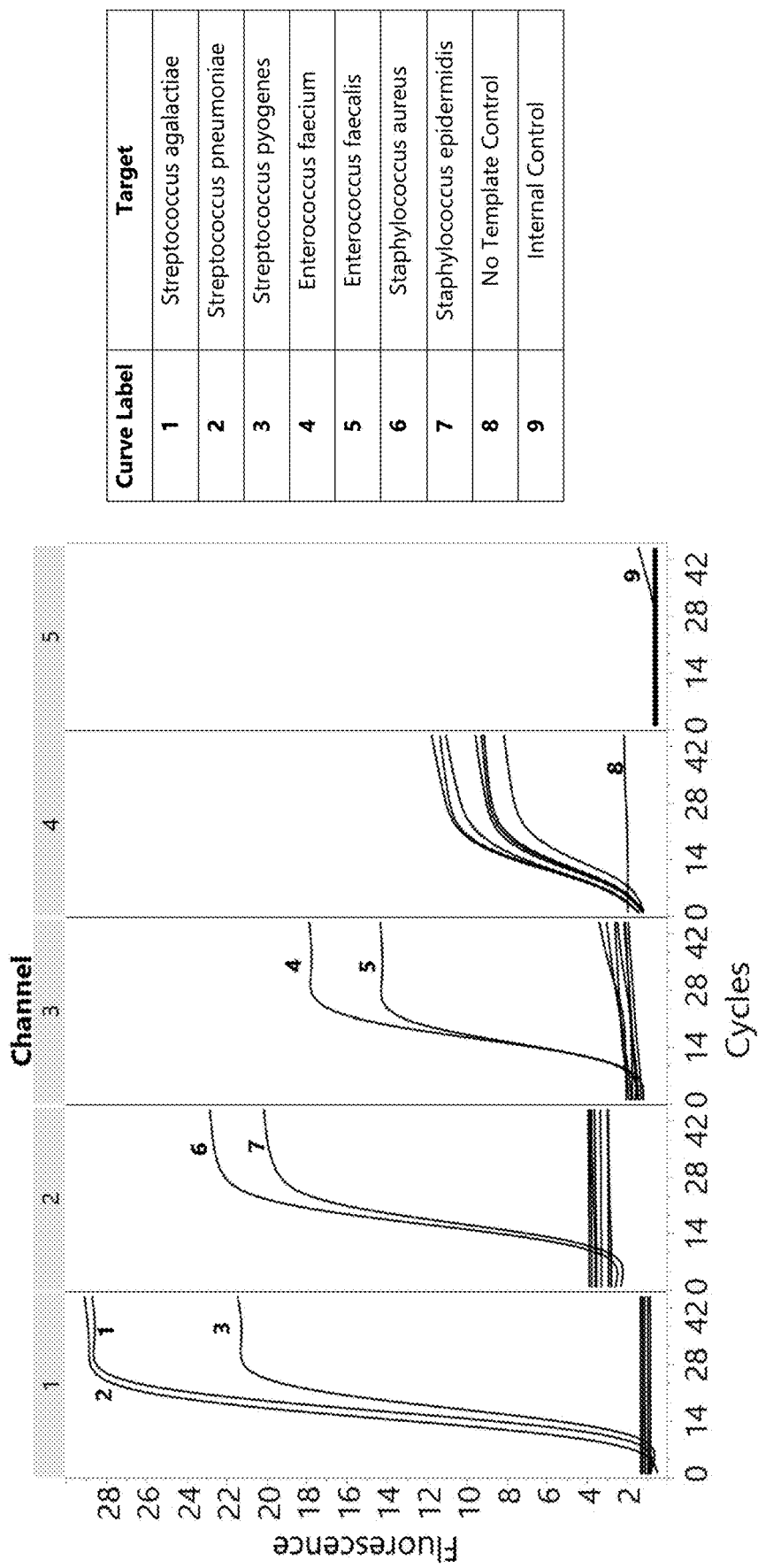

FIG. 41A. Inclusivity and exclusivity performance of a Gram-positive pathogen PCR multiplex master mix. FIG. 41B. Breakpoint groups, channels and dye wavelengths and names of the multiplex PCR assay.

Figure 42:
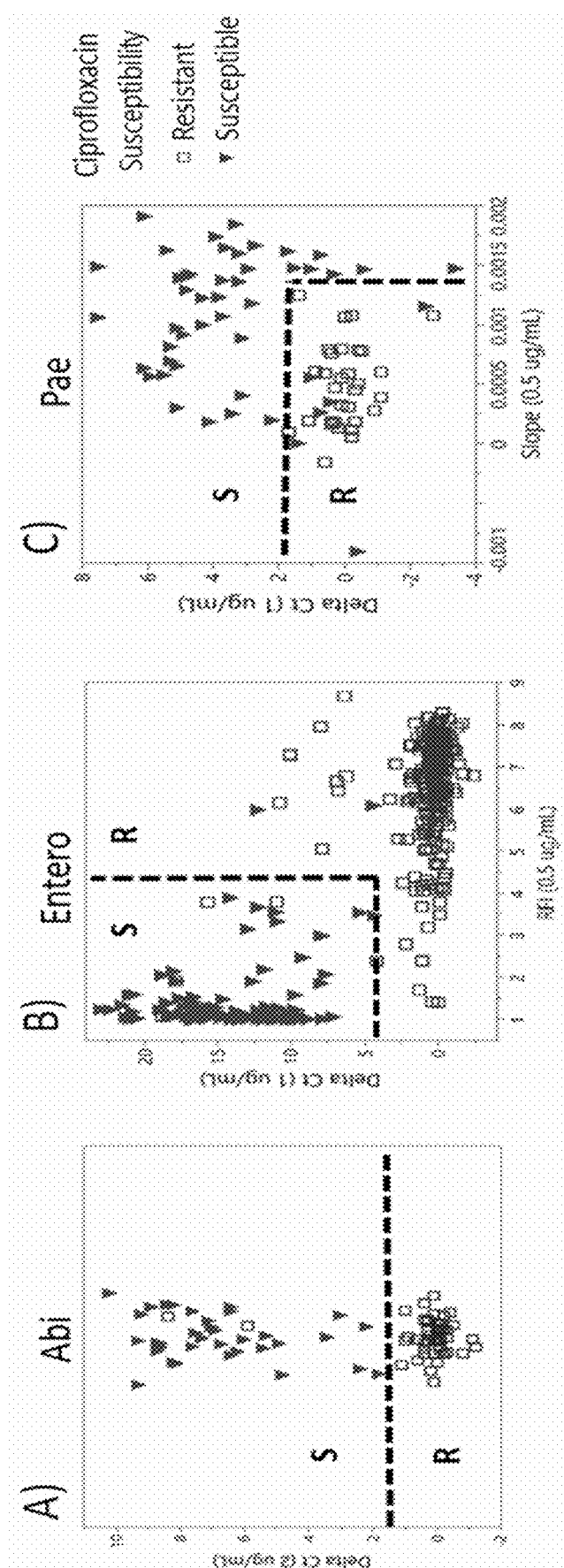

FIG. 42. Thresholds to distinguish between susceptible and resistant can be unique to each primer/probe set and are determined using statistical separation of populations as outlined in FIG. 4. The thresholds associated with ciprofloxacin susceptibility are shown for A) *Acinetobacter baumanii* (Abi), B) Enterobacteriaceae (Entero), and C) *Pseudomonas aeruginosa* (Pae), and are based on changes in Ct value, Relative Fluorescence Intensity (RFI), and Slope prior to the Ct fluorescence value at three different antibiotic concentrations.

FIG. 43. A) The distribution of resistant and susceptible isolates is shown for *A. baumanii* (Abi), *E. cloacae* (Ecl), *E. coli* (Eco), *K. aerogenes* (Kae), *K. pneumoniae* (Kpn), and *P. aeruginosa* (Pae). B) Sensitivity, specificity, and categorical agreement for ciprofloxacin across species using the thresholds in FIG. 42, where sensitivity and specificity are as defined in EXAMPLE 21.

Figure 44:
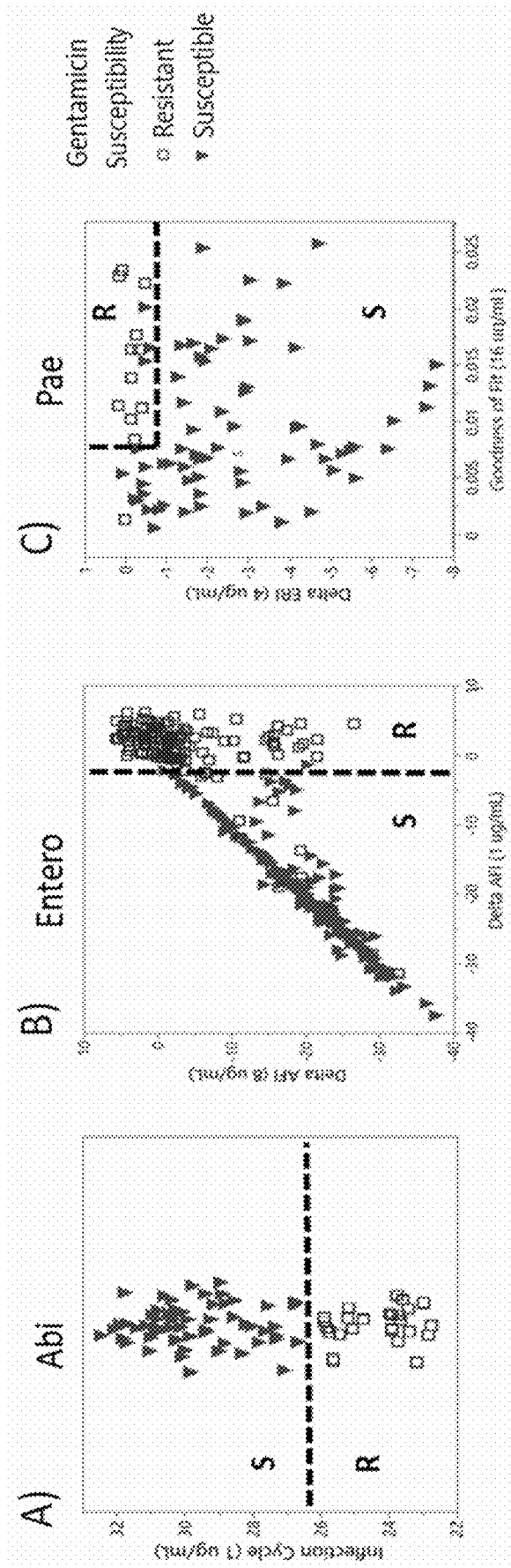

FIG. 44. Thresholds to distinguish between susceptible and resistant can be unique to each primer/probe set and are determined using statistical separation of populations as outlined in FIG. 4. The thresholds associated with gentamicin susceptibility are shown for A) *Acinetobacter baumanii* (Abi), B) Enterobacteriaceae (Entero), and C) *Pseudomonas aeruginosa* (Pae), and are based on Inflection cycle, changes in Absolute Fluorescence Intensity (AFI), and Goodness of Fit for the curve fit to the raw fluorescence data.

Figure 45:
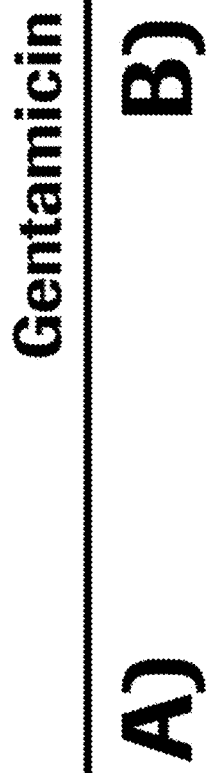

FIG. 45. A) The distribution of resistant and susceptible isolates is shown for *A. baumanii* (Abi), *E. cloacae* (Ecl), *E. coli* (Eco), *K. aerogenes* (Kae), *K. pneumoniae* (Kpn), and *P. aeruginosa* (Pae). B) Sensitivity, specificity, and categorical agreement for gentamicin across species using the thresholds in FIG. 44, where sensitivity and specificity are as defined in EXAMPLE 21.

Figure 46:
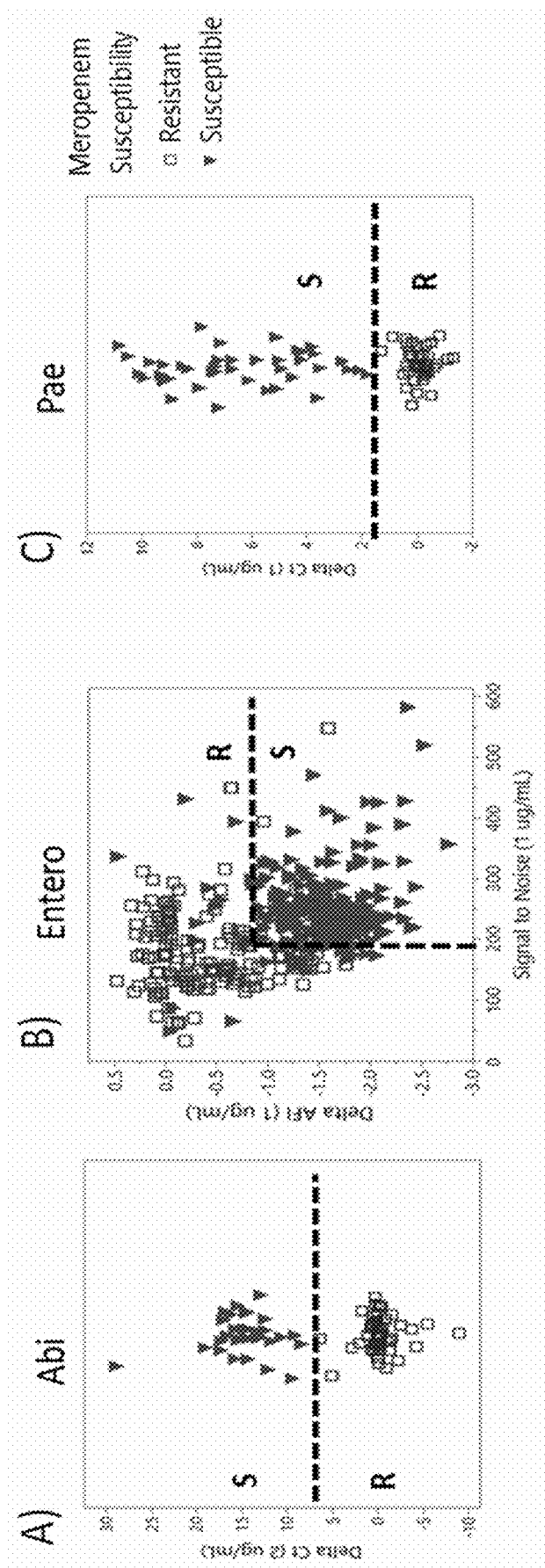

FIG. 46. Thresholds to distinguish between susceptible and resistant can be unique to each primer/probe set and are determined using statistical separation of populations as outlined in FIG. 4. The thresholds associated with meropenem susceptibility are shown for A) *Acinetobacter baumanii* (Abi), B) Enterobacteriaceae (Entero), and C) *Pseudomonas aeruginosa* (Pae), and are based on changes in Ct value relative to no antibiotic and the lowest antibiotic concentration, the absolute Ct value, and the Absolute Fluorescence Intensity (AFI).

FIG. 47. A) The distribution of resistant and susceptible isolates is shown for *A. baumanii* (Abi), *E. cloacae* (Ecl), *E. coli* (Eco), *K. aerogenes* (Kae), *K. pneumoniae* (Kpn), and *P. aeruginosa* (Pae). B) Sensitivity, specificity, and categorical agreement for meropenem across species using the thresholds in FIG. 46, where sensitivity and specificity are as defined in EXAMPLE 21.

Figure 48:
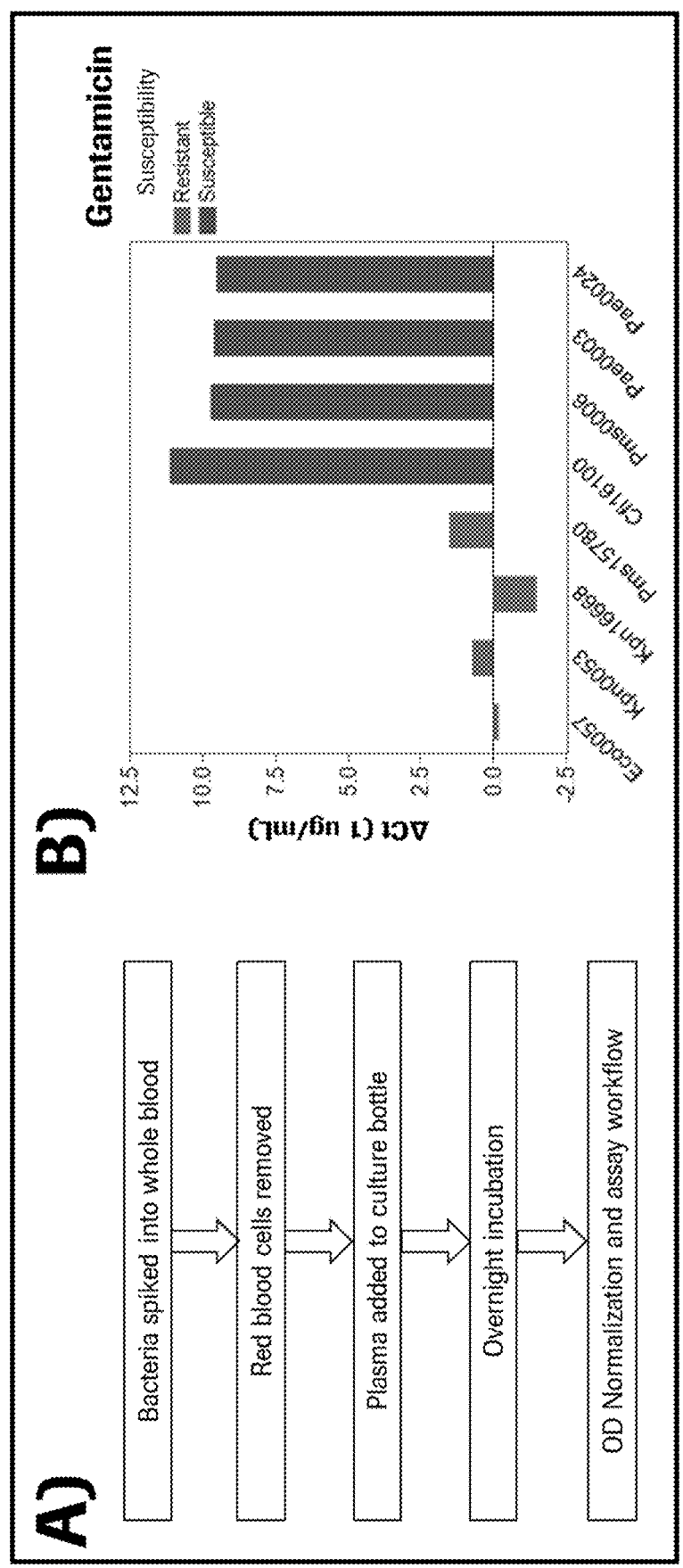

FIG. 48. A) Workflow for testing isolates directly from positive blood culture samples, which were created by spiking bacteria into whole blood, separating red blood cells, inoculating plasma containing bacteria into a commercial blood culture bottle, incubating overnight, and then following standard assay workflow. B) Change in Ct values as a function of antibiotic (Gentamicin) for various resistant and susceptible isolates, showing that phenotypic results can be obtained on bacteria directly from positive blood culture.

Figure 49:
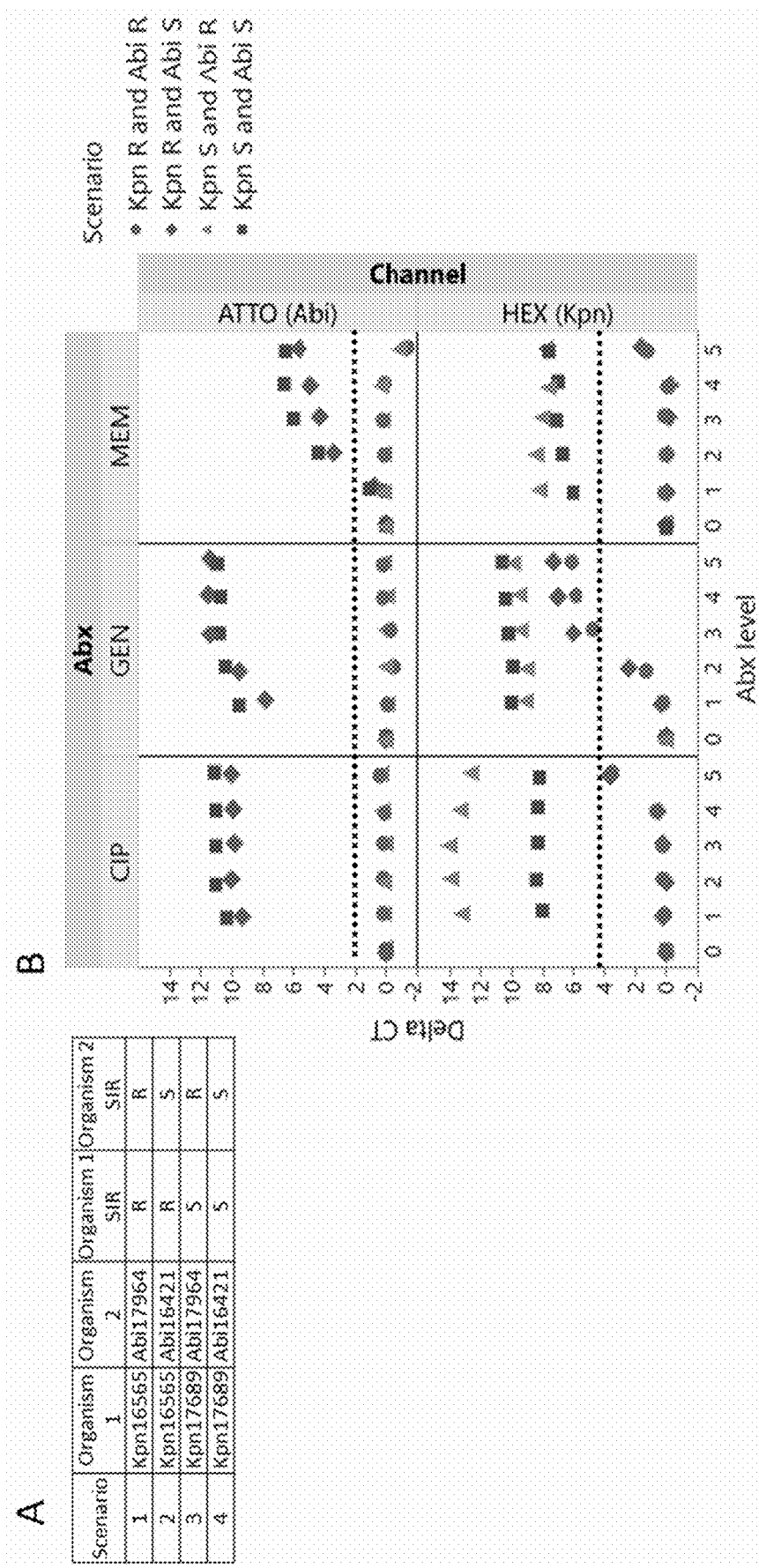

FIG. 49. Polymicrobial AST where a 1:1 ratio of two Gram-negative organisms (Kpn and Abi) with different susceptibility combinations were co-incubated together in the absence or presence of three different antibiotics at varying concentrations. Each species displayed the appropriate phenotype in the corresponding detection channel as indicated by a Delta CT threshold that separates susceptible and resistant isolates, providing accurate antimicrobial susceptibility results for a variety of polymicrobial scenarios.

Figure 50:
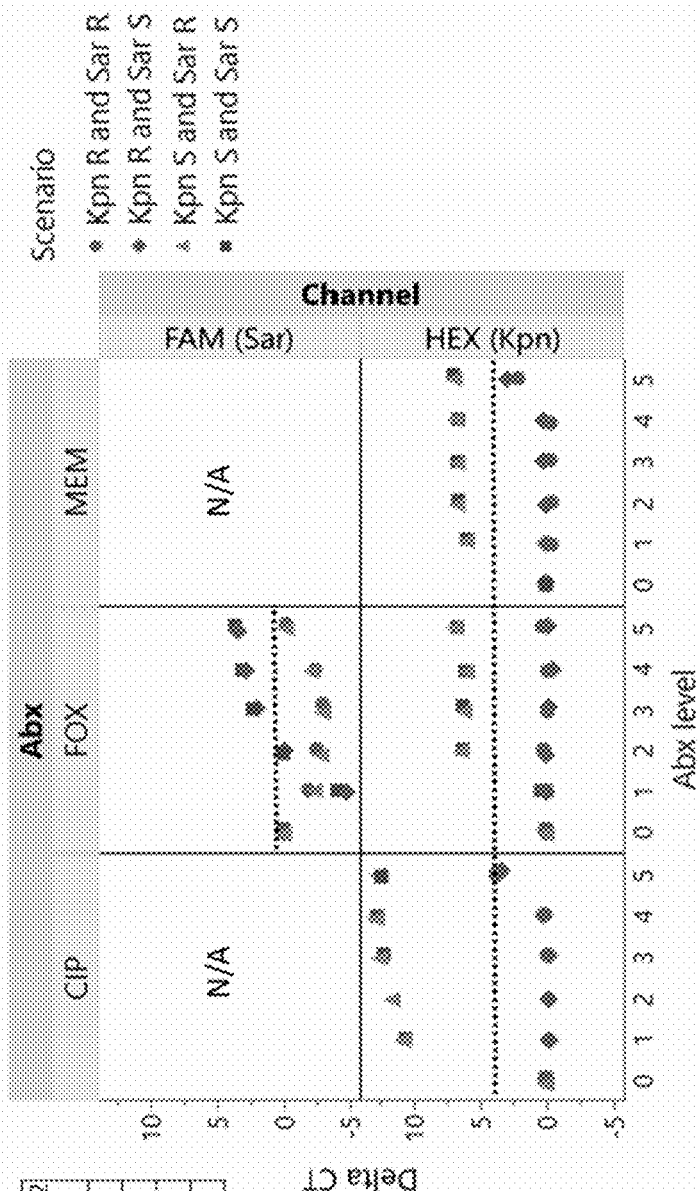

FIG. 50. Polymicrobial AST where a 1:1 ratio of one Gram-negative organism (Kpn) and one Gram-positive organism (Sar) with different susceptibility combinations were co-incubated together in the absence or presence of three different antibiotics at varying concentrations. Each species displayed the appropriate phenotype in the corresponding detection channel as indicated by a Delta CT threshold that separates susceptible and resistant isolates, providing accurate antimicrobial susceptibility results for a variety of polymicrobial scenarios. N/A indicates that there is no clinically relevant interpretation for the corresponding bacteria-drug combination.

Figure 51:
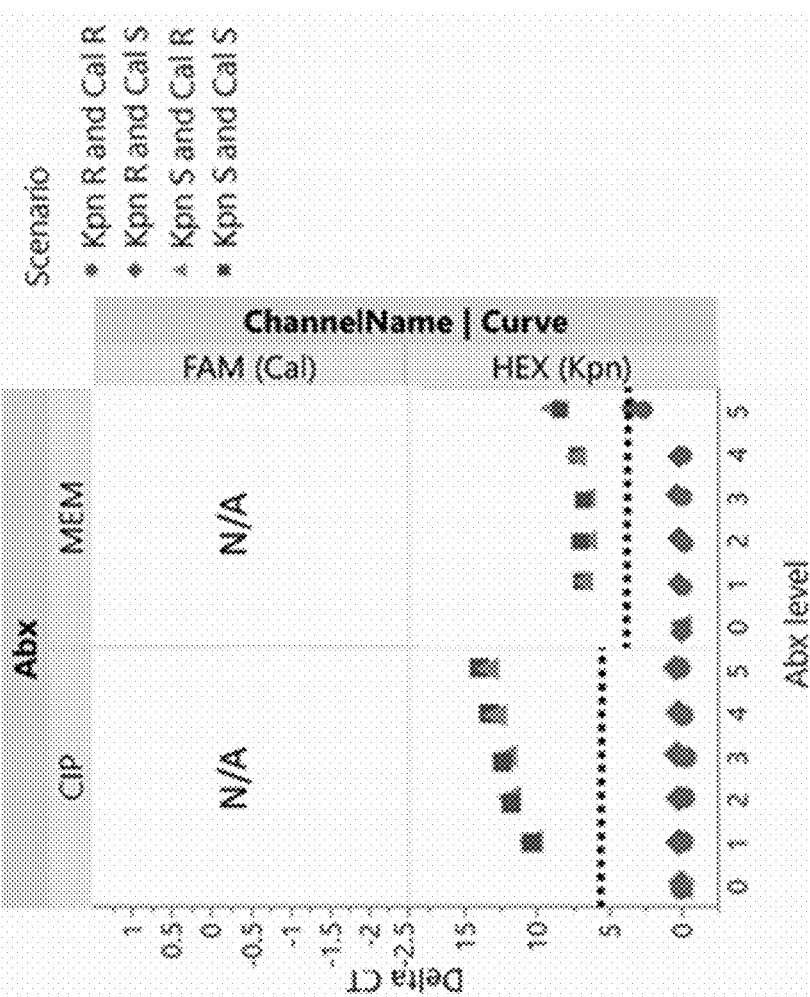

FIG. 51. Polymicrobial AST where a 1:1 ratio of one Gram-negative organism (Kpn) and one fungal organism (Cal) with different susceptibility combinations were co-incubated together in the absence or presence of one antibiotic at varying concentrations. The Gram-negative species displayed the appropriate phenotype in the corresponding detection channel as indicated by a Delta CT threshold that separates susceptible and resistant isolates, providing accurate antimicrobial susceptibility results for a variety of polymicrobial scenarios. N/A indicates that there is no clinically relevant interpretation for the corresponding organism-drug combination. Cal susceptibility for fluconazole is indicated.

Figure 52:
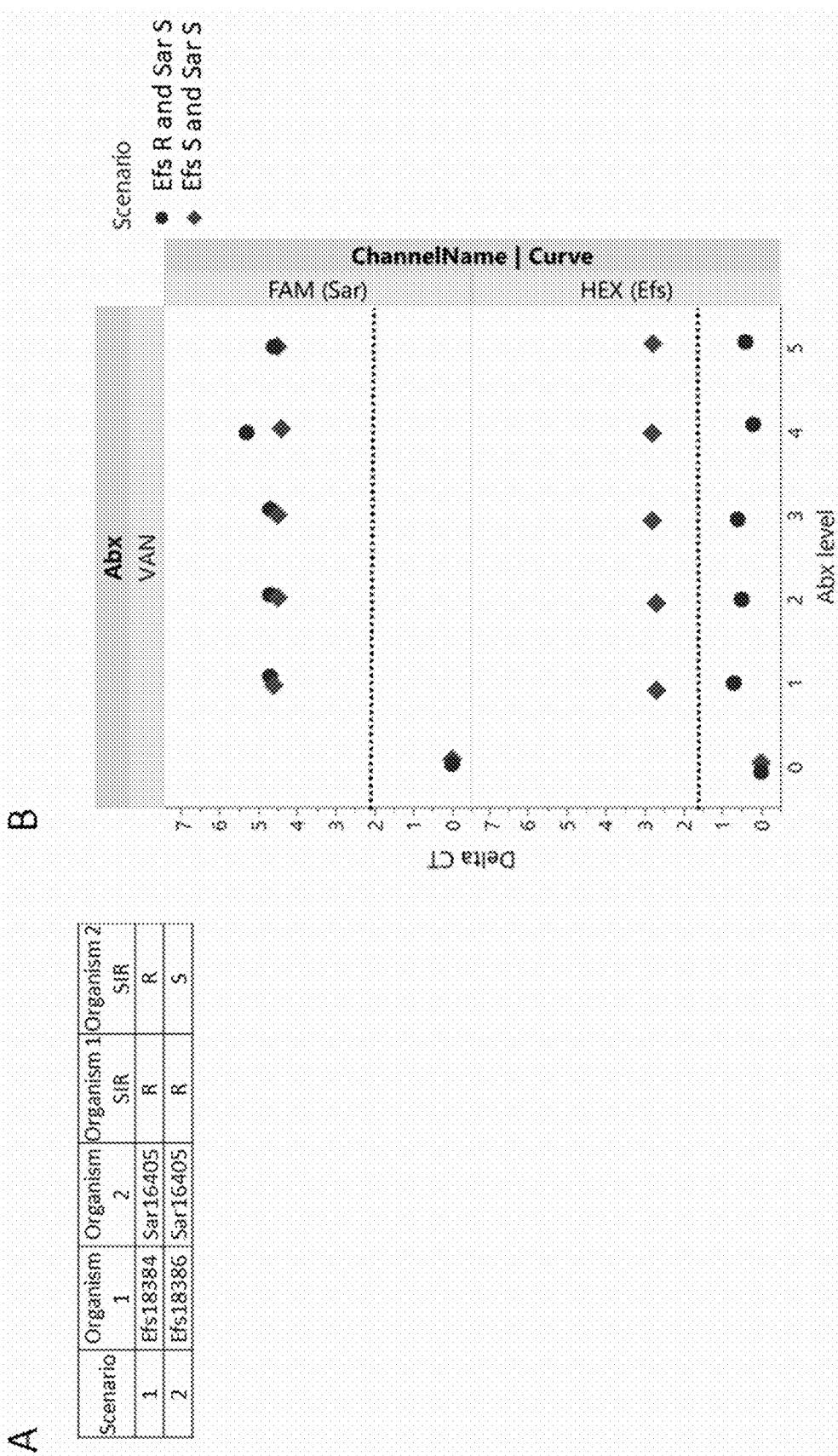

FIG. 52. Polymicrobial AST where a 1:1 ratio of two Gram-positive organisms (Efs and Sar) with different susceptibility combinations were co-incubated together in the absence or presence of one antibiotic at varying concentrations. Both species displayed the appropriate phenotype in the corresponding detection channel as indicated by a delta-Ct threshold that separates susceptible and resistant isolates, providing accurate antimicrobial susceptibility results for a variety of polymicrobial scenarios.

Figure 53:
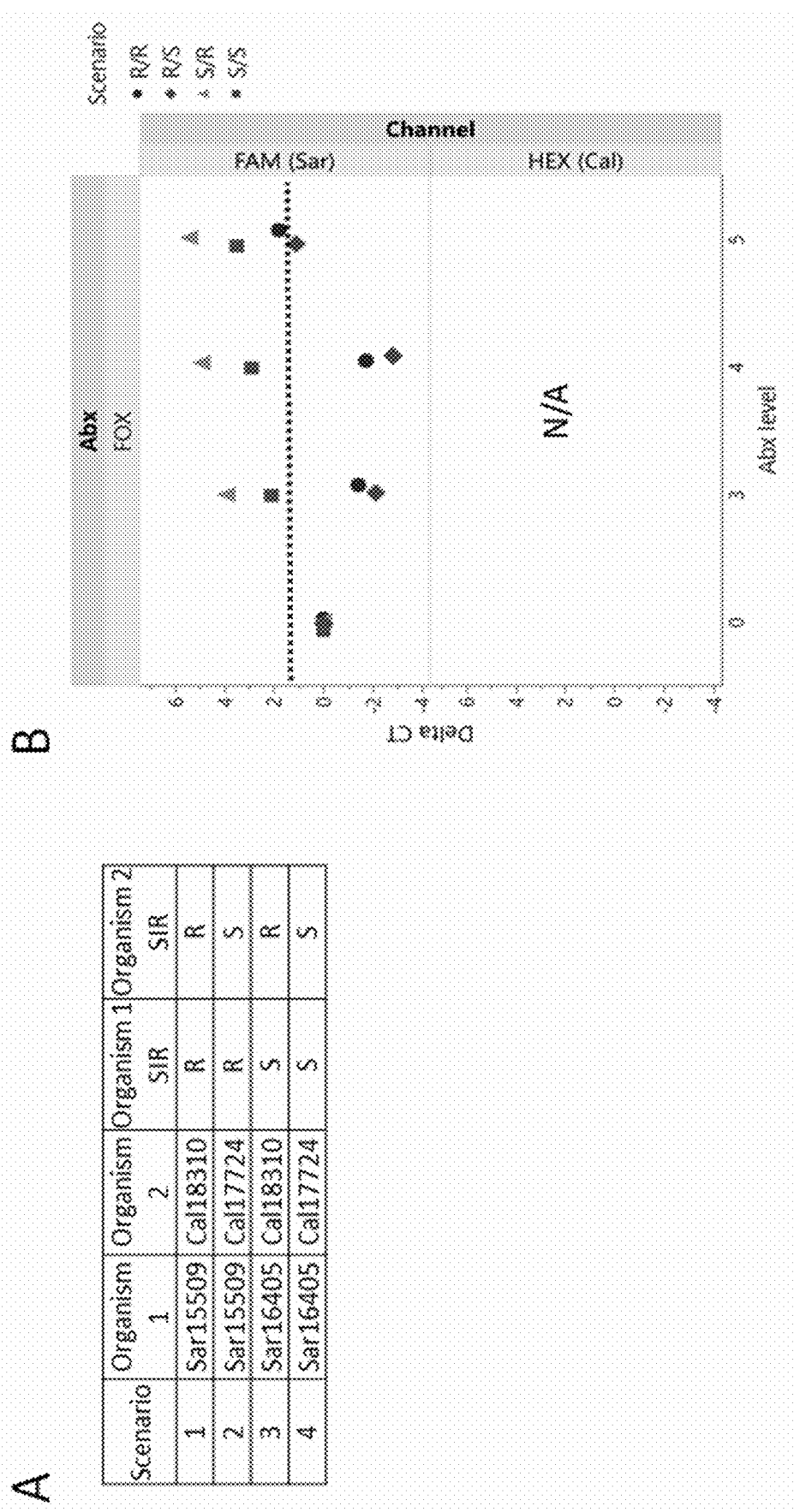

FIG. 53. Polymicrobial AST where a 1:1 ratio of one Gram-positive organism (Sar) and one fungal organism (Cal) with different susceptibility combinations were co-incubated together in the absence or presence of one antibiotic at varying concentrations. The Gram-positive species displayed the appropriate phenotype in the corresponding detection channel as indicated by a delta-Ct threshold that separates susceptible and resistant isolates, providing accurate antimicrobial susceptibility results for a variety of polymicrobial scenarios. N/A indicates that there is no clinically relevant interpretation for the corresponding organism-drug combination. Cal susceptibility for fluconazole is indicated.

FIG. 54. PCR assays using primers and probes disclosed in TABLE XXXIX that target the blaKPC, blaVIM, blaNDM, and blaOXA-48 genes were tested against Gram-negative pathogens with known mechanisms of carbapenem resistance. Positive (Pos) signals were observed only for the targeted resistance mechanism.

Figure 55:
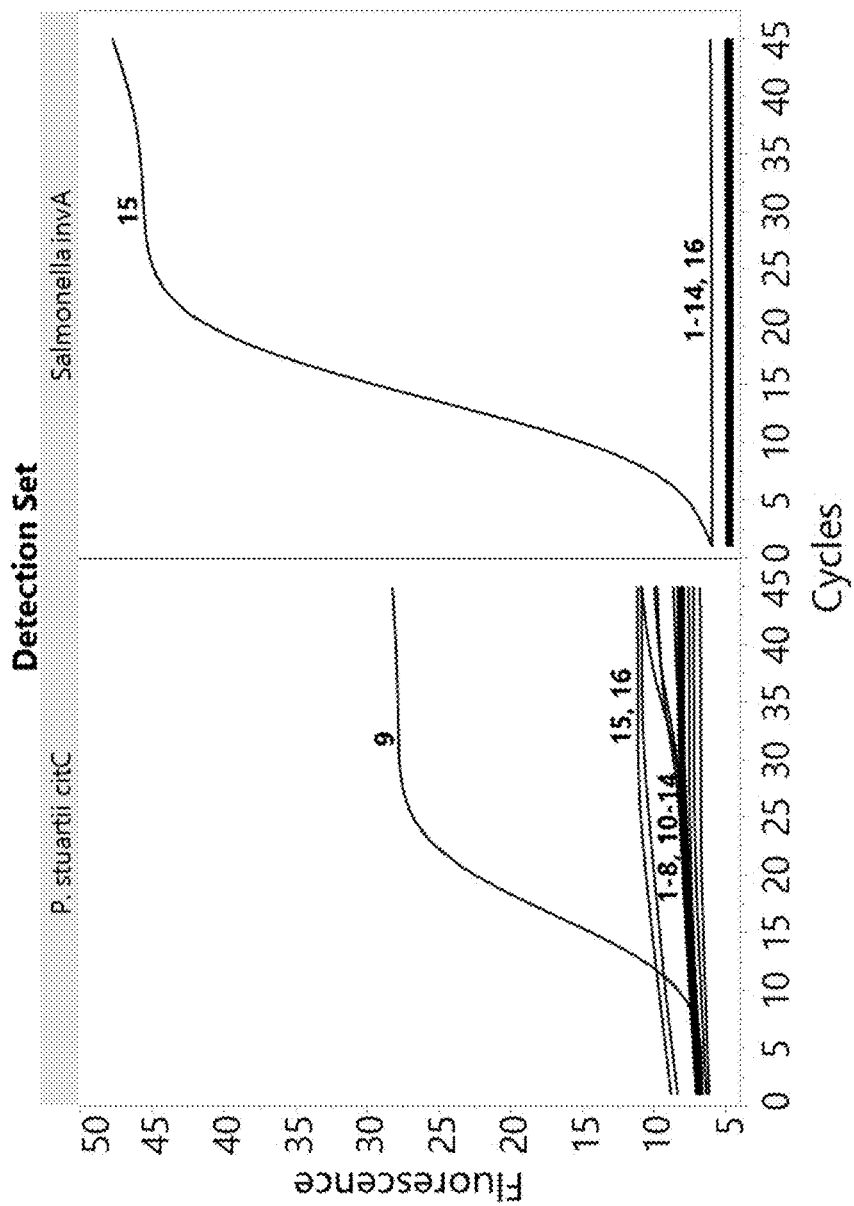

FIG. 55. PCR assays using primers and probes disclosed in TABLE XL that target the citC gene of *P. Stuartii* and invA gene of *Salmonella* were tested against common Gram-negative pathogens: *E. coli, K. pneumoniae, E. cloacae, K. oxytoca, K. aerogenes, S. marcscens, P. mirabilis, C. freundii, P. stuartii, P. rettgeri, S. enterica, S. maltophilia, P. aeruginosa, A. baumannii,* and *A. pittii*. Only species-specific growth curves were observed. These results represent non-limiting examples of species-specific detection sets that allow improved breakpoint based AST calling for some specific species within the order Enterobacterales.

Figure 56:
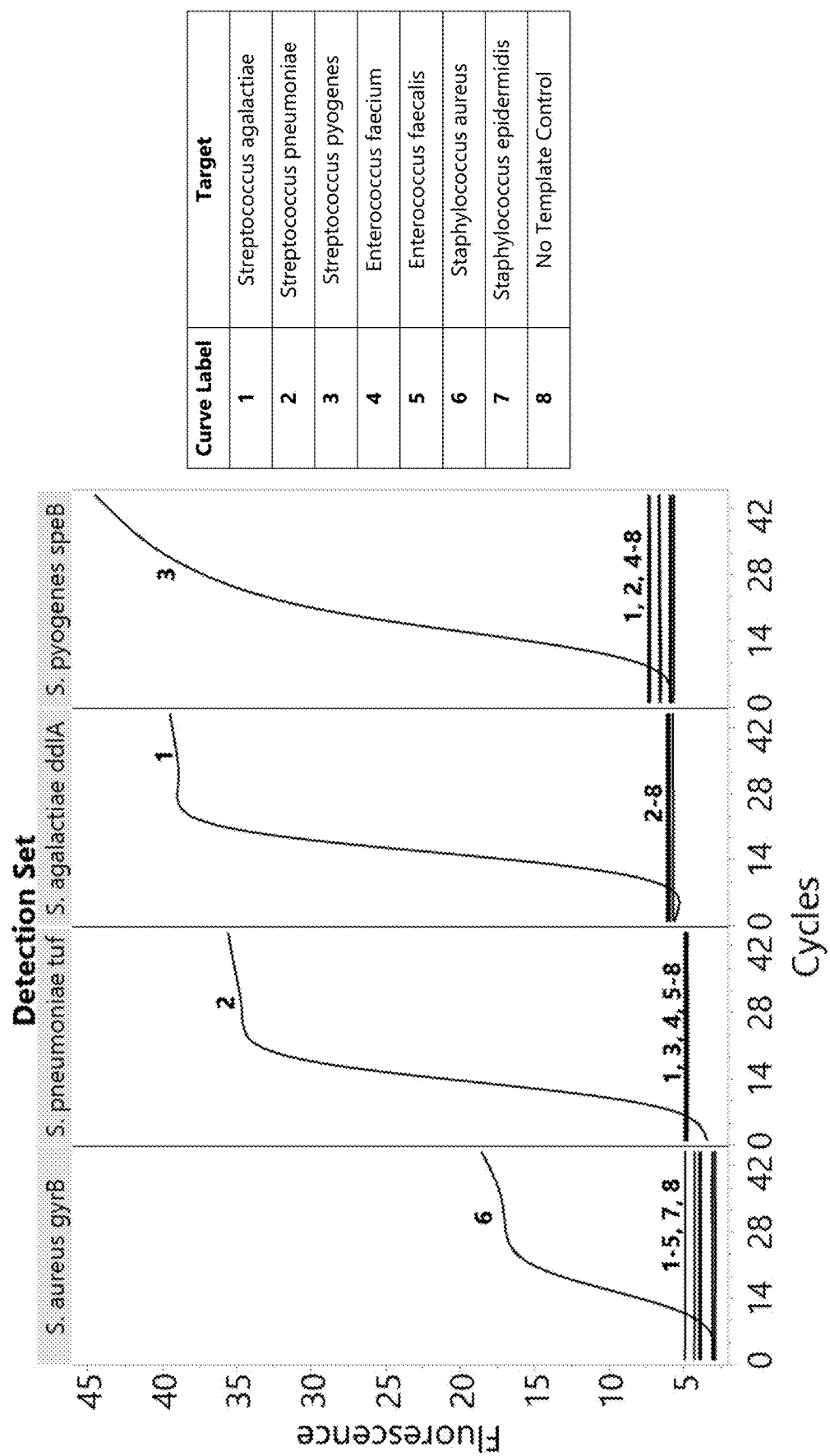

FIG. 56. PCR assays using primers and probes disclosed in TABLE XLI that target gyrB gene of *S. agalactiae*, ddlA gene of *S. agalactiae*, tuf gene of *S. pneumonia*, and speB gene of *S. pyogenes* were tested against common Gram-positive pathogens: *S. agalactiae, S. pneumoniae, S. pyogenes, E. faecium, E. faecalis, S. aureus,* and *S. epidermidis*. Only species-specific growth curves were observed. These results represent non-limiting examples of species-specific detection sets that allow improved breakpoint based AST calling for some specific species within the *Staphylococcus* and *Streptococcus* genera.

Figure 57:
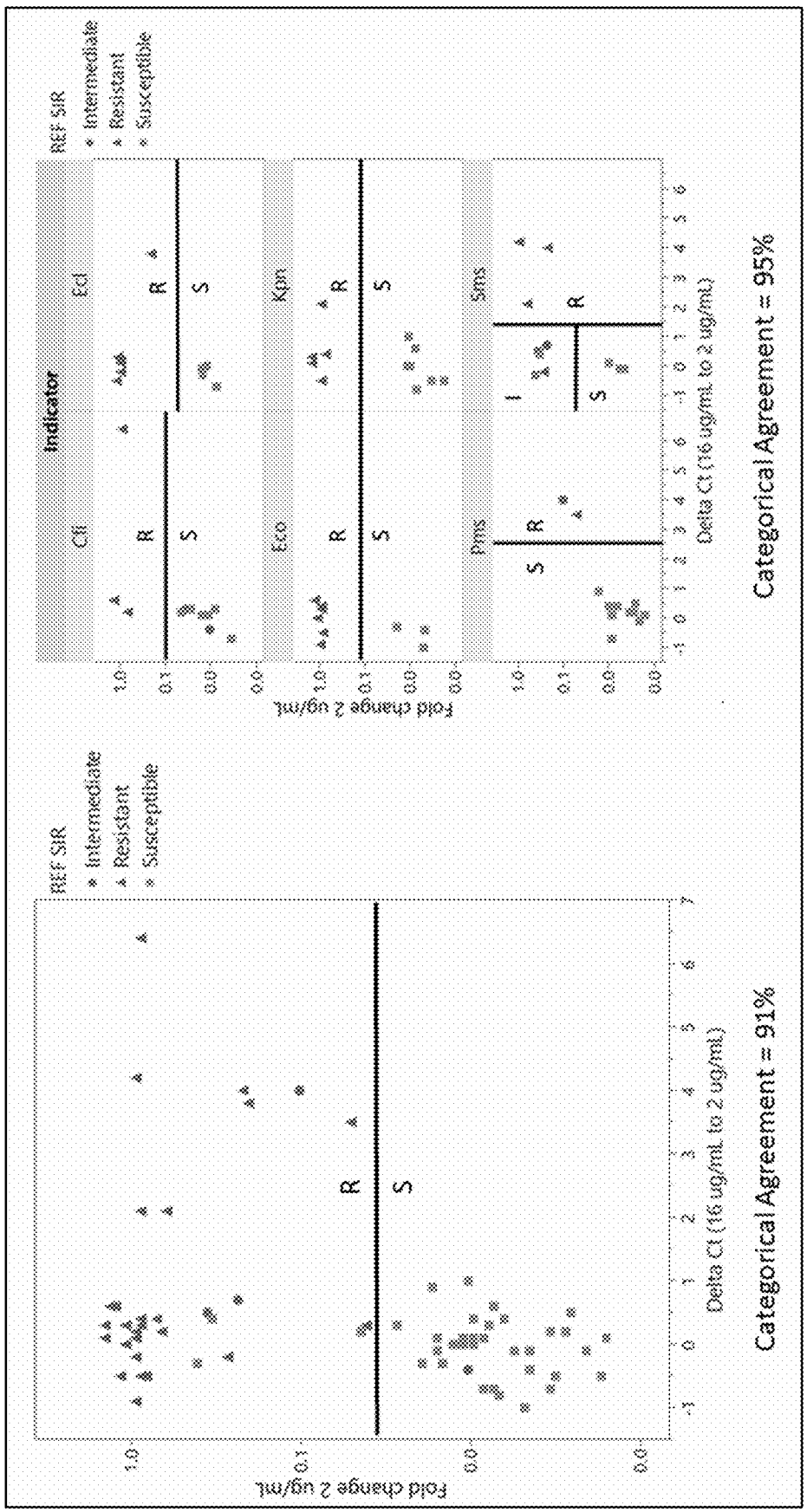

FIG. 57. The left panel shows the thresholds to distinguish between susceptible and resistant strains in an ID-AST PCR assay that utilized non-species-specific primer/probe sets (e.g. sets that hybridize to a target gene in the Enterobacteriales order) may be comfounded by species-specific differences in phenotype manifestation. The right panel shows the use of species-specific primer/probe sets that provide species identification would enable separate interpretation for each individual species, leading to improved Categorical Agreement to CLSI standards.

Figure 58:
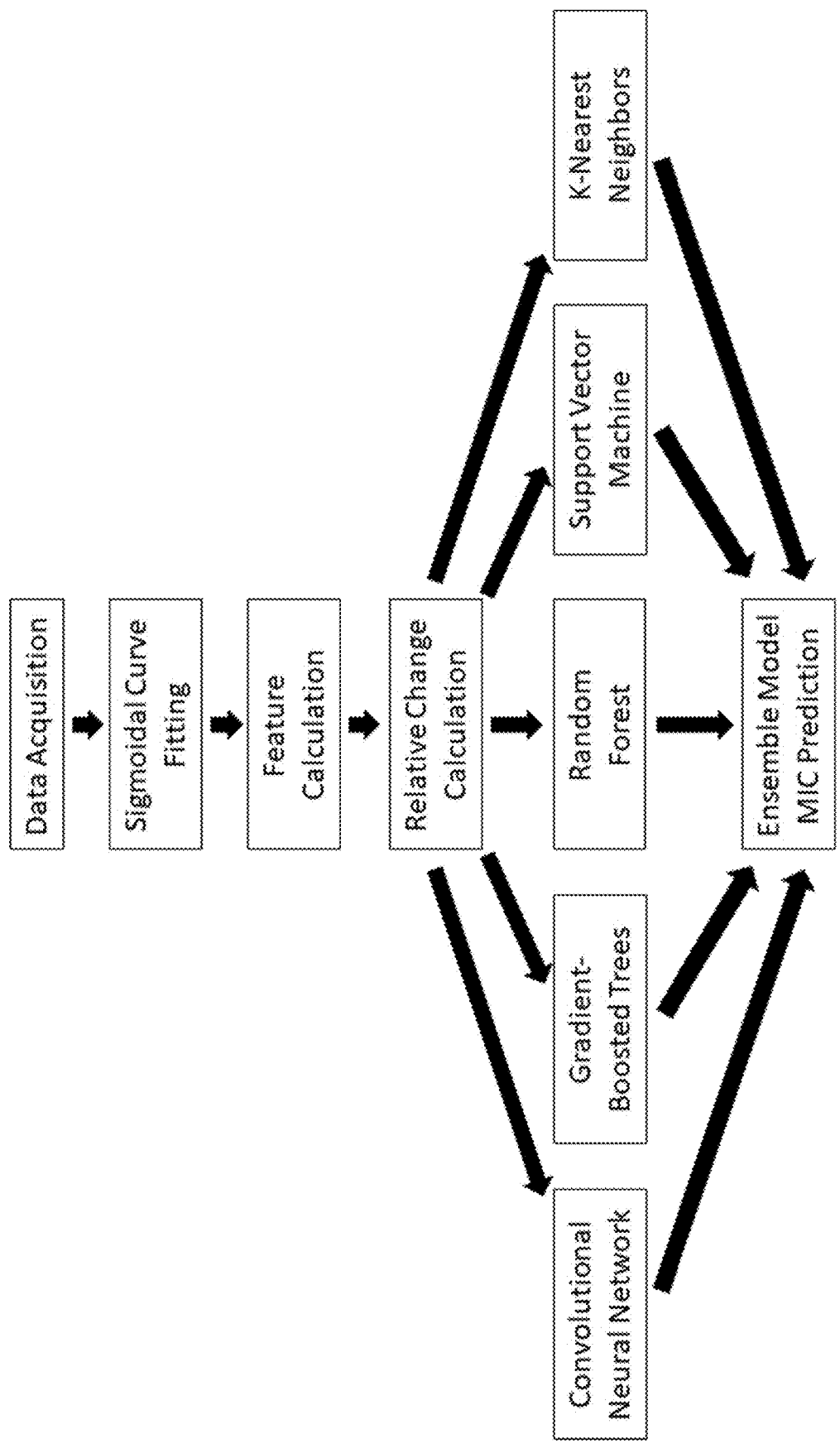

FIG. 58. Data interpretation strategy wherein a sigmoidal function is fit to the raw PCR curve data followed by calculation of curve parameters and features. Features are then compared between the presence of various antibiotic concentrations and the no-antibiotic reference to derive relative feature changes. Relative change features are then input into separate machine learning algorithms along with the ground truth MIC in order to train predictive models. Trained models then participate as a voting ensemble to return the final predicted MIC.

Figure 59:
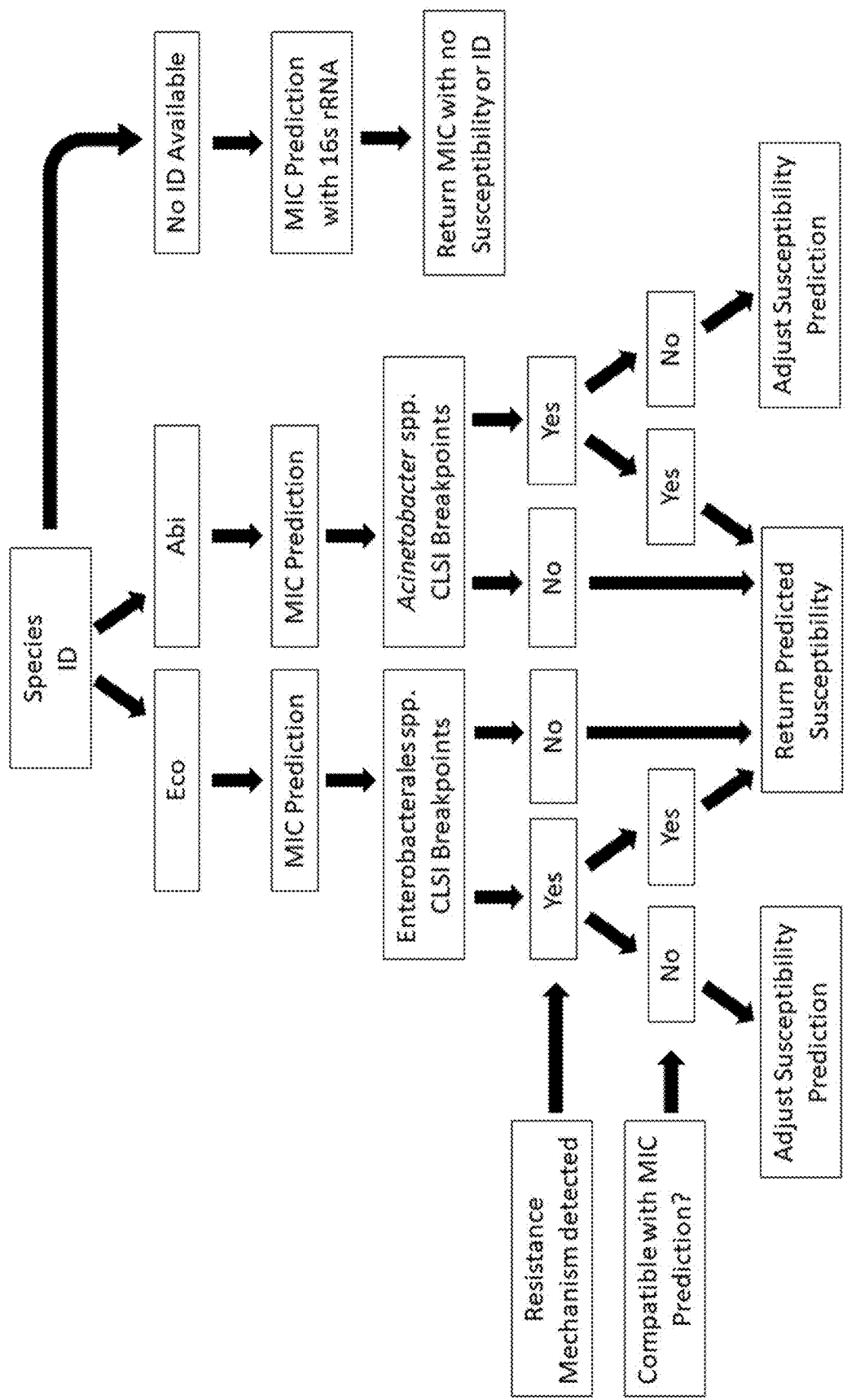

FIG. 59. Diagram indicating how Species ID, Antimicrobial Susceptibility Testing, Resistance Mechanism detection, and Universal 16 s rRNA phenotypic information is combined to return a result, wherein Species ID is used to select the appropriate algorithm for MIC prediction which is then compared to the appropriate breakpoints from regulatory bodies to determine susceptibility information.

DETAILED DESCRIPTION OF THE INVENTION

Definitions

The disclosed methods may include performing at least one cycling step that includes amplifying one or more portions of the nucleic acid molecule gene target from a sample using one or more pairs of primers. A "sample" or "biological sample" as used herein refers to a sample that includes but is not limited to whole blood, plasma, serum, red blood cell fraction, saliva, cerebrospinal fluid, semen, stool, urine, rectal swab, bile, lymph, sputum, lavage fluid, or a combination thereof. "Primer(s)" as used herein refer to oligonucleotide primers that specifically anneal to the target bacterial gene, and initiate DNA synthesis therefrom under appropriate conditions producing the respective amplification products. Each of the discussed primers anneals to a target within or adjacent to the respective target nucleic acid molecule such that at least a portion of each amplification product contains nucleic acid sequence corresponding to the target. The one or more amplification products are produced provided that one or more of the target bacterial gene nucleic acid is present in the sample, thus the presence of the one or more of target bacterial gene amplification products is indicative of the presence of that bacterial strain in the sample. The amplification product should contain the nucleic acid sequences that are complementary to one or more detectable probes for target bacterial gene. "Probe(s)" as used herein refer to oligonucleotide probes that specifically anneal to nucleic acid sequence encoding the target bacterial gene. Each cycling step includes an amplification step, a hybridization step, and a detection step, in which the sample is contacted with the one or more detectable probes for detection of the presence or absence of the bacterial strain in the sample.

As used herein, the term "amplifying" refers to the process of synthesizing nucleic acid molecules that are complementary to one or both strands of a template nucleic acid molecule. Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except possibly for the intended function—no fundamental difference between a "primer", an "oligonucleotide", or a "probe".

The term "hybridizing" refers to the annealing of one or more probes to an amplification product. Hybridization conditions typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus,* and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-O-methyl Ribo-U, 2'-O-methyl Ribo-C, an N4-ethyl-dC, an N6-methyl-dA, and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference.

The term "TAGS" or "Temperature Assisted Generation of Signal" (disclosed in U.S. Patent Publication No. 2018/0073064 and incorporated by reference herein in its entirety) is a multiplexing technology that enables the measurement of multiple individual targets in each fluorescence channel by collecting fluorescence data at different temperatures during thermal cycling. Consequently, TAGS multiplexing with two or three temperature channels can double or triple the number of resolvable targets per optical channel. In principle, this technology can be deployed on any quantitative PCR (qPCR) instrument capable of collecting more than one fluorescence read per PCR cycle.

The term "colonization" is defined as the presence of bacteria or fungi on a body surface (like on the skin, mouth, intestines or airway) without necessarily causing disease in the person. The term "infection" is defined as the invasion of a host organism's bodily tissues by disease-causing organisms (such as bacteria and fungi). Infection also results from the interplay between pathogens and the defenses of the hosts they infect.

The term "antimicrobial" refers to an agent or drug used to treat a microbial infection, usually by killing the microorganism or by inhibiting its growth. Antimicrobials may include antibiotics for treating bacterial infection, antifungals for treating fungi infection, antiprotozoals for treating protozoan infection and antivirals for treating viral infection. Antimicrobials are classified in several different manners (and referred as "antimicrobial class") and include classification by mechanism of action (e.g. inhibition of cell wall synthesis, inhibition of protein or nucleic acid synthesis, disruption of cell membrane), by source (e.g. from natural sources or synthetic), and by chemical structure (e.g. β-lactams, aminoglycosides, macrolides, quinolones etc.).

Examples of antimicrobial classes include but are not limited to: Allylamines, Amidinopenicillins, Aminocyclitols, Aminoglycosides, Amphenicols, Ansamycins, B-3-Glucan synthase inhibitors, Carbapenems, Cephalosporins, Clycylcyclines, Cyclic polypeptides, Glycopeptides, Imidazoles, Lincosamides, Lipopeptides, Macrolides and ketolides, Monobactams, Nitrofurantoins, Nitroimidazoles, Oxazolidinones, Penicillins, Phophonic acid derivatives, Pleuromutilins, Polyenes, Polymyxins, Pseudomonic acids, Quinolones, Riminofenazines, Steroid antibacterials, Streptogramins, Sulfonamides, dihydrofolate reductase inhibitors and combinations, Sulfones, Tetracyclines, and Triazoles.

Examples of antimicrobial drugs or agents include but are not limited to: naftifine, mecillinam, spectinomycin, chloramphenicol, rifampicin, caspofungin, meropenem, ceftriaxone, cefepime, ceftaroline, tigecycline, bacitracin, vancomycin, miconazole, clindamycin, daptomycin, erythromycin, telithromycin, aztreonam, nitrofurantoin, metronidazole, linezolid, ampicillin, fosfomycin, retapamulin, amphotericin-B, colistin, mupirocin, ciprofloxacin, clofazimine, fusidic acid, quinupristin/dalfopristin, sulfamethoxazole, trimethoprim, dapsone, chlortetracycline, and fluconazole.

The term "the presence of at least one concentration" when applied to an antimicrobial/antifungal or a class of antimicrobials/antifungals refers to given concentration(s) of the antimicrobial/antifungal or the class of antimicrobials/antifungals that is/are present at value(s) that is/are not zero.

The term "Minimum Inhibitory Concentration" or "MIC" refers to the lowest concentration of an antimicrobial required to inhibit the growth of an organism. In classical culture-based tests, the MIC is determined when the bacteria are added to wells containing growth media and varying concentrations of the antimicrobial. The concentration of antimicrobial is doubled in each successive well and the MIC is found by identifying the well with the lowest antimicrobial concentration in which there is no visible growth after an incubation period. The term "breakpoint" refers to a chosen concentration of an antimicrobial that defines whether a species of bacteria is susceptible or resistant to the antimicrobial. If the MIC is less than or equal to the susceptibility breakpoint the bacteria is considered susceptible to the antimicrobial. If the MIC is greater than this value the bacteria is considered intermediate or resistant to the antimicrobial. Breakpoints can therefore be used to interpret MIC results from Antimicrobial Susceptibility Testing, and to classify "groupings" of organisms as either "Susceptible, Intermediate, or Resistant (SIR)" to a given antimicrobial or antifungal.

Breakpoints are an integral part of modern microbiology laboratory practice and are used to define susceptibility and resistance to antibacterials. Depending on the testing method, they are expressed as either a concentration (in mg/liter or g/ml) or a zone diameter (in mm). In general, all susceptibility testing methods require breakpoints, also known as interpretive criteria, so that the results of the tests can be interpreted as susceptible, intermediate, or resistant and reported as such to a broad range of clinicians. "Clinical breakpoints" which refer to those concentrations (MICs) that separate strains where there is a high likelihood of treatment success from those bacteria where treatment is more likely to fail. In their simplest form, these breakpoints are derived from prospective human clinical studies comparing outcomes with the MICs of the infecting pathogen.

Detection and Identification of Infectious Pathogens

The present disclosure provides methods to detect infectious pathogens, for example, bacteria strains that cause bloodstream infections. The methods comprise the steps of amplifying portions of target genes by PCR using strain-specific, species-specific, genus-specific, family-specific, or order-specific primer sequences and detecting the amplification products using strain-specific, species-specific, genus-specific, family-specific, or order-specific probe nucleic acid sequences. Target gene selection was the result of an in silico search of the public sequence database, as well as a literature search for nucleic acid sequences that are specific to a species (e.g. *E. coli*) or to an order (e.g. Enterobacterales) and discriminate against other strains and families. As a result of the search, the following target genes were identified:

Enterobacterales Order: rplP, ompA, tuf gyrB, rpoB
Enterobacteriaceae family: rplP, ompA, tuf gyrB, rpoB
*Enterococcus* genus: tuf rpoB, sodA, ddl, gyrB
*Pseudomonas* genus: gyrB, O-antigen acetylase, rpoB, ecfX, tuf
*Acinetobacter* genus: ompA, tusA, rpoB, gyrB
*Stenotrophomonas maltophilia*: fdnG, gyrB, tuf
*Staphylococcus aureus*: CPE, gyrB, nuc, rpoB, tuf ddlA
*Staphylococcus epidermidis*: altE, femA
Coagulase-negative Staphylococci: rpoB, tuf, sodA
*Streptococcus* genus: tuf gyrB, sip, ddlA
*Streptococcus pneumoniae*: lytA, SP2020, piaB
*Proteus mirabilis*: UreR, UreC
*Candida albicans*: ACT, RPB-1, 5.8 s ribosomal RNA, 18 s ribosomal RNA For detection of bacteria belonging to the Enterobacterales Order or to the Enterobacteriaceae family, primers and probes to amplify the rplP gene encoding for the ribosomal L16 protein are provided (SEQ ID NO: 1-3, TABLE I). Addition of a second probe (SEQ ID NO: 4, TABLE I) further extends inclusivity to include other prevalent pathogens in the order Enterobacterales, such as the strains *Serratia marcescens* and *Proteus mirabilis*. Nucleic acids other than those exemplified herein can also be used to detect highly specific pathogen grouping target genes in a sample. For example, functional variants can be evaluated for specificity and/or sensitivity by those of skill in the art using routine methods. Representative functional variants can include, e.g., one or more deletions, insertions, and/or substitutions in the target gene primers and probes disclosed herein. More specifically, embodiments of the oligonucleotides each include a nucleic acid with a sequence selected from SEQ ID NOs: 1-4, a substantially identical variant thereof in which the variant has at least, e.g., 80%, 90%, or 95% sequence identity to one of SEQ ID NOs: 1-4, or a complement of SEQ ID NOs: 1-4 and the variant.

TABLE I

Oligonucleotides for detecting Enterobacteriaceae family or Enterobacterales order
Primers and Probes that hybridize to rplP gene in *Enterobacteriaceae/Enberbacteriales* strains

| Oligonucleotide Type | Oligonucleotide Name | SEQ ID NO: | Sequence | Modifications |
|---|---|---|---|---|
| Forward primer | RM_ENTF | 1 | TAATCGGCAGTTTCGCTG<t_BB_dC> | t_BB_dC = t-butylbenzyl-dC |
| Reverse primer | RM_ENTRP | 2 | GTTCCCGGACAAACCGATC<t_BB_dA> | t_BB_dA = t-butylbenzyl-dA |
| Probe 1 | RM_ETP02 | 3 | <Cy5.5>TTCACGGGCCA<BHQ-2>GCTCTTCCGGAACACCGTCCAT<Phos> | <Cy5.5>: Fluorophore <BHQ_2>: Quencher <Phos>: Phosphate |
| Probe 2 | RM_ETP02B | 4 | <Cy5.5>CTGGATCAGGG<BHQ_2>CAACCCAATACTCCACGTTACC<Phos> | <Cy5.5>: Fluorophore <BHQ_2>: Quencher <Phos>: Phosphate |

The detection of bacteria belonging to the Enterobacterales order can also comprise of other primers and probes for amplifying the rplP gene (SEQ ID NOs: 5-7, TABLE II), as well as primers and probes for amplifying the gyrB gene that encodes the DNA gyrase subunit B protein (SEQ ID NOs: 8-10, TABLE III) and primers and probes for amplifying the rpoB gene that encodes the DNA-dependent RNA polymerase (SEQ ID NOs: 11-16, TABLE IV). Representative functional variants can include, e.g., one or more deletions, insertions, and/or substitutions in the target gene primers and probes disclosed herein. More specifically, embodiments of the oligonucleotides each include a nucleic acid with a sequence selected from SEQ ID NOs: 5-7, 8-10, 11-16, a substantially identical variant thereof in which the variant has at least, e.g., 80%, 90%, or 95% sequence identity to one of SEQ ID NOs: 5-7, 8-10, 11-16, or a complement of SEQ ID NOs: 5-7, 8-10, 11-16 and the variant.

TABLE II

Oligonucleotides for detecting Enterobacterales order
Primers and Probes that hybridize to rplP gene in *Enterobacteriaceae/Enterobacterales* strains

| Oligonucleotide Type | Oligonucleotide Name | SEQ ID NO: | Sequence | Modifications |
|---|---|---|---|---|
| Forward primer | SEGP2891 | 5 | AATTCCGTAAAATGCACAAAGGCC | |
| Reverse primer | SEGP2892 | 6 | GCTTAACTGCACGGGTCATAGCA | |
| Probe | SEGP2893 | 7 | <FAM>TGGTCGTCT<ZEN>GACTGCACGTCAGATCGAAGC<3IABkFQ> | <FAM>: Fluorophore <ZEN>: Quencher <3IABkFQ>: 3' Blocker |

TABLE III

Oligonucleotides for detecting Enterobacterales order
Primers and Probes that hybridize to gyrB gene in *Enterobacteriaceae/Enterobacterales* strains

| Oligonucleotide Type | Oligonucleotide Name | SEQ ID NO: | Sequence | Modifications |
|---|---|---|---|---|
| Forward primer | SEGP1899 | 8 | TGTCGAATTCTTATGACTCCTCCAGTA | |
| Reverse primer | SEGP1901 | 9 | CGCGAGCGCTTCGTCGA | |
| Probe | SEGP2016 | 10 | <HEX>CCGGTCTGC<ZEN>ACCACATGGTATTCGAGGTGG | <HEX>: Fluorophore <ZEN>: Quencher |

TABLE III-continued

Oligonucleotides for detecting Enterobacterales order
Primers and Probes that hybridize to gyrB gene in Enterobacteriaceae/
Enterobacterales strains

| Oligonucleotide Type | Oligonucleotide Name | SEQ ID NO: | Sequence | Modifications |
| --- | --- | --- | --- | --- |
| | | | <3IABkFQ> | <3IABkFQ>: 3' Blocker |

TABLE IV

Oligonucleotides for detecting Enterobacterales order
Primers and Probes that hybridize to rpoB gene in Enterobacteriaceae/
Enterobacterales strains

| Oligonucleotide Type | Oligonucleotide Name | SEQ ID NO: | Sequence | Modifications |
| --- | --- | --- | --- | --- |
| Forward primer | SEGP2799 | 11 | TGGTAAACGTCCACAAGTTCTGGA | |
| Reverse primers | SEGP2800 | 12 | CATACTGCCCTTCAGGATCTTGC | |
| | SEGP2802 | 13 | GTAGCTGACATATTGCAGTTCAGCA | |
| | SEGP2821 | 14 | CCGTTCTGACCGTCCGGATC | |
| Probes | SEGP2804 | 15 | <FAM>TATCTCCTT<ZEN>TCTA TCCAGCTTGACTCGTTTC AGA AGTTTATCGA<3IABkFQ> | <FAM>: Fluorophore <ZEN>: Quencher <3IABkFQ>: 3' Blocker |
| | SEGP2822 | 16 | <FAM>TC TCC TTTC<ZEN>T ATCCAGCTGGATTCATTC CAG AAATTCATTGAAC<3IABkFQ> | |

For detection of bacteria belonging to the species *Acinetobacter baumannii* (Abi), primers and probes for amplifying the ompA gene encoding for the outer membrane protein A are provided (see TABLE V). Nucleic acids other than those exemplified herein can also be used to detect *Acinetobacter* genus-specific pathogen grouping target genes in a sample. For example, functional variants can be evaluated for specificity and/or sensitivity by those of skill in the art using routine methods. Representative functional variants can include, e.g., one or more deletions, insertions, and/or substitutions in the target gene primers and probes disclosed herein. More specifically, embodiments of the oligonucleotides each include a nucleic acid with a sequence selected from SEQ ID NOs: 17-19, 20-22, 29-31 a substantially identical variant thereof in which the variant has at least, e.g., 80%, 90%, or 95% sequence identity to one of SEQ ID NOs:17-19, 20-22, 29-31 or a complement of SEQ ID NOs: 17-19, 20-22, 29-31 and the variant.

TABLE V

Oligonucleotides for detecting *Acinetobacter baumannii*
Primers and Probes that hybridize to ompA gene in *A. baumannii*

| Oligonucleotide Type | Oligonucleotide Name | SEQ ID NO: | Sequence | Modifications |
| --- | --- | --- | --- | --- |
| Forward primer | RM_AFP01 | 17 | TTGGTGGTCACTTGAAG<t_BB_dC> | t_BB_dC = t-butylbenzyl-dC |
| Reverse primer | RM_ARP02 | 18 | TTTCTGGCTTGTATTGGT<t_BB_dC> | t_BB_dC = t-butylbenzyl-dC |
| Probe | RM_P02 | 19 | <HEX_Thr>ACTCCAG<BHQ_2>T TGCTCCACAACCACAAGAG<Phos> | <HEX_Thr>: Fluorophore <BHQ_2>: Quencher <Phos>: Phosphate |
| Forward primer | SEGP2603 | 20 | TTATCTTTAGCTCGTGCTAACTC TGTTAAA | |
| Reverse primer | SEGP2606 | 21 | GCACGACCTTCTTTAGTTTTGTT GTCA | |
| Probe | SEGP2769 | 22 | <ATTO>TCTACTCA<BHQ_2>AG GTTTCGCTTGGGATCAACCGAT TGCT<Phos> | <ATTO>: Fluorophore <BHQ_2>: Quencher <Phos>: Phosphate |

TABLE V-continued

Oligonucleotides for detecting Acinetobacter baumannii
Primers and Probes that hybridize to ompA gene in A. baumannii

| Oligonucleotide Type | Oligonucleotide Name | SEQ ID NO: | Sequence | Modifications |
|---|---|---|---|---|
| Forward primer | SEGP1813 | 29 | ACCCTAACGCTACTGCACGT | |
| Reverse primer | SEGP1815 | 30 | GGTTGATCCCAAGCGAAACCT | |
| Probe | SEGP1951 | 31 | <ATTO>TCGAAGGT<BHQ_2>CACACAGATAACACT<Phos> | <ATTO>: Fluorophore <BHQ_2>: Quencher <Phos>: Phosphate |

The detection of *Acinetobacter baumannii* can also comprise of primers and probes for amplifying the rpoB gene (SEQ ID NOs:23-25, TABLE VI) and for amplifying the gyrB gene (SEQ ID NOs:26-28, TABLE VII). Representative functional variants can include, e.g., one or more deletions, insertions, and/or substitutions in the target gene primers and probes disclosed herein. More specifically, embodiments of the oligonucleotides each include a nucleic acid with a sequence selected from SEQ ID NOs:23-25, 26-28, a substantially identical variant thereof in which the variant has at least, e.g., 80%, 90%, or 95% sequence identity to one of SEQ ID NOs: 23-25, 26-28, or a complement of SEQ ID NOs: 23-25, 26-28, and the variant.

For detection of bacteria belonging to the species *Pseudomonas aruginosa* (Pae), primers and probes for amplifying the tuf gene encoding elongation factor (SEQ ID NOs: 32-34, TABLE VIII), the gyrB gene (SEQ ID NOs: 35-37, TABLE IX) and the rpoB gene (SEQ ID NOs: 38-40, TABLE X) are provided. Nucleic acids other than those exemplified herein can also be used to detect *Pseudomonas* genus-specific pathogen grouping target genes in a sample. For example, functional variants can be evaluated for specificity and/or sensitivity by those of skill in the art using routine methods. Representative functional variants can include, e.g., one or more deletions, insertions, and/or substitutions in the target gene primers and probes disclosed

TABLE VI

Oligonucleotides for detecting Acinetobacter baumannii
Primers and Probes that hybridize to rpoB gene in Acinetobacter baumannii

| Oligonucleotide Type | Oligonucleotide Name | SEQ ID NO: | Sequence | Modifications |
|---|---|---|---|---|
| Forward primer | SEGP2590 | 23 | CATACTCATATACCGAAAAGAAACGG | |
| Reverse primer | SEGP2593 | 24 | CTATACTCAACAAATTCTAAAGCAGC | |
| Probe | SEGP2594 | 25 | <FAM>CGCGAAGAT<ZEN>ATCGGTCTCC<3IABkFQ> | <FAM>: Fluorophore <ZEN>: Quencher <3IABkFQ>: 3' Blocker |

TABLE VII

Oligonucleotides for detecting Acinetobacter baumannii
Primers and Probes that hybridize to gyrB gene in Acinetobacter baumannii

| Oligonucleotide Type | Oligonucleotide Name | SEQ ID NO: | Sequence | Modifications |
|---|---|---|---|---|
| Forward primer | SEGP2626 | 26 | ACAGAACAAACCAATGAAAAGGCTTATGATTC | |
| Reverse primer | SEGP2628 | 27 | ACCATATGGTGTAAACCGGTACC | |
| Probe | SEGP2629 | 28 | <FAM>AAAGTATTA<ZEN>CGTGATTAGATGCAGTTCGTAAACGTCCGGGT<3IABkFQ> | <FAM>: Fluorophore <ZEN>: Quencher <3IABkFQ>: 3' Blocker | herein. More specifically, embodiments of the oligonucleotides each include a nucleic acid with a sequence selected from SEQ ID NOs: 32-34, 35-37, 38-40, a substantially identical variant thereof in which the variant has at least, e.g., 80%, 90%, or 95% sequence identity to one of SEQ ID NOs: 32-34, 35-37, 38-40, or a complement of SEQ ID NOs: 32-34, 35-37, 38-40 and the variant.

pathogen grouping target genes in a sample. For example, functional variants can be evaluated for specificity and/or sensitivity by those of skill in the art using routine methods. Representative functional variants can include, e.g., one or more deletions, insertions, and/or substitutions in the target gene primers and probes disclosed herein. More specifically,

TABLE VIII

Oligonucleotides for detecting *Pseudomonas aeruginosa*
Primers and Probes that hybridize to tuf gene in *Pseudomonas aeruginosa*

| Oligonucleotide Type | Oligonucleotide Name | SEQ ID NO: | Sequence | Modifications |
|---|---|---|---|---|
| Forward primer | SEGP2341 | 32 | CCGTGCAGAAGCTGGTAG | |
| Reverse primer | SEGP2342 | 33 | GAGATCGAGAACACGTCTTCG | |
| Probe | SEGP2343 | 34 | <FAM>TTCCGGAGC<ZEN>CGGTTCGT GCCATCG<3IABkFQ> | <FAM>: Fluorophore <ZEN>: Quencher <3IABkFQ>: 3' Blocker |

TABLE IX

Oligonucleotides for detecting *Pseudomonas aeruginosa*
Primers and Probes that hybridize to gyrB gene in *Pseudomonas aeruginosa*

| Oligonucleotide Type | Oligonucleotide Name | SEQ ID NO: | Sequence | Modifications |
|---|---|---|---|---|
| Forward primer | SEGP2630 | 35 | GGAGTACAACATCGACAAGCTGC | |
| Reverse primer | SEGP2631 | 36 | CGCTCGATCAGCTCGGGC | |
| Probe | SEGP2632 | 37 | <FAM>CACAACATC<ZEN>ATCATCAT GACCGATGCTGACGTCGAC<3IABkFQ> | <FAM>: Fluorophore <ZEN>: Quencher <3IABkFQ>: 3' Blocker |

TABLE X

Oligonucleotides for detecting *Pseudomonas aeruginosa*
Primers and Probes that hybridize to rpoB gene in *Pseudomonas aeruginosa*

| Oligonucleotide Type | Oligonucleotide Name | SEQ ID NO: | Sequence | Modifications |
|---|---|---|---|---|
| Forward primer | SEGP2634 | 38 | GGCGTGCTGAAGATCGTCAA | |
| Reverse primer | SEGP2637 | 39 | ACCGGCATGATCACCGAGA | |
| Probe | SEGP2640 | 40 | <FAM>CGCATCCAG<ZEN>CCGGGCGA CAAGATGG<3IABkFQ> | <FAM>: Fluorophore <ZEN>: Quencher <3IABkFQ>: 3' Blocker |

For detection of bacteria belonging to the species *Strenotrophomonas maltophilia* (*S. maltophilia*), primers and probes for amplifying the fdnG gene (SEQ ID NOs: 41-43, TABLE XI), the gyrB gene (SEQ ID NOs: 44-46, TABLE XII) and the tuf gene (SEQ ID NOs: 47-49, TABLE XIII) are provided. Nucleic acids other than those exemplified herein can also be used to detect *Strenotrophomonas* genus-specific embodiments of the oligonucleotides each include a nucleic acid with a sequence selected from SEQ ID NOs: 41-43, 44-46, 47-49, a substantially identical variant thereof in which the variant has at least, e.g., 80%, 90%, or 95% sequence identity to one of SEQ ID NOs: 41-43, 44-46, 47-49, or a complement of SEQ ID NOs: 41-43, 44-46, 47-49, and the variant.

TABLE XI

Oligonucleotides for detecting *Strenotrophomonas maltophilia*
Primers and Probes that hybridize to fdnG gene in *Strenotrophomonas maltophilia*

| Oligonucleotide Type | Oligonucleotide Name | SEQ ID NO: | Sequence | Modifications |
|---|---|---|---|---|
| Forward primer | SEGP2532 | 41 | CCAAGCTCGACAAGCCGTAC | |
| Reverse primer | SEGP2538 | 42 | GCTTGGAGAACGCGCTGATC | |
| Probe | SEGP2544 | 43 | \<FAM>TGCAGGCGT\<ZEN>ACGAGCTGATGAACGAAGGC\<3IABkFQ> | \<FAM>: Fluorophore  \<ZEN>: Quencher  \<3IABkFQ>: 3' Blocker |

TABLE XII

Oligonucleotides for detecting *Strenotrophomonas maltophilia*
Primers and Probes that hybridize to gyrB gene in *Strenotrophomonas maltophilia*

| Oligonucleotide Type | Oligonucleotide Name | SEQ ID NO: | Sequence | Modifications |
|---|---|---|---|---|
| Forward primer | SEGP2578 | 44 | TGCAGTGGACCGACTCCTA | |
| Reverse primer | SEGP2579 | 45 | CTGCTTGGCGATGCCGTTCT | |
| Probe | SEGP2580 | 46 | \<FAM>GACGATGTA\<ZEN>CTGCTTCACCAAC\<3IABkFQ> | \<FAM>: Fluorophore  \<ZEN>: Quencher  \<3IABkFQ>: 3' Blocker |

TABLE XIII

Oligonucleotides for detecting *Strenotrophomonas maltophilia*
Primers and Probes that hybridize to tuf gene in *Strenotrophomonas maltophilia*

| Oligonucleotide Type | Oligonucleotide Name | SEQ ID NO: | Sequence | Modifications |
|---|---|---|---|---|
| Forward primer | SEGP2572 | 47 | GCACCAAGCCGCACGTCA | |
| Reverse primer | SEGP2573 | 48 | GTGCGCGGTCGAGATCGT | |
| Probe | SEGP2574 | 49 | \<FAM>CAAGACCAC\<ZEN>GCTGACCGC\<3IABkFQ> | \<FAM>: Fluorophore  \<ZEN>: Quencher  \<3IABkFQ>: 3' Blocker |

For detection of bacteria belonging to the *Enterococcus* genus, primers and probes for amplifying the tuf gene (SEQ ID NOs: 50-52, TABLE XIV), the rpoB gene (SEQ ID NOs: 53-55, TABLE XV), the ddl gene encoding xxxx (SEQ ID NOs: 56-61, TABLE XVI), and the gyrB gene (SEQ ID NOs: 62-66, TABLE XVII) are provided. Nucleic acids other than those exemplified herein can also be used to detect *Enterococcus* genus-specific pathogen grouping target genes in a sample. For example, functional variants can be evaluated for specificity and/or sensitivity by those of skill in the art using routine methods. Representative functional variants can include, e.g., one or more deletions, insertions, and/or substitutions in the target gene primers and probes disclosed herein. More specifically, embodiments of the oligonucleotides each include a nucleic acid with a sequence selected from SEQ ID NOs: 50-52, 53-55, 56-61, 62-66, a substantially identical variant thereof in which the variant has at least, e.g., 80%, 90%, or 95% sequence identity to one of SEQ ID NOs: 50-52, 53-55, 56-61, 62-66, or a complement of SEQ ID NOs: 50-52, 53-55, 56-61, 62-66 and the variant.

TABLE XIV

Oligonucleotides for detecting *Enterococcus* genus
Primers and Probes that hybridize to tuf gene in *Enterococcus* genus

| Oligonucleotide Type | Oligonucleotide Name | SEQ ID NO: | Sequence | Modifications |
|---|---|---|---|---|
| Forward primer | SEGP1632 | 50 | GACAAACCATTCATGATGCCAG | |

TABLE XIV-continued

Oligonucleotides for detecting *Enterococcus* genus
Primers and Probes that hybridize to tuf gene in *Enterococcus* genus

| Oligonucleotide Type | Oligonucleotide Name | SEQ ID NO: | Sequence | Modifications |
|---|---|---|---|---|
| Reverse primer | SEGP1631 | 51 | AACTTCGTCACCAACGCGAAC | |
| Probe | SEGP1633 | 52 | \<HEX\>CTGGACGTG\<ZEN\>GTA CTGTTGCTAC\<3IABkFQ\> | \<HEX\>: Fluorophore \<ZEN\>: Quencher \<3IABkFQ\>: 3' Blocker |

TABLE XV

Oligonucleotides for detecting *Enterococcus* genus
Primers and Probes that hybridize to rpoB gene in *Enterococcus* genus

| Oligonucleotide Type | Oligonucleotide Name | SEQ ID NO: | Sequence | Modifications |
|---|---|---|---|---|
| Forward primer | SEGP2522 | 53 | CCGTCCAGTGGTAGCAAGTAT CA | |
| Reverse primer | SEGP2525 | 54 | ACCATAGTGAGAGTAGTGAAC GTCA | |
| Probe | SEGP2770 | 55 | \<HEX\>TTGACTCGT\<ZEN\>GAC CGTGCCGGTTATGAAGTTCG \<3IABkFQ\> | \<HEX\>: Fluorophore \<ZEN\>: Quencher \<3IABkFQ\>: 3' Blocker |

TABLE XVI

Oligonucleotides for detecting *Enterococcus* genus
Primers and Probes that hybridize to ddl gene in *Enterococcus* genus

| Oligonucleotide Type | Oligonucleotide Name | SEQ ID NO: | Sequence | Modifications |
|---|---|---|---|---|
| Forward primer | SEGP1624 | 56 | CGTAGCATTCTATGATTATGAAGC C | |
| | SEGP1627 | 57 | GACAGGAAAGAAACTAGGAGGAC | |
| Reverse primer | SEGP1625 | 58 | CATCGTGTAAGCTAACTTCG | |
| | SEGP1628 | 59 | AAACAGACACATCGTGCT | |
| Probe | SEGP1626 | 60 | \<HEX\>CAGATTCCA\<ZEN\>GCCGAA GTGCC\<3IABkFQ\> | \<HEX\>: Fluorophore \<ZEN\>: Quencher \<3IABkFQ\>: 3' Blocker |
| | SEGP1629 | 61 | \<HEX\>CACTTCTGC\<ZEN\>CGCCAT ACAACAA\<3IABkFQ\> | |

TABLE XVII

Oligonucleotides for detecting *Enterococcus* genus
Primers and Probes that hybridize to gyrB gene in *Enterococcus* genus

| Oligonucleotide Type | Oligonucleotide Name | SEQ ID NO: | Sequence | Modifications |
|---|---|---|---|---|
| Forward primer | SEGP2882 | 62 | AGCAACGATCCTGAAAAATGCGA ATTGTTCATC | |
| | SEGP2884 | 63 | AGTAAAGATCCGGAAAAATGCGA ATTATTTATC | |
| Reverse primer | SEGP2885 | 64 | AAAGACCGGATCTCTTCATTTGCC | |
| | SEGP2886 | 65 | AATGACCGAATTTCTTCATTGGCT | |

TABLE XVII-continued

Oligonucleotides for detecting *Enterococcus* genus
Primers and Probes that hybridize to gyrB gene in *Enterococcus* genus

| Oligonucleotide Type | Oligonucleotide Name | SEQ ID NO: | Sequence | Modifications |
|---|---|---|---|---|
| Probe | SEGP2888 | 66 | \<FAM>CCAATTCGT\<ZEN>GGGAA AATCTTGAATGTTGAGAAAGCAAG CA\<3IABkFQ> | \<FAM>: Fluorophore \<ZEN>: Quencher \<3IABkFQ>: 3' Blocker |

For detection of bacteria belonging to the species *Staphylococcus aureus* (*S. aureus*), primers and probes for amplifying the CPE gene encoding a protein involved in capsular formation (SEQ ID NOs: 67-69, 72 TABLE XVIII), the gyrB gene (SEQ ID NOs: 73-75, TABLE XIX), the ddlA gene (SEQ ID NOs: 76-78, TABLE XX). For detection of bacteria belonging to the *Staphylococcus* genus, primers and probes for amplifying the tuf gene (SEQ ID NOs: 79-81, TABLE XXII) are provided. Nucleic acids other than those exemplified herein can also be used to detect *Staphylococcus* genus-specific pathogen grouping target genes in a sample. For example, functional variants can be evaluated for specificity and/or sensitivity by those of skill in the art using routine methods. Representative functional variants can include, e.g., one or more deletions, insertions, and/or substitutions in the target gene primers and probes disclosed herein. More specifically, embodiments of the oligonucleotides each include a nucleic acid with a sequence selected from SEQ ID NOs: 67-69, 72, 73-75, 76-78, 79-81, a substantially identical variant thereof in which the variant has at least, e.g., 80%, 90%, or 95% sequence identity to one of SEQ ID NOs: 67-69, 72, 73-75, 76-78, 79-81, or a complement of SEQ ID NOs: 67-69, 72, 73-75, 76-78, 79-81 and the variant.

TABLE XVIII

Oligonucleotides for detecting *Staphylococcus aureus*
Primers and Probes that hybridize to CPE gene in *Staphylococcus aureus*

| Oligonucleotide Type | Oligonucleotide Name | SEQ ID NO: | Sequence | Modifications |
|---|---|---|---|---|
| Forward primer | SEGP1490 | 67 | AAGATAAGCTTATTGAACAAGG ACATC | |
| Reverse primer | SEGP1491 | 68 | CTTGAGGTGAATTGTTGTGAAC C | |
| Probe | SEGP1492 | 72 | \<FAM>TTAGGAATC\<ZEN>AATT ATGGAA GTCGACCTCGT\<3IABkFQ> | \<FAM>: Fluorophore \<ZEN>: Quencher \<3IABkFQ>: 3' Blocker |
| Probe | SEGP1493 | 69 | \<HEX>TTAGGAATC\<ZEN>AATT ATGGAAGTCGACCTCGT\<3IABkFQ> | \<HEX>: Fluorophore \<ZEN>: Quencher \<3IABkFQ>: 3' Blocker |

TABLE XIX

Oligonucleotides for detecting *Staphylococcus aureus*
Primers and Probes that hybridize to gyrB gene in *Staphylococcus aureus*

| Oligonucleotide Type | Oligonucleotide Name | SEQ ID NO: | Sequence | Modifications |
|---|---|---|---|---|
| Forward primer | SEGP2792 | 73 | CACAAGTCGCACGTACAGTG | |
| Reverse primer | SEGP2793 | 74 | ATTCTTCAGGACTTTTACTAGA GCAATCG | |
| Probe | SEGP2794 | 75 | \<FAM>TAAATCAGC\<ZEN>GTT AGATGTAGCAAGTC\<3IABkFQ> | \<FAM>: Fluorophore \<ZEN>: Quencher \<3IABkFQ>: 3' Blocker |

TABLE XX

Oligonucleotides for detecting *Staphylococcus aureus*
Primers and Probes that hybridize to ddlA gene in *Staphylococcus aureus*

| Oligonucleotide Type | Oligonucleotide Name | SEQ ID NO: | Sequence | Modifications |
|---|---|---|---|---|
| Forward primer | SEGP2932 | 76 | ATCTACTGATGAGCTTCATTTAGAAAATGGA | |
| Reverse primer | SEGP2933 | 77 | TCAAAAAGTCCTTGAATCGTGCCA | |
| Probe | SEGP2935 | 78 | <FAM>CGCTTGAGA<ZEN>TTTCACAGCTATTGAAAGAAAGTAGTTCAGGACAA<3IABkFQ> | <FAM>: Fluorophore<br><ZEN>: Quencher<br><3IABkFQ>: 3' Blocker |

TABLE XXI

Oligonucleotides for detecting *Staphylococcus* Genus
Primers and Probes that hybridize to tuf gene in *Staphylococcus* genus

| Oligonucleotide Type | Oligonucleotide Name | SEQ ID NO: | Sequence | Modifications |
|---|---|---|---|---|
| Forward primer | SEGP1835 | 79 | CCGTGTTGAACGTGGTCAAATCAAA | |
| Reverse primer | SEGP1836 | 80 | AGCAGCTAATACTTGACCACGTTGTA | |
| Probe | SEGP1838 | 81 | <FAM>AGACTACGC<ZEN>TGAAGCTGGTGAC<3IABkFQ> | <FAM>: Fluorophore<br><ZEN>: Quencher<br><3IABkFQ>: 3' Blocker |

For detection of bacteria belonging to the species *Streptococcus agalactiae* (*S. agalactiae*), primers and probe for amplifying the gyrB gene (SEQ ID NOs: 121-123, TABLE XXII), the sip gene encoding the surface immunogenic protein (SEQ ID NOs: 82-84, TABLE XXIII), and the ddlA gene (SEQ ID NOs: 85-87, TABLE XXIV) are provided. For detection of bacteria belonging to the *Streptococcus* genus, primers and probes for amplifying the tuf gene (SEQ ID NOs: 100-102, TABLE XXV) are provided. Nucleic acids other than those exemplified herein can also be used to detect *Streptococcus* genus-specific pathogen grouping target genes in a sample. For example, functional variants can be evaluated for specificity and/or sensitivity by those of skill in the art using routine methods. Representative functional variants can include, e.g., one or more deletions, insertions, and/or substitutions in the target gene primers and probes disclosed herein. More specifically, embodiments of the oligonucleotides each include a nucleic acid with a sequence selected from SEQ ID NOs: 121-123, 82-84, 85-87, 100-102 a substantially identical variant thereof in which the variant has at least, e.g., 80%, 90%, or 95% sequence identity to one of SEQ ID NOs: 121-123, 82-84, 85-87, 100-102 or a complement of SEQ ID NOs: 121-123, 82-84, 85-87, 100-102 and the variant.

TABLE XXII

Oligonucleotides for detecting *Streptococcus agalactiae*
Primers and Probes that hybridize to gyrB gene in *Streptococcus agalactiae*

| Oligonucleotide Type | Oligonucleotide Name | SEQ ID NO: | Sequence | Modifications |
|---|---|---|---|---|
| Forward primer | SEGP2921 | 121 | ACCACTGTATTTGATTTTGATAAATTAGCCAAA | |
| Reverse primer | SEGP2922 | 122 | TTCTCATTGATAAACTCAACGTATGAACCTA | |
| Probe | SEGP2923 | 123 | <FAM>ACTAAGAAT<ZEN>CTCCATTTCAGACAAGCGAGAAGGTCAAGAAGTTG<3IABkFQ> | <FAM>: Fluorophore<br><ZEN>: Quencher<br><3IABkFQ>: 3' Blocker |

TABLE XXIII

Oligonucleotides for detecting *Streptococcus agalactiae*
Primers and Probes that hybridize to sip gene in *Streptococcus agalactiae*

| Oligonucleotide Type | Oligonucleotide Name | SEQ ID NO: | Sequence | Modifications |
|---|---|---|---|---|
| Forward primer | SEGP2204 | 82 | ATCCTGAGACAACACTGACA | |
| Reverse primer | SEGP2205 | 83 | TTGCTGGTGTTTCTATTTTCA | |
| Probe | SEGP2206 | 84 | <CY5.5>ATCAGAAGAGT<BHQ_2>CATACTGCCACTTC<Phos> | <CY5.5>: Fluorophore <BHQ_2>: Quencher <Phos>: Phosphate |

TABLE XXIV

Oligonucleotides for detecting *Streptococcus agalactiae*
Primers and Probes that hybridize to ddlA gene in *Streptococcus agalactiae*

| Oligonucleotide Type | Oligonucleotide Name | SEQ ID NO: | Sequence | Modifications |
|---|---|---|---|---|
| Forward primer | SEGP2947 | 85 | CACAAGAATTTGATGAAATGCCATCTTCA | |
| Reverse primer | SEGP2949 | 86 | ACAATTGCATTATCATCATAGATATCACTTGGA | |
| Probe | SEGP2951 | 87 | <FAM>TAATGACAA<ZEN>ACCAAACTGTTGATTTAGACAAAATGGTTCGTCCA<3IABkFQ> | <FAM>: Fluorophore <ZEN>: Quencher <3IABkFQ>: 3' Blocker |

TABLE XXV

Oligonucleotides for detecting *Streptococcus* Genus
Primers and Probes that hybridize to tuf gene in *Streptococcus* genus

| Oligonucleotide Type | Oligonucleotide Name | SEQ ID NO: | Sequence | Modifications |
|---|---|---|---|---|
| Forward primer | SEGP1705 | 100 | GTACAGTTGCTTCAGGACGTATC | |
| Reverse primer | SEGP1706 | 101 | ACGTTCGATTTCATCACGTTG | |
| Probe | SEGP1709.1 | 102 | <ATTO>TTCCGTA<BHQ_2>AACAACTTGACGAAGGTCTTG<Phos> | <ATTO>: Fluorophore <ZEN>: Quencher <Phos>: Phosphate |

For detection of the common fungal pathogens: *Candida albicans* and *Candida auris*, primers and probe for amplifying the 18 s ribosomal RNA (18 s rRNA) gene (SEQ ID NOs: 88-90, TABLE XXVI), and the 5.8 s ribosomal RNA (5.8 s rRNA) gene (SEQ ID NOs: 91-93, TABLE XXVII) are provided. Nucleic acids other than those exemplified herein can also be used to detect *Candida* genus-specific pathogen grouping target genes in a sample. For example, functional variants can be evaluated for specificity and/or sensitivity by those of skill in the art using routine methods. Representative functional variants can include, e.g., one or more deletions, insertions, and/or substitutions in the target gene primers and probes disclosed herein. More specifically, embodiments of the oligonucleotides each include a nucleic acid with a sequence selected from SEQ ID NOs: 88-90, 91-93, a substantially identical variant thereof in which the variant has at least, e.g., 80%, 90%, or 95% sequence identity to one of SEQ ID NOs: 88-90, 91-93, or a complement of SEQ ID NOs: 88-90, 91-93 and the variant.

TABLE XXVI

Oligonucleotides for detecting *Candida*
Primers and Probes that hybridize to 18s rRNA gene in *Candida*

| Oligonucleotide Type | Oligonucleotide Name | SEQ ID NO: | Sequence | Modifications |
|---|---|---|---|---|
| Forward primer | SEGP1712 | 88 | CGTTTTCATTAATCAAGAACGAAAGTTA | |
| Reverse primer | SEGP1713 | 89 | ACCGATCCCTAGTCGGCATA | |
| Probe | SEGP1716 | 90 | \<FAM>AGACTACGA\<ZEN>CGGTATCTGATCATCTTCGATCCC\<3IABkFQ> | \<FAM>: Fluorophore  \<ZEN>: Quencher  \<3IABkFQ>: 3' Blocker |

TABLE XXVII

Oligonucleotides for detecting *Candida*
Primers and Probes that hybridize to 5.8s rRNA gene in *Candida*

| Oligonucleotide Type | Oligonucleotide Name | SEQ ID NO: | Sequence | Modifications |
|---|---|---|---|---|
| Forward primer | SEGP1718 | 91 | ACAACGGATCTCTTGGTTCTC | |
| Reverse primer | SEGP1719 | 92 | GCAATGTGCGTTCAAAGATTCGA | |
| Probe | SEGP1722.1 | 93 | \<FAM_Thr>TCGATGAAG\<BHQ_2>AACGCAGCGAAATGCGATACG\<Phos> | \<FAM_Thr>: Fluorophore  \<BHQ_2>: Quencher  \<Phos>: Phosphate |

For detection of all types of bacteria, a primer and probe combination for amplifying a conserved region in the 16 s ribosomal RNA (16 s rRNA) gene (SEQ ID NOs: 94-96, TABLE XXVIII) is provided.

TABLE XXVIII

Oligonucleotides for detecting general bacteria
Primers and Probes that hybridize to 16s rRNA in bacteria (Gram-positive and Gram-negative)

| Oligonucleotide Type | Oligonucleotide Name | SEQ ID NO: | Sequence | Modifications |
|---|---|---|---|---|
| Forward primer | SEGP1830 | 94 | TCCTACGGGAGGCAGCAGT | |
| Reverse primer | SEGP1831 | 95 | GGACTACCAGGGTATCTAATCCTGTT | |
| Probe | SEGP1895.1 | 96 | \<CFR_635>CGTATTACCGCGGCT\<BHQ_2>GCTGGCAC\<Phos> | \<CFR_635>: Fluorophore  \<BHQ_2>: Quencher  \<Phos>: Phosphate |

In one embodiment, the above-described sets of primers and probes are used not only for the detection and for identification of infectious bacteria strains but also in the performance of an antimicrobial susceptibility testing (AST) assay. Therefore, the present invention discloses methods and compositions for performing quantitative real-time PCR reactions whereby identification (ID) of bacteria and testing of their antimicrobial susceptibility (AST) are determined simultaneously at a single assay setting.

A functionally active variant of any of the primers and/or probes disclosed herein may be identified by using the primers and/or probes in the disclosed methods. A functionally active variant of a primer and/or probe described herein pertains to a primer and/or probe that provide a similar or higher specificity and sensitivity in the described method or kit as compared to the respective sequence of the primer and/or probe described herein.

The variant may, e.g., vary from the sequence of the primers and probes described herein by one or more nucleotide additions, deletions or substitutions such as one or more nucleotide additions, deletions or substitutions at the 5' end and/or the 3' end of the respective sequence of the primer and/or probe described herein. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-deazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding any of the target genes can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length). In some embodiments oligonucleotide primers are 40 or fewer nucleotides in length.

In addition to a set of primers, the methods may use one or more probes in order to detect the presence or absence of target genes. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a target gene nucleic acid. A "probe" can be referred to as a "detection probe" meaning that it detects the target nucleic acid.

In some embodiments, the described target gene probes can be labeled with at least one fluorescent label. In one embodiment, the target gene probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of the probe sequences disclosed herein.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length.

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described target gene nucleic acid sequences. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the described target gene nucleic acid molecules. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ nucleic acid such as RNA or DNA (cDNA). The template nucleic acid need not be purified; it may be a minor fraction of a complex mixture, such as nucleic acid contained in human cells. Nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, protozoa viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 µg protodenatured template DNA, 50 pmoles of each oligonucleotide primer, 2.5 U of Taq polymerase, and 10% DMSO). The reactions usually contain 150 to 320 M each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, a oligonucleotide probe can contain a donor fluorescent moiety and a corresponding quencher, which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced there between.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimidyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide which contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

As described herein, amplification products can be detected using labeled hybridization probes that take advantage of FRET technology. One FRET format utilizes TaqMan® technology to detect the presence or absence of an amplification product, and hence, the presence or absence of the target gene. TaqMan® technology utilizes one single-stranded hybridization probe labeled with, e.g., one fluorescent dye and one quencher, which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of the target gene in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of target strain/family genomes). If amplification of target nucleic acid occurs and an amplification product is produced, the step of hybridizing results in a detectable signal based upon FRET between the members of the pair of probes.

Generally, the presence of FRET indicates the presence of the target gene in the sample, and the absence of FRET indicates the absence of the target gene in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of the presence of the target strain/family of interest.

Representative biological samples that can be used in practicing the methods include, but are not limited to respiratory specimens, fecal specimens, blood specimens, dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release target gene nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the probes from the amplification products can confirm the presence or absence of the target strain/family of interest in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

It is understood that the embodiments of the present disclosure are not limited by the configuration of one or more commercially available instruments.

Real-Time PCR for Phenotypic Antimicrobial Susceptibility Testing (AST)

Although quantitative real-time PCR (qPCR or qRT-PCR) can identify and quantify bacteria in samples with high specificity and sensitivity, its reliability in performing phenotypic based AST using growth of bacteria in the presence of antimicrobials has not been demonstrated with consistency. The present invention utilizes mathematical relationships derived from PCR growth curves to make the determination of whether a tested bacteria strain is susceptible, intermediate or resistant (SIR) to a given antimicrobial. The principle behind a phenotypic AST test using PCR is depicted in FIG. 1. In the absence of antimicrobial (shown as Reference), bacteria have ongoing genomic DNA replication. In the presence of an antimicrobial, resistant bacteria will replicate with similar number of genome copies as the Reference, while susceptible bacteria will experience inhibition of replication resulting in fewer copies. This difference in growth provides a phenotypic readout that can be determined by qPCR.

Figure 3:
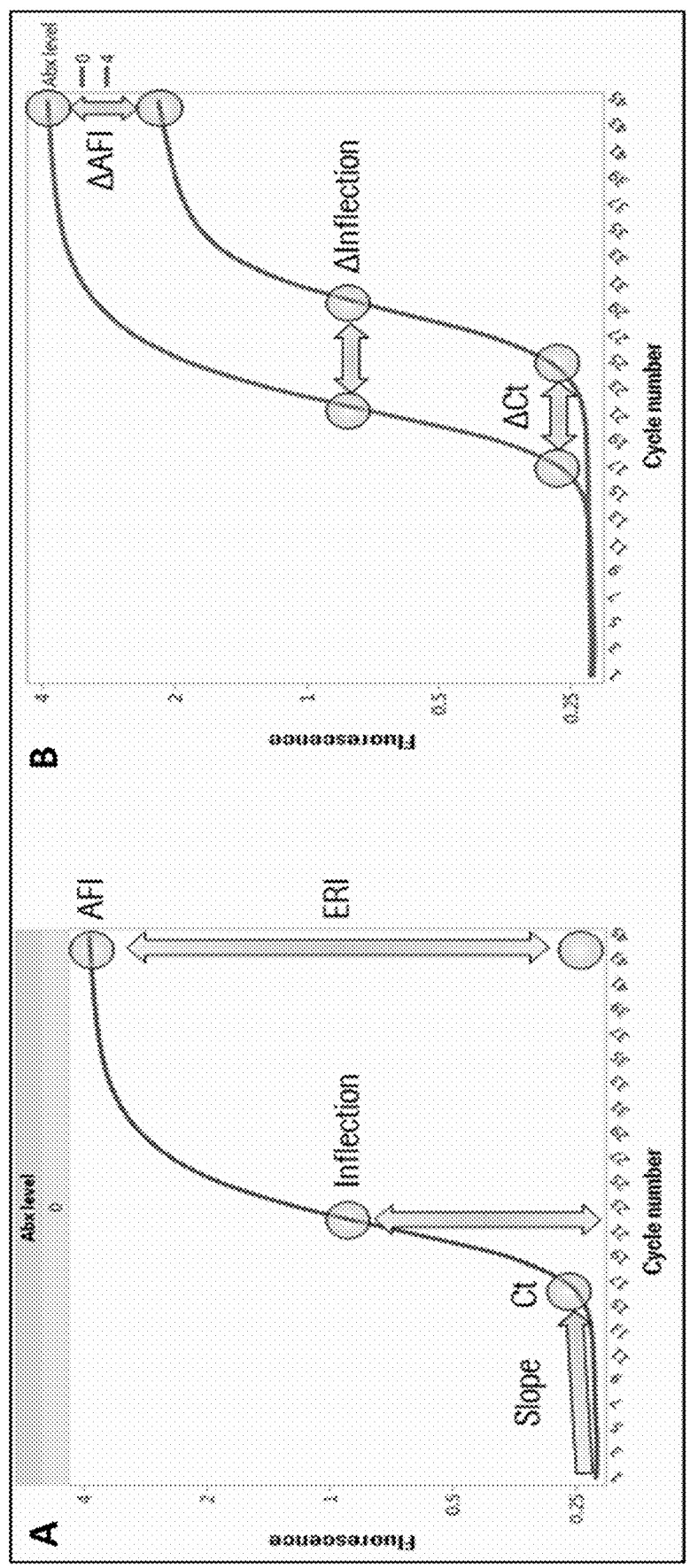
FIG. 3. A Mathematical relationships such as "Slope", "Ct", "Inflection", "Absolute Fluorescence Intensity (AFI)", and "Endpoint Relative Intensity (ERI)" describe the behavior of the raw qPCR amplification curve. B These features can further be evaluated as a function of antimicrobial exposure by relating numerical values obtained in the presence of antimicrobial back to the numerical values obtained in the absence of the antimicrobial. Relative changes in these features, such as "$\Delta Ct$", "$\Delta$Inflection" or "$\Delta$AFI" can then be used to determine strain MIC to a given drug allowing strain resistance and susceptibility determination utilizing approved breakpoints.

Raw data from a hypothetical qPCR experiment in which either a resistant or a susceptible bacteria strain is incubated for four hours with various concentrations of an antimicrobial shown in FIG. 2. In FIG. 2A, the raw qPCR data is depicted as growth curves where fluorescence (e.g. from a TaqMan probe) is measured at each PCR cycle. For the resistant isolate, the growth curve appears similar irrespective of incubation for four hours at different antimicrobial concentrations, whereas in the susceptible isolate, a dose-dependent decrease in fluorescent intensity and increase in the number of cycles required for the signal to cross background (threshold) level, which is commonly referred as the Cycle threshold or Ct value. In FIG. 2B the same qPCR data is represented based on the Ct value, where a resistant isolate has little or no change in Ct value as a function of antimicrobial concentration, while a susceptible isolate has a dose dependent increase in Ct value by detecting a smaller number of replicating bacteria.

qPCR data can be used to determine whether a strain is susceptible, intermediate or resistant to a given antimicrobial by exploring a variety of mathematical relationships that are shown on FIG. 3. FIG. 3A describes mathematical relationships such as "Slope", "Ct", "Inflection", "Absolute Fluorescence Intensity (AFI)", and "Endpoint Relative Intensity (ERI)" describe the behavior of the raw qPCR amplification curve. As shown in FIG. 3B, these features can further be evaluated as a function of antimicrobial exposure by relating numerical values obtained in the presence of antimicrobial back to the numerical values obtained in the absence of the antimicrobial. Relative changes in these features, such as ΔCt or ΔAFI can then be used to determine strain MIC to a given drug allowing strain resistance and susceptibility determination utilizing approved breakpoints.

Figure 4:
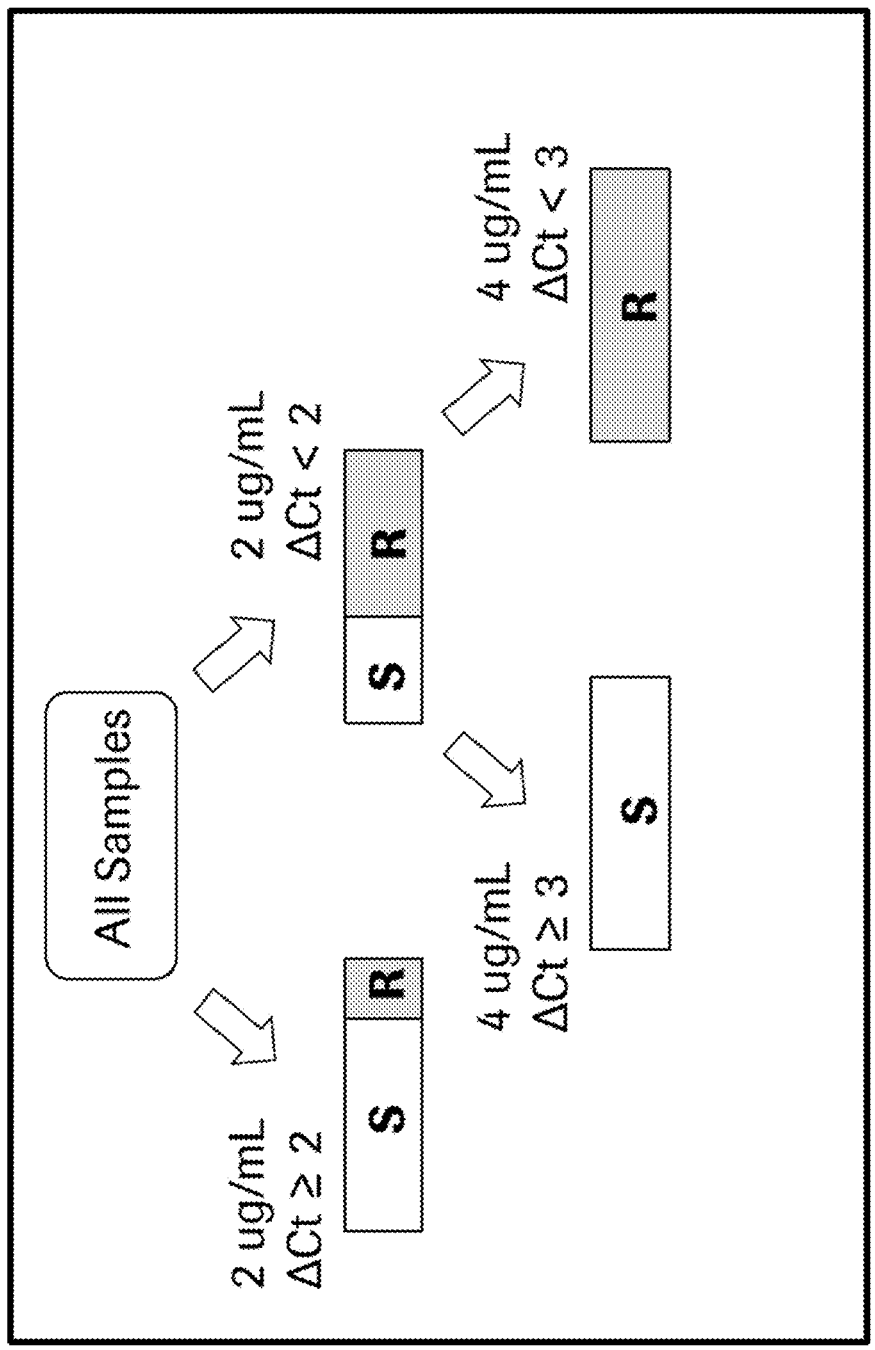
FIG. 4. Partitioning models were used to classify bacteria isolates as resistant or susceptible. Partitioning utilizes the Gini Index to determine which feature and threshold maximizes dispersion of the two classes. Only two splits are utilized to prevent overfitting and allows for graphical representation in two dimensions for easy visualization.

From the calculated differences in the mathematical features, simplified partitioning models such as that depicted in FIG. 4 were used to classify bacteria isolates as resistant or susceptible. Partitioning utilizes the Gini Index to determine which feature and threshold maximizes dispersion of the two classes. Only two splits are utilized to prevent overfitting and allows for graphical representation in two dimensions for easy visualization.

EXAMPLES

The following examples, tables and figures are provided to aid the understanding of the subject matter, the true scope of which is set forth in the appended claims. It is understood that modifications can be made in the procedures set forth without departing from the spirit of the invention.

Example 1 PCR Conditions

Real-time PCR detection of target genes were performed using the Cobas® 6800/8800 systems platforms (Roche Molecular Systems, Inc., Pleasanton, Calif.). The final concentrations of the amplification reagents are shown below:

TABLE XXIX

| PCR Amplification Reagents | | |
|---|---|---|
| Master Mix Component | Final Conc (45.0 uL) | |
| DMSO | 5.4 | % |
| NaN3 | 0.027 | % |
| Potassium acetate | 120.0 | mM |
| Glycerol | 3.0 | % |
| Tween 20 | 0.015 | % |
| NaN3 | 0.027 | % |
| Tricine | 60.0 | mM |

TABLE XXIX-continued

PCR Amplification Reagents

| Master Mix Component | Final Conc (45.0 uL) | |
|---|---|---|
| NTQ21-46AAptamer | 0.222 | uM |
| UNG Enzyme | 10.0 | U |
| Z05D-DNA Polymerase | 45.0 | U |
| dATP | 400.0 | uM |
| dCTP | 400.0 | uM |
| dGTP | 400.0 | uM |
| dUTP | 800.0 | uM |
| Forward primer oligonucleotides | 0.50 | µM |

TABLE XXIX-continued

PCR Amplification Reagents

| Master Mix Component | Final Conc (45.0 uL) | |
|---|---|---|
| Reverse primer oligonucleotides | 0.50 | µM |
| Probe oligonucleotides | 0.15 | µM |
| Manganese Acetate | 3.30 | mM |
| Trizma Base | 12 | µM |
| Methylparaben | 0.08 | % |

The following table shows the typical thermoprofile used for PCR amplification reaction:

TABLE XXX

PCR Thermoprofile

| Program Name | Target (° C.) | Acquisition Mode | Hold (hh:mm:ss) | Ramp Rate (° C./s) | Cycles | Analysis Mode |
|---|---|---|---|---|---|---|
| Pre-PCR | 50 | None | 00:02:00 | 4.4 | 1 | None |
|  | 94 | None | 00:00:05 | 4.4 |  |  |
|  | 55 | None | 00:02:00 | 2.2 |  |  |
|  | 60 | None | 00:06:00 | 4.4 |  |  |
|  | 65 | None | 00:04:00 | 4.4 |  |  |
| 1st Measurement | 95 | None | 00:00:05 | 4.4 | 5 | Quantification |
|  | 55 | Single | 00:00:30 | 2.2 |  |  |
| 2nd Measurement | 91 | None | 00:00:05 | 4.4 | 45 | Quantification |
|  | 58 | Single | 00:00:25 | 2.2 |  |  |
| Cooling | 40 | None | 00:02:00 | 2.2 | 1 | None |

The Pre-PCR program comprised initial denaturing and incubation at 55° C., 60° C. and 65° C. for reverse transcription of RNA templates. Incubating at three temperatures combines the advantageous effects that at lower temperatures slightly mismatched target sequences (such as genetic variants of an organism) are also transcribed, while at higher temperatures the formation of RNA secondary structures is suppressed, thus leading to a more efficient transcription. PCR cycling was divided into two measurements, wherein both measurements apply a one-step setup (combining annealing and extension). The first 5 cycles at 55° C. allow for an increased inclusivity by pre-amplifying slightly mismatched target sequences, whereas the 45 cycles of the second measurement provide for an increased specificity by using an annealing/extension temperature of 58° C.

Example 2 PCR Using Primers/Probes for Detecting Enterobacterales Order

Using the PCR conditions described in Example 1, PCR assays using forward primer RM_ENTF (SEQ ID NO: 1), reverse primer RM_ENTRP (SEQ ID NO: 2) and both probes RM_ETP02 (SEQ ID NO: 3) and RM_ETP02B (SEQ ID NO: 4) that target the rplP gene were tested against five bacteria strains from the Enterobacterales order: E. Coli, K. pneumonia, E. cloacae, S. marcescens, P. mirabilis, and two bacteria strains from non-Enterobacterales order: P. aeruginosa, and A. baumannii. The concentration of the starting material that used ranged between 1e8 and 5e8 CFU/ml for the culture fluid for all the strains (overnight cultures previously stored in glycerol) except for S. marcescens in which DNA (~1e7 copies/ul) was used. No sample preparation was performed for the culture fluids. The results of this experiment showed that growth curves are observed only for the five strains of the Enterobacterales order family but not for the two non-Enterobacterales strains, thereby demonstrating good inclusivity and exclusivity profiles for this particular combination of primers and probes for detecting Enterobacterales. Similar experiments were performed testing the P. aeruginosa-specific primers and probe (SEQ ID NOs: 5-8) and the A. baumannii-specific primers and probe (SEQ ID NOs: 9-11) which also showed good specificity and exclusivity (data not shown).

Figure 5:
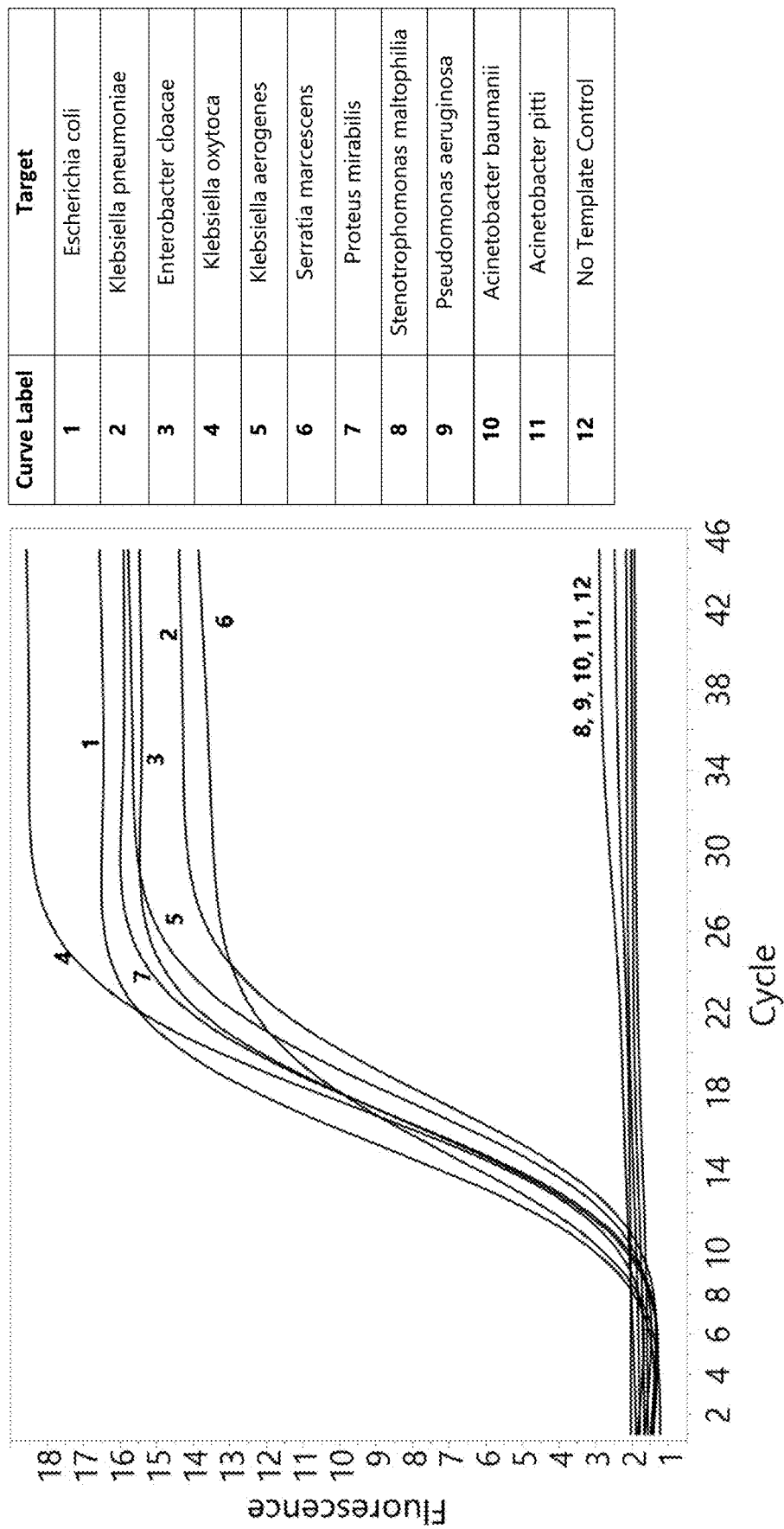
FIG. 5. PCR assays using primers and probe disclosed in TABLE III that target the gyrB gene were tested against common Gram-negative pathogens. Growth curves are observed only for the species that constitute the order Enterobacterales (including *E. coli, K. pneumoniae, E. cloacae, K. oxytoca, K. aerogenes, S. marcescens*, and *P. mirabilis*). No meaningful amplification was observed for non-target organisms.

PCR assays using forward primer SEGP1899 (SEQ ID NO: 8), reverse primer SEGP1901 (SEQ ID NO: 9) and probe SEGP2016 (SEQ ID NO: 10) that target the gyrB gene were tested against common Gram-negative pathogens: E. coli, K. pneumoniae, E. cloacae, K. oxytoca, K. aerogenes, S. marcescens, P. mirabilis, S. maltophilia, P. aeruginosa, A. baumannii, and A. pittii. Gram-positive organisms were also tested and showed no meaningful amplification (data not shown). The concentration of the genomic DNA was roughly 2-10 ng/uL for all samples, besides the no template control that was 0 ng/uL. As shown in FIG. 5, growth curves were observed only for the species that constitute the order Enterobacterales (including E. coli, K. pneumoniae, E. cloacae, K. oxytoca, K. aerogenes, S. marcescens, and P. mirabilis). No meaningful amplification was observed for non-target organisms (S. maltophilia, P. aeruginosa, A. baumannii, and A. pittii), thereby demonstrating good inclusivity and exclusivity profiles for this particular combination of primers and probes for detecting Enterobacterales.

Figure 6:
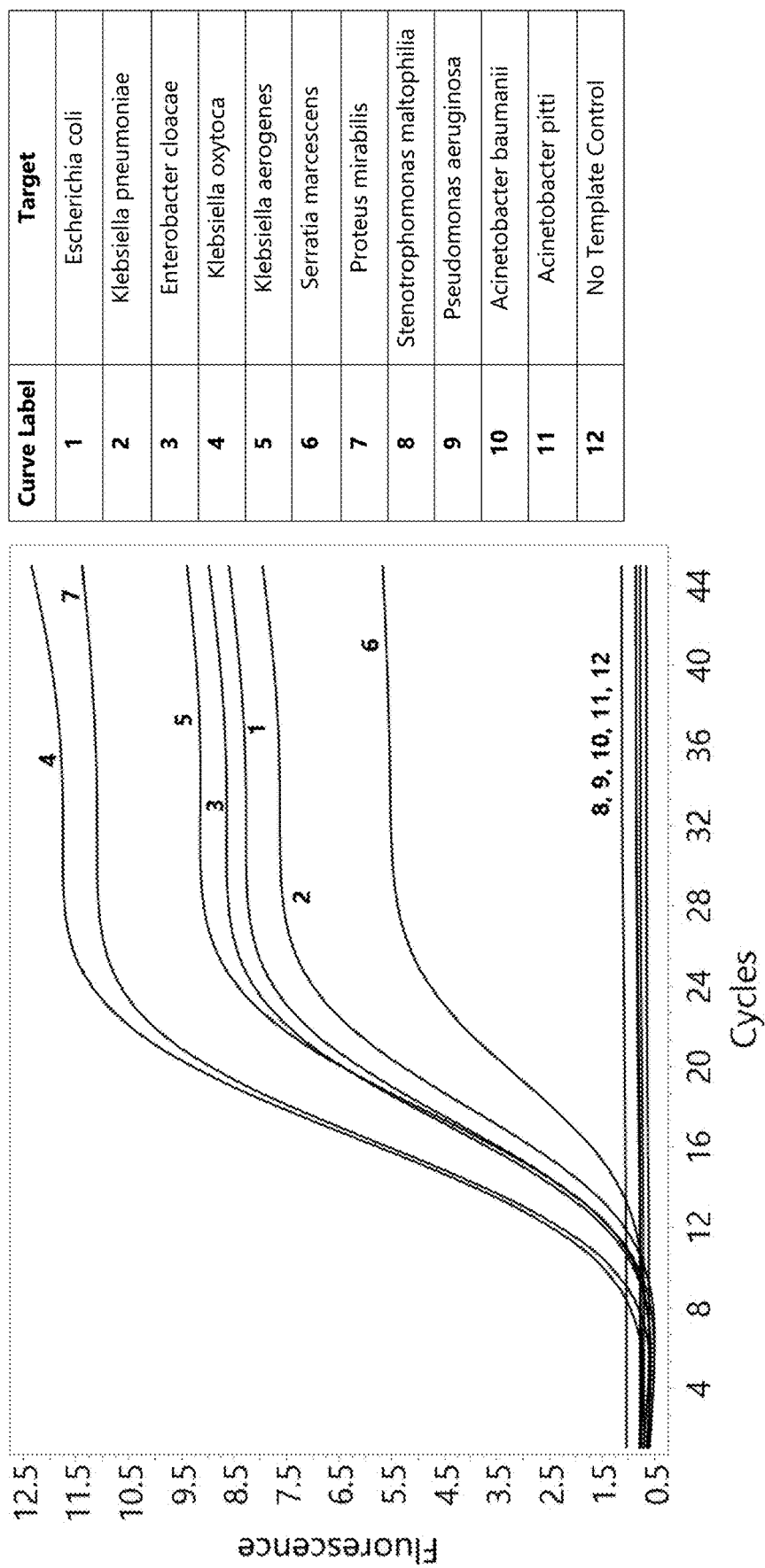
FIG. 6. PCR assays using primers and probe disclosed in TABLE II that target the rplP gene were tested against common Gram-negative pathogens. Growth curves are observed only for the species that constitute the order Enterobacterales. No meaningful amplification was observed for non-target organisms.

PCR assays were performed for other primers and probe combinations designed to target the rplP gene in Enterobacterales. PCR assays using forward primer SEGP2891 (SEQ ID NO: 5), reverse primer SEGP2892 (SEQ ID NO: 6) and probe SEGP2893 (SEQ ID NO: 7) that target the rplP gene were tested against common Gram-negative pathogens: E. coli, K. pneumoniae, E. cloacae, K. oxytoca, K. aerogenes, S. marcescens, P. mirabilis, S. maltophilia, P. aeruginosa, A. baumannii, and A. pittii. Gram-positive organisms were also tested and showed no meaningful amplification (data not shown). The concentration of the genomic DNA was roughly 2-10 ng/uL for all samples, besides the no template control which was 0 ng/uL. As shown in FIG. 6, growth curves were observed only for the species that constitute the order Enterobacterales (including *E. coli, K. pneumoniae, E. cloacae, K. oxytoca, K. aerogenes, S. marcescens,* and *P. mirabilis*). No meaningful amplification was observed for non-target organisms (*S. maltophilia, P. aeruginosa, A. baumannii,* and *A. pittii*), thereby demonstrating good inclusivity and exclusivity profiles for this particular combination of primers and probes for detecting Enterobacterales.

Figure 7:
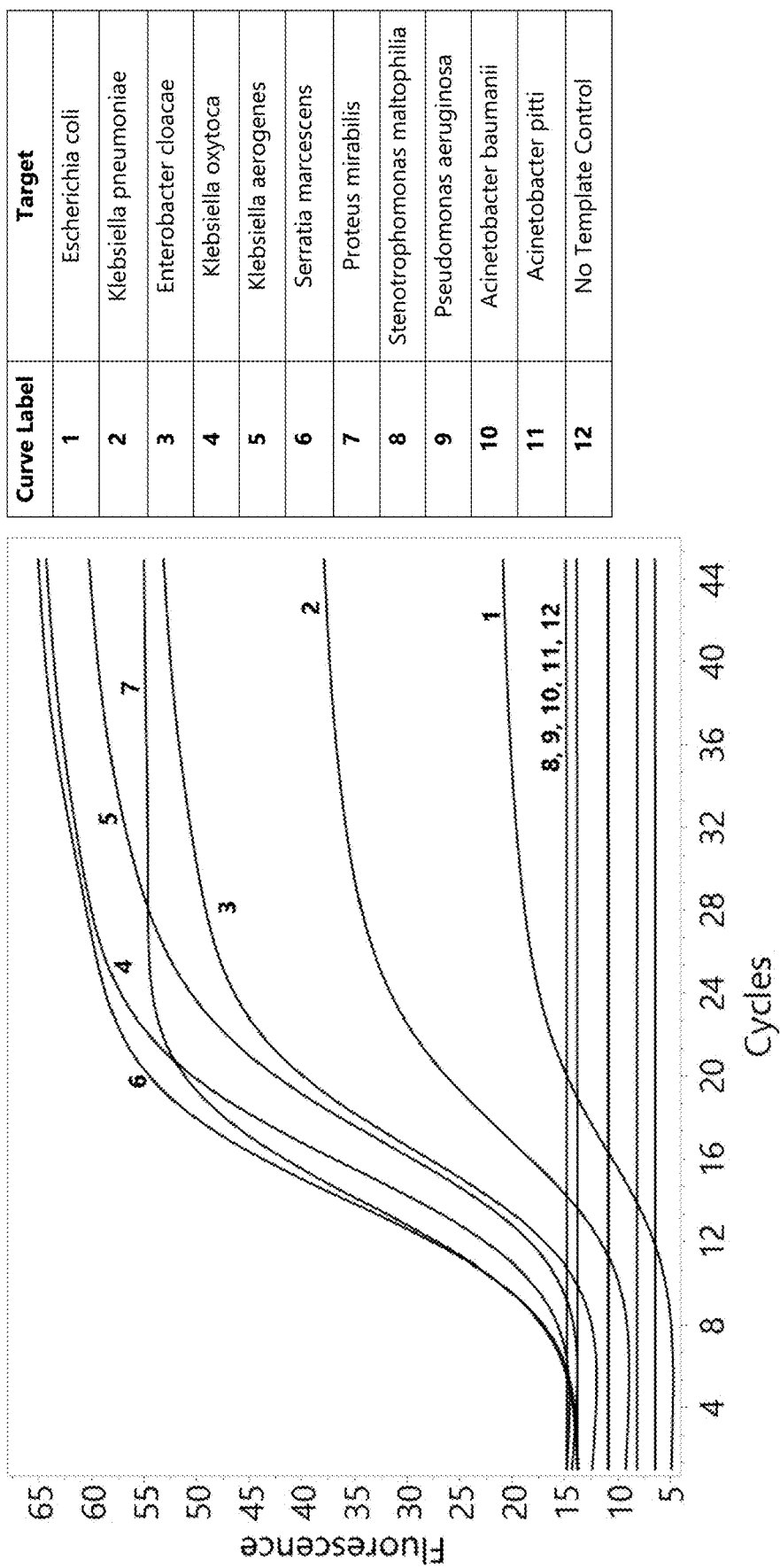
FIG. 7. PCR assays using primers and probe disclosed in TABLE IV that target the rpoB gene were tested against common Gram-negative pathogens. Growth curves were observed only for the species that constitute the order Enterobacterales. No meaningful amplification was observed for non-target organisms.

Similar results were obtained in PCR assays using forward primer SEGP2799 (SEQ ID NO: 11), reverse primers SEGP2800 (SEQ ID NO: 12), SEGP2802 (SEQ ID NO: 13), and SEGP2821 (SEQ ID NO: 14), in combination with probes SEGP2804 (SEQ ID NO: 15) and SEGP2822 (SEQ ID NO: 16) that target the rpoB gene. As shown in FIG. 7, growth curves were observed only for the species that constitute the order Enterobacterales (including *E. coli, K. pneumoniae, E. cloacae, K. oxytoca, K. aerogenes, S. marcescens,* and *P. mirabilis*). No meaningful amplification was observed for non-target organisms (*S. maltophilia, P. aeruginosa, A. baumannii,* and *A. pittii*), thereby demonstrating good inclusivity and exclusivity profiles for this particular combination of primers and probes for detecting Enterobacterales.

Example 3 PCR Using Primers/Probes for Detecting *Acinetobacter* Genus

Figure 8:
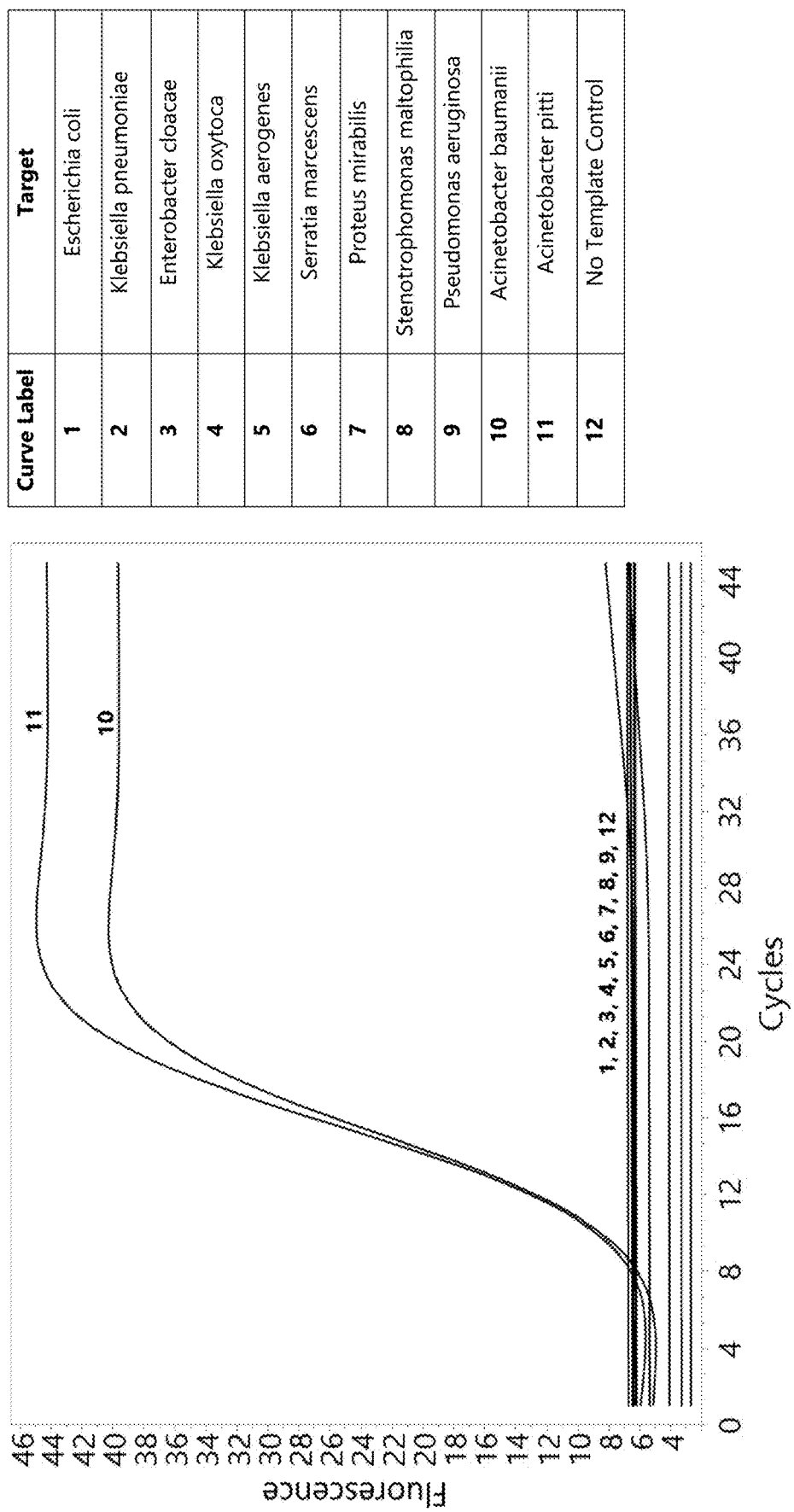
FIG. 8. PCR assays using primers and probe disclosed in TABLE V that target the ompA gene were tested against common Gram-negative pathogens: *E. coli, K. pneumoniae, E. cloacae, K. oxytoca, K. aerogenes, S. marcescens, P. mirabilis, S. maltophilia, P. aeruginosa, A. baumannii*, and *A. pittii*. Growth curves are observed only for the prevalent pathogens that are within the genus *Acinetobacter* (*A. baumannii* and *A. pittii*). No meaningful amplification was observed for non-target organisms.

PCR assays using forward primer SEGP2603 (SEQ ID NO: 20), reverse primer SEGP2606 (SEQ ID NO: 21), and probe SEGP2769 (SEQ ID NO: 22) that target the ompA gene were tested against common Gram-negative pathogens: *E. coli, K. pneumoniae, E. cloacae, K. oxytoca, K. aerogenes, S. marcescens, P. mirabilis, S. maltophilia, P. aeruginosa, A. baumannii,* and *A. pittii*. Gram-positive organisms were also tested and showed no meaningful amplification (data not shown). The concentration of the genomic DNA was roughly 2-10 ng/uL for all samples, besides the no template control that was 0 ng/uL. As shown in FIG. 8, growth curves were observed only for the prevalent pathogens that are within the genus *Acinetobacter* (*A. baumannii* and *A. pittii*). No meaningful amplification was observed for non-target organisms (*E. coli, K. pneumoniae, E. cloacae, K. oxytoca, K. aerogenes, S. marcescens, P. mirabilis, S. maltophilia,* and *P. aeruginosa*), thereby demonstrating good inclusivity and exclusivity profiles for this particular combination of primers and probes for detecting *Acinetobacter*.

Figure 9:
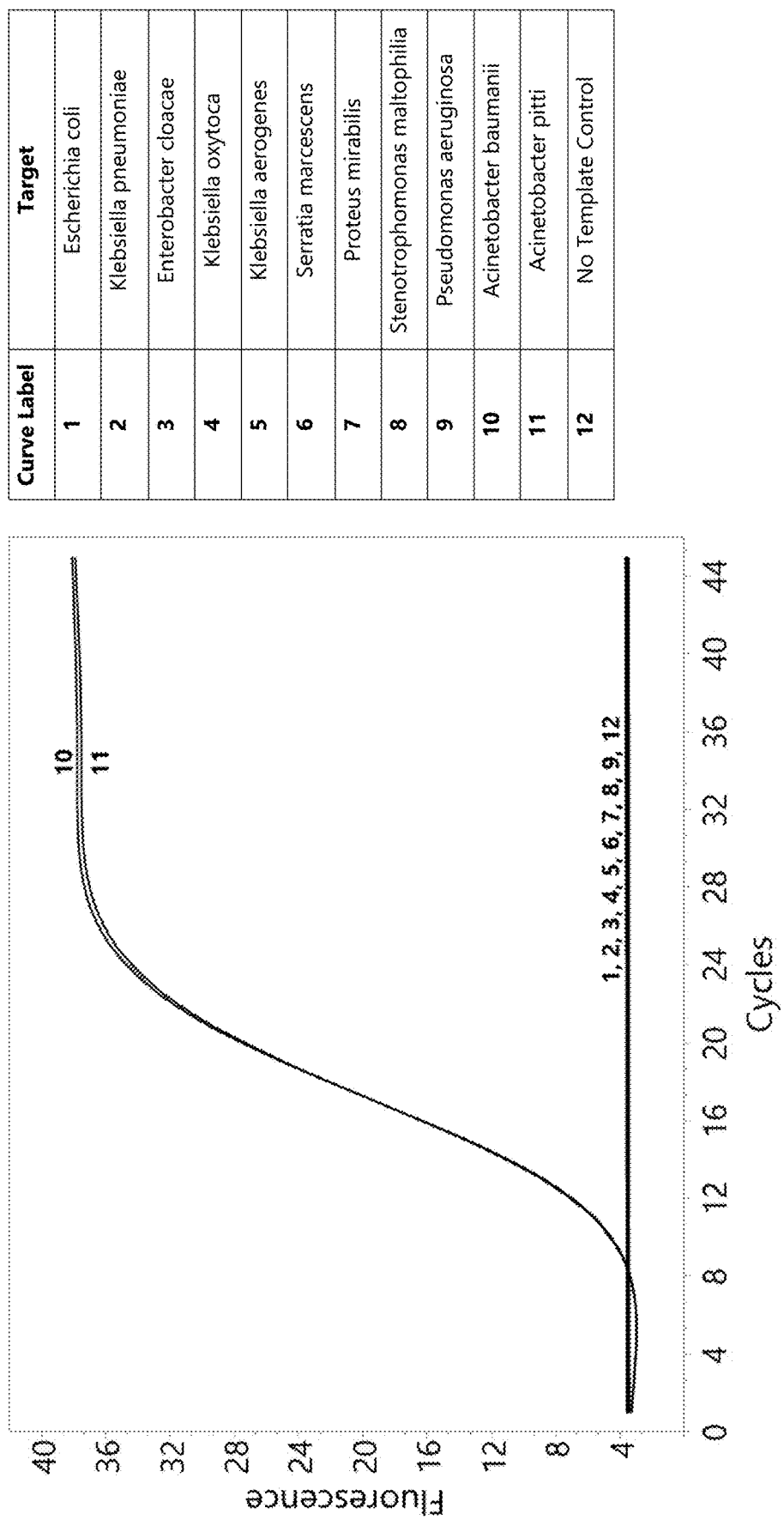
FIG. 9. PCR assays using primers and probe disclosed in TABLE VI that target the rpoB gene were tested against common Gram-negative pathogens. Growth curves are observed only for the prevalent pathogens that are within the genus *Acinetobacter*. No meaningful amplification was observed for non-target organisms.
Figure 10:
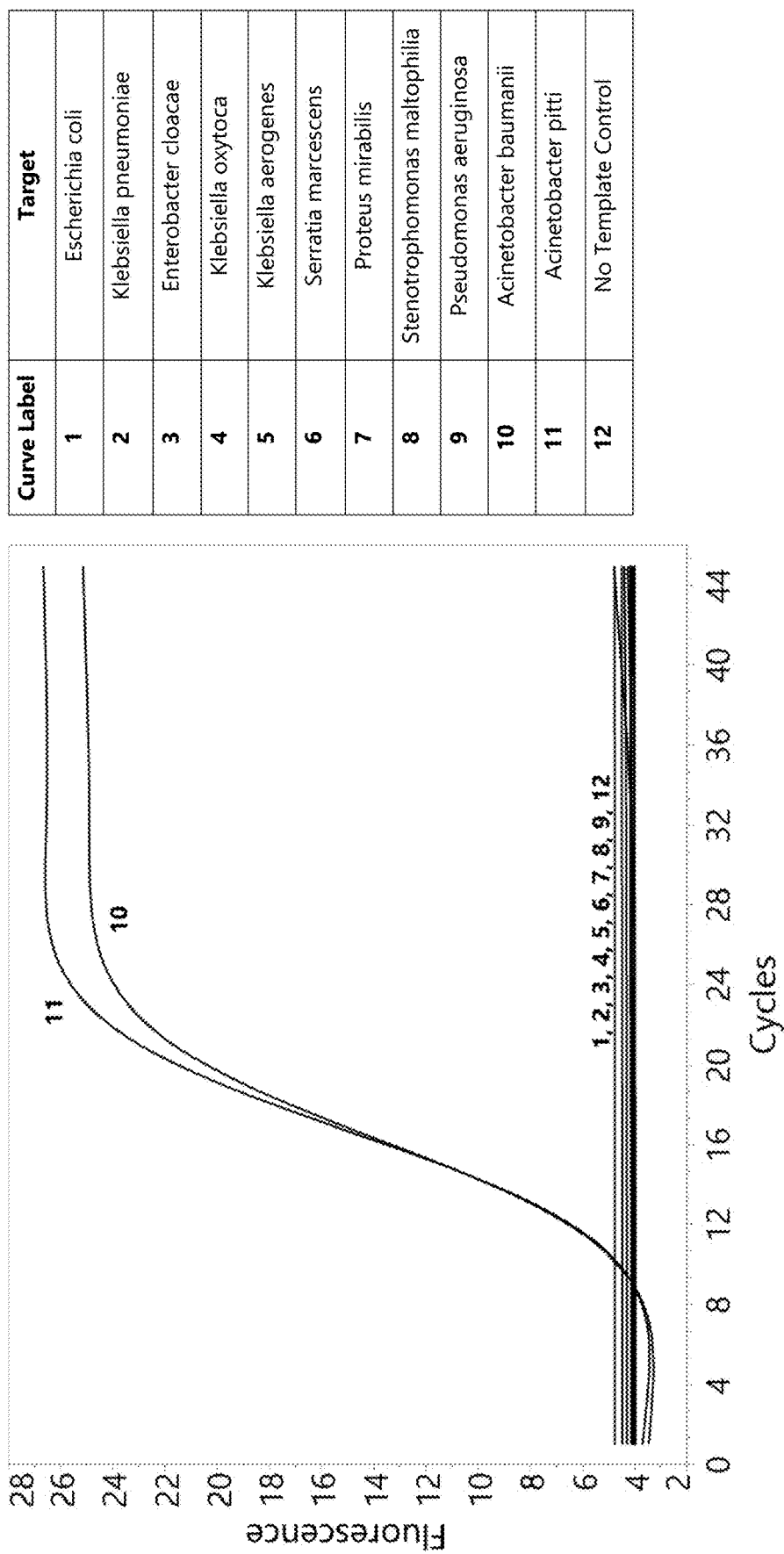
FIG. 10. PCR assays using primers and probe disclosed in TABLE VII that target the gyrB gene were tested against common Gram-negative pathogens. Growth curves are observed only for the prevalent pathogens that are within the genus *Acinetobacter*. No meaningful amplification was observed for non-target organisms.

Similar results were obtained in PCR assays using forward primer SEGP2590 (SEQ ID NO: 23), reverse primer SEGP2593 (SEQ ID NO: 24), and probe SEGP2594 (SEQ ID NO: 25) that target the rpoB gene (as shown in FIG. 9), and in PCR assays using forward primer SEGP2626 (SEQ ID NO: 26), reverse primer SEGP2628 (SEQ ID NO: 27) and probe SEGP2629 (SEQ ID NO: 28) that target the gyrB gene (as shown in FIG. 10). These experiments demonstrate good inclusivity and exclusivity profiles for both combinations of primers and probes for detecting *Acinetobacter*.

Example 4 PCR Using Primers/Probes for Detecting *Pseudomonas aeruginosa*

Figure 11:
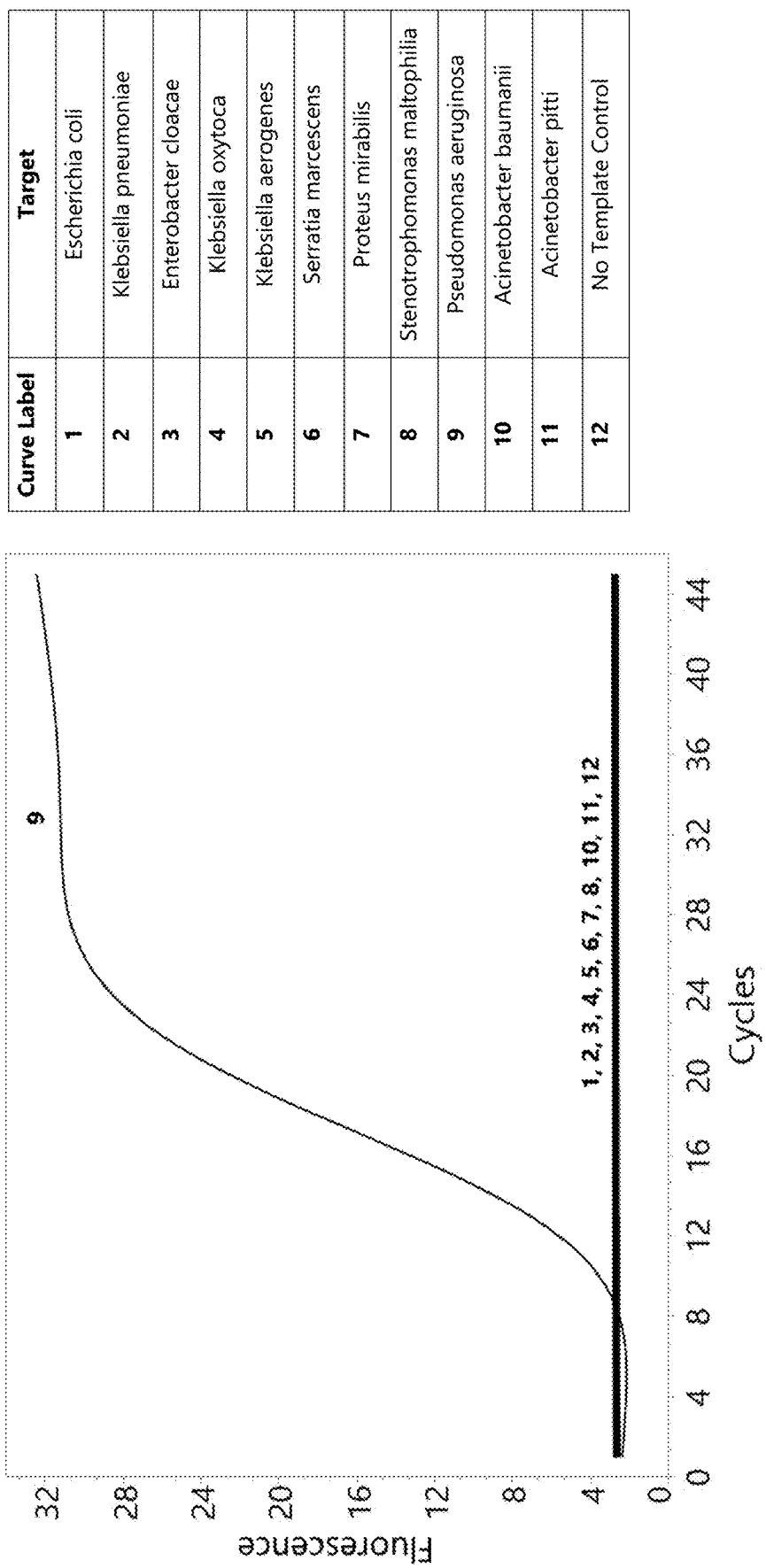
FIG. 11. PCR assays using primers and probe disclosed in TABLE VIII that target the tuf gene were tested against common Gram-negative pathogens: *E. coli, K. pneumoniae, E. cloacae, K. oxytoca, K. aerogenes, S. marcescens, P. mirabilis, S. maltophilia, P. aeruginosa, A. baumannii*, and *A. pittii*. Growth curve is observed only for pathogens within the genus *Pseudomonas* (*P. aeruginosa*). No meaningful amplification was observed for non-target organisms.

PCR assays using forward primer SEGP2341 (SEQ ID NO: 32), reverse primer SEGP2342 (SEQ ID NO: 33) and probe SEGP2343 (SEQ ID NO: 34) that target the tuf gene were tested against common Gram-negative pathogens: *E. coli, K. pneumoniae, E. cloacae, K. oxytoca, K. aerogenes, S. marcescens, P. mirabilis, S. maltophilia, P. aeruginosa, A. baumannii,* and *A. pittii*. Gram-positive organisms were also tested and showed no meaningful amplification (data not shown). The concentration of the genomic DNA was roughly 2-10 ng/uL for all samples, besides the no template control that was 0 ng/uL. As shown in FIG. 11, growth curves were observed only for pathogens within the genus *Pseudomonas* (*P. aeruginosa*). No meaningful amplification was observed for non-target organisms (*E. coli, K. pneumoniae, E. cloacae, K. oxytoca, K. aerogenes, S. marcescens, P. mirabilis, S. maltophilia, A. baumannii,* and *A. pittii*), thereby demonstrating good inclusivity and exclusivity profiles for this particular combination of primers and probes for detecting *P. aeruginosa*.

Figure 12:
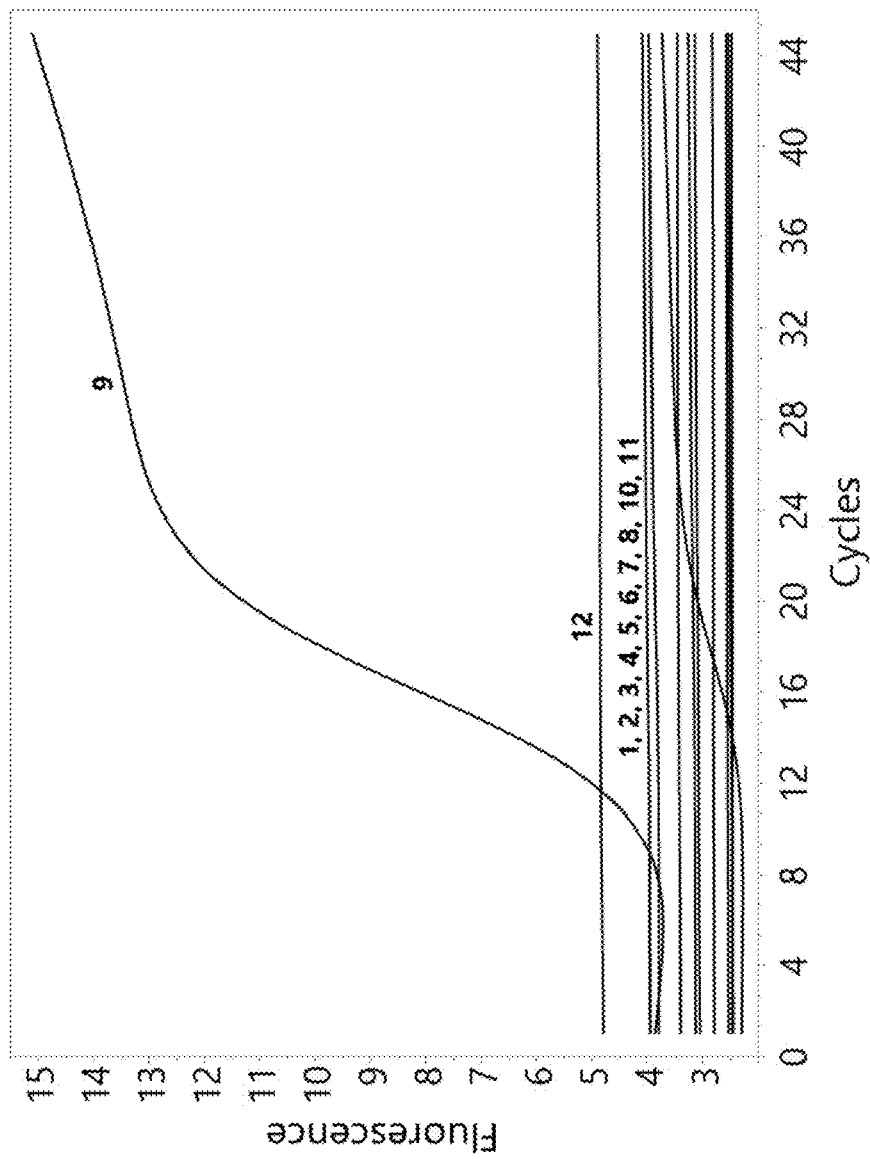
FIG. 12. PCR assays using primers and probe disclosed in TABLE IX that target the gyrB gene were tested against common Gram-negative pathogens. Growth curve is observed only for pathogens within the genus *Pseudomonas* (*P. aeruginosa*). No meaningful amplification was observed for non-target organisms.
Figure 13:
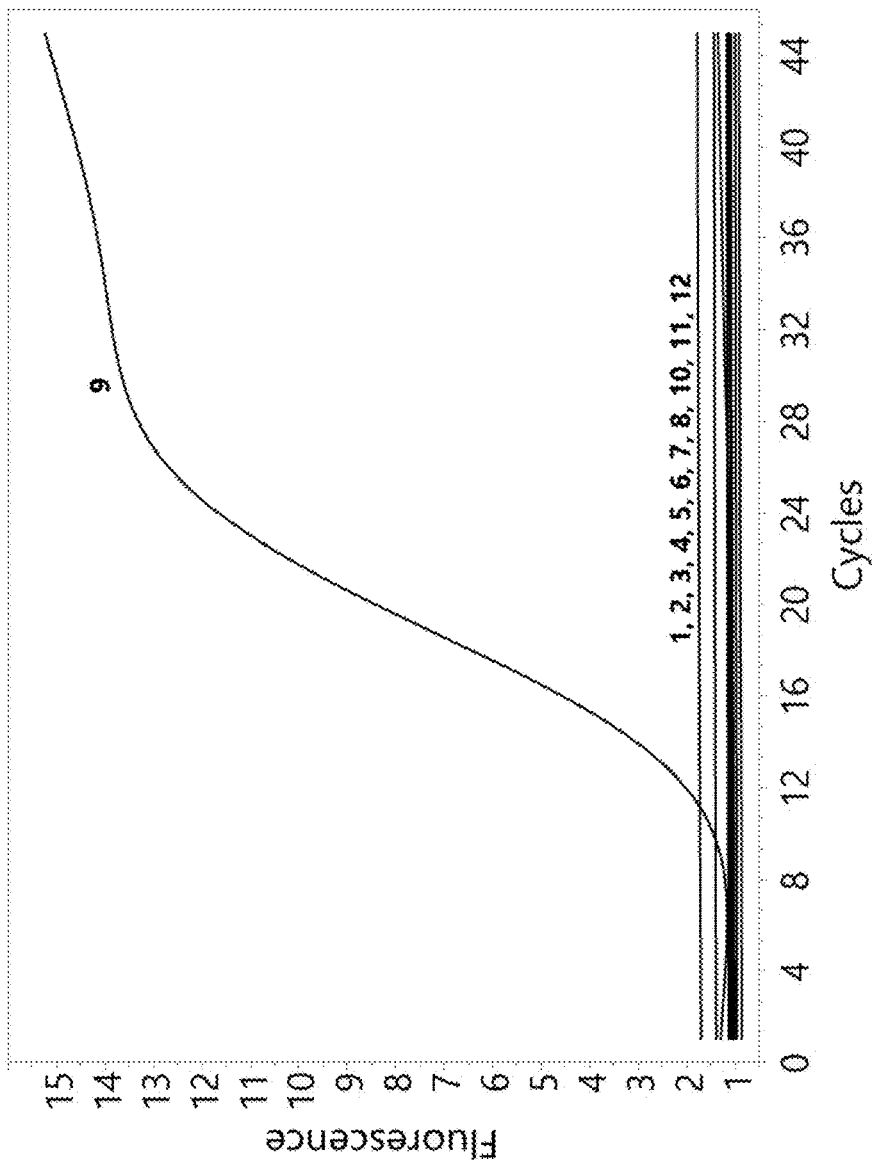
FIG. 13. PCR assays using primers and probe disclosed in TABLE X that target the rpoB gene were tested against common Gram-negative pathogens. Growth curve is observed only for pathogens within the genus *Pseudomonas* (*P. aeruginosa*). No meaningful amplification was observed for non-target organisms.

Similar results were obtained in PCR assays using forward primer SEGP2630 (SEQ ID NO: 35), reverse primer SEGP2631 (SEQ ID NO: 36), and probe SEGP2632 (SEQ ID NO: 37) that target the gyrB gene (as shown in FIG. 12), and in PCR assays using forward primer SEGP2634 (SEQ ID NO: 38), reverse primer SEGP2637 (SEQ ID NO: 39) and probe SEGP2640 (SEQ ID NO: 40) that target the rpoB gene (as shown in FIG. 13). These experiments demonstrate good inclusivity and exclusivity profiles for both combinations of primers and probes for detecting *P. aeruginosa*.

Example 5 PCR Using Primers/Probes for Detecting *Stenotrophomonas maltophilia*

Figure 14:
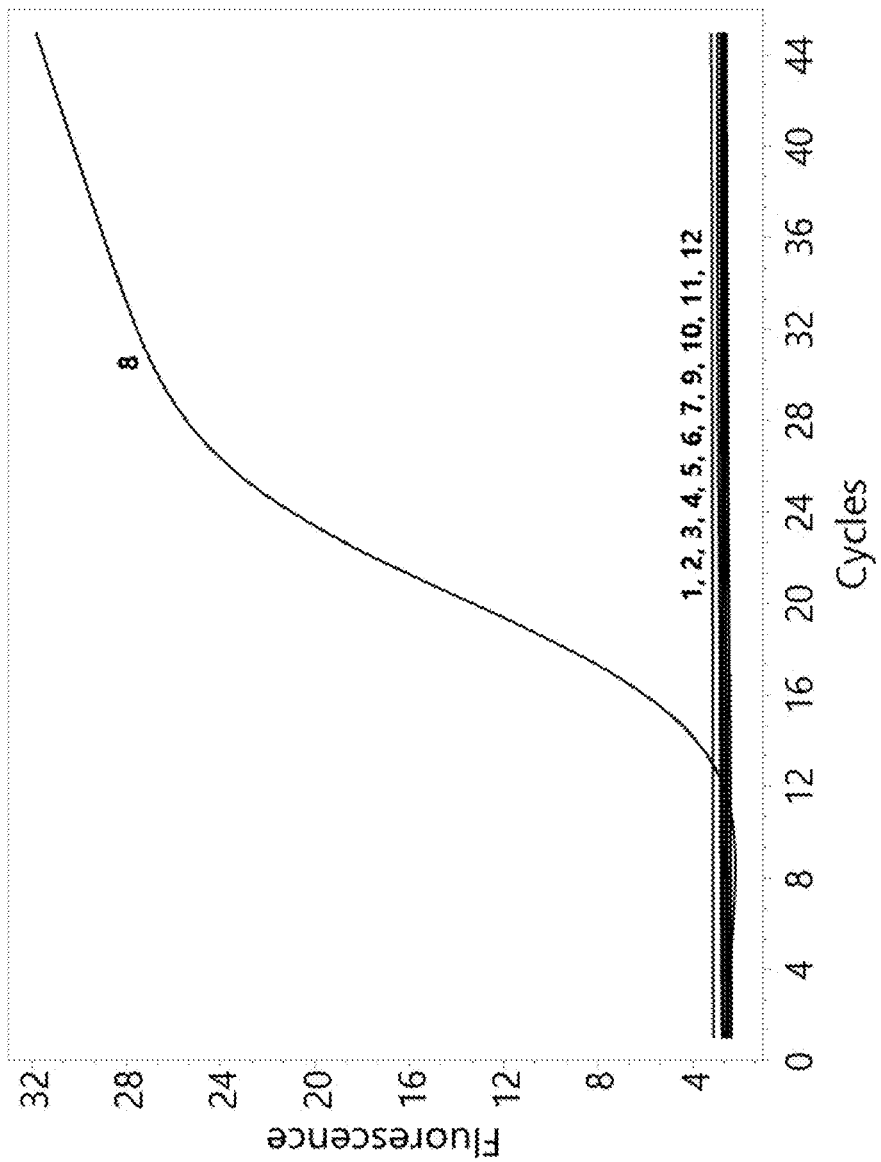
FIG. 14. PCR assays using primers and probe disclosed in TABLE XI that target the fdnG gene were tested against common Gram-negative pathogens: *E. coli, K. pneumoniae, E. cloacae, K. oxytoca, K. aerogenes, S. marcescens, P. mirabilis, S. maltophilia, P. aeruginosa, A. baumannii*, and *A. pittii*. Growth curve is observed only for the species of *Stenotrophomas maltophilia*. No meaningful amplification was observed for non-target organisms.

PCR assays using forward primer SEGP2532 (SEQ ID NO: 41), reverse primer SEGP2538 (SEQ ID NO: 42) and probe SEGP2544 (SEQ ID NO: 43) that target the fdnG gene were tested against common Gram-negative pathogens: *E. coli, K. pneumoniae, E. cloacae, K. oxytoca, K. aerogenes, S. marcescens, P. mirabilis, S. maltophilia, P. aeruginosa, A. baumannii,* and *A. pittii*. Gram-positive organisms were also tested and showed no meaningful amplification (data not shown). The concentration of the genomic DNA was roughly 2-10 ng/uL for all samples, besides the no template control that was 0 ng/uL. As shown in FIG. 14, growth curves were observed only for the species of *Stenotrophomonas maltophilia* (*S. maltophilia*). No meaningful amplification was observed for non-target organisms (*E. coli, K. pneumoniae, E. cloacae, K. oxytoca, K. aerogenes, S. marcescens, P. mirabilis, P. aeruginosa, A. baumannii,* and *A. pittii*), thereby demonstrating good inclusivity and exclusivity profiles for this particular combination of primers and probes for detecting *S. maltophilia*.

Figure 15:
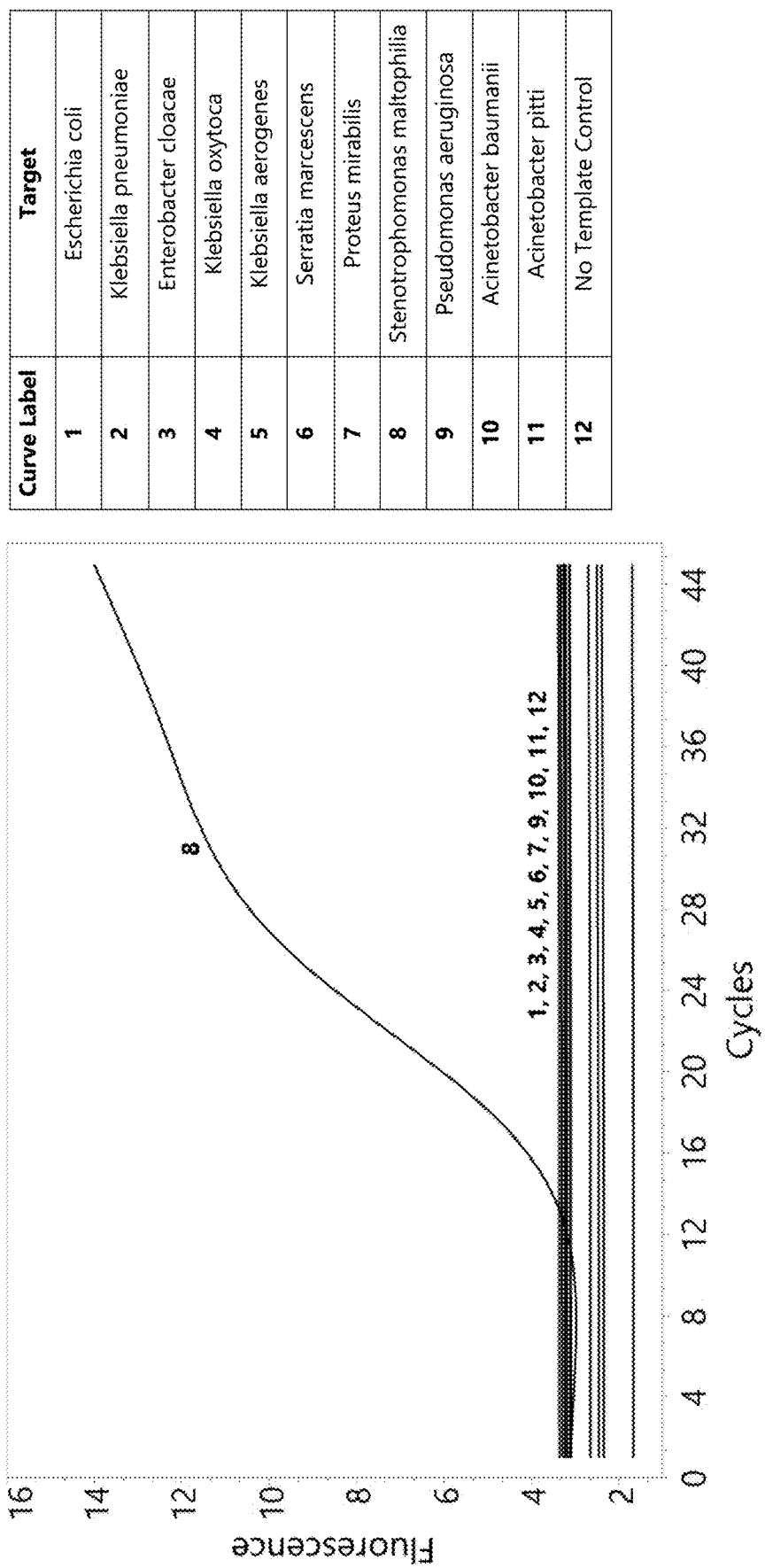
FIG. 15. PCR assays using primers and probe disclosed in TABLE XII that target the gyrB gene were tested against common Gram-negative pathogens. Growth curve is observed only for the species of *Stenotrophomas maltophilia*. No meaningful amplification was observed for non-target organisms.
Figure 16:
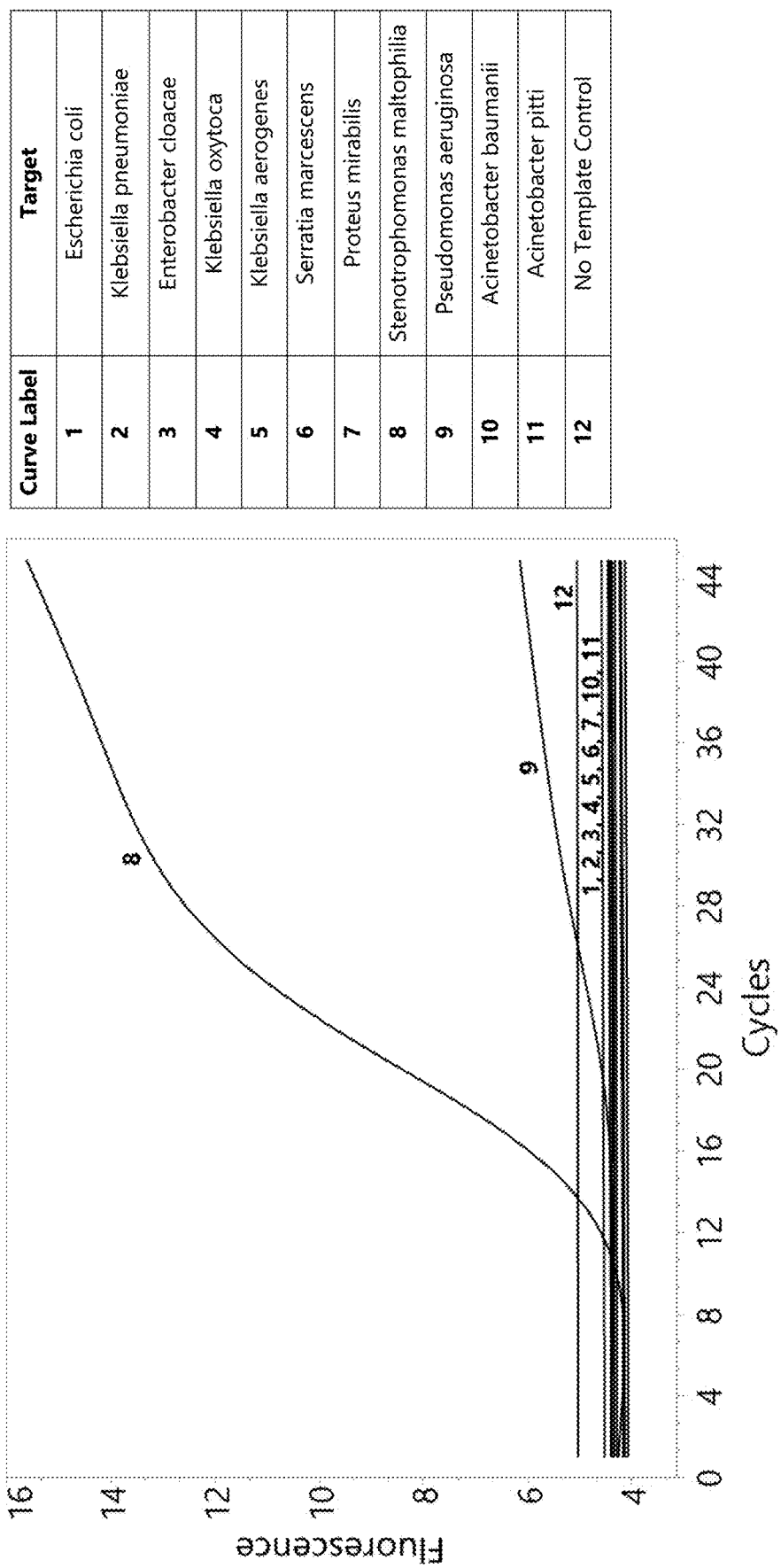
FIG. 16. PCR assays using primers and probe disclosed in TABLE XIII that target the tuf gene were tested against common Gram-negative pathogens. Growth curve is observed only for the species of *Stenotrophomas maltophilia*. No meaningful amplification was observed for non-target organisms.

Similar results were obtained in PCR assays using forward primer SEGP2578 (SEQ ID NO: 44), reverse primer SEGP2579 (SEQ ID NO: 45), and probe SEGP2580 (SEQ ID NO: 46) that target the gyrB gene (as shown in FIG. 15), and in PCR assays using forward primer SEGP2572 (SEQ ID NO: 47), reverse primer SEGP2573 (SEQ ID NO: 48) and probe SEGP2574 (SEQ ID NO: 49) that target the tuf gene (as shown in FIG. 16). These experiments demonstrate good inclusivity and exclusivity profiles for both combinations of primers and probes for detecting *S. maltophilia*.

Example 6 PCR Using Primers/Probes for Detecting *Enterococcus* Genus

PCR assays using forward primer SEGP2522 (SEQ ID NO: 53), reverse primer SEGP2525 (SEQ ID NO: 54), and probe SEGP2770 (SEQ ID NO: 55) that target the rpoB gene were tested against common Gram-positive pathogens: *S. agalactiae, S. pneumoniae, S. pyogenes, E. faecium, E.*

Figure 17:
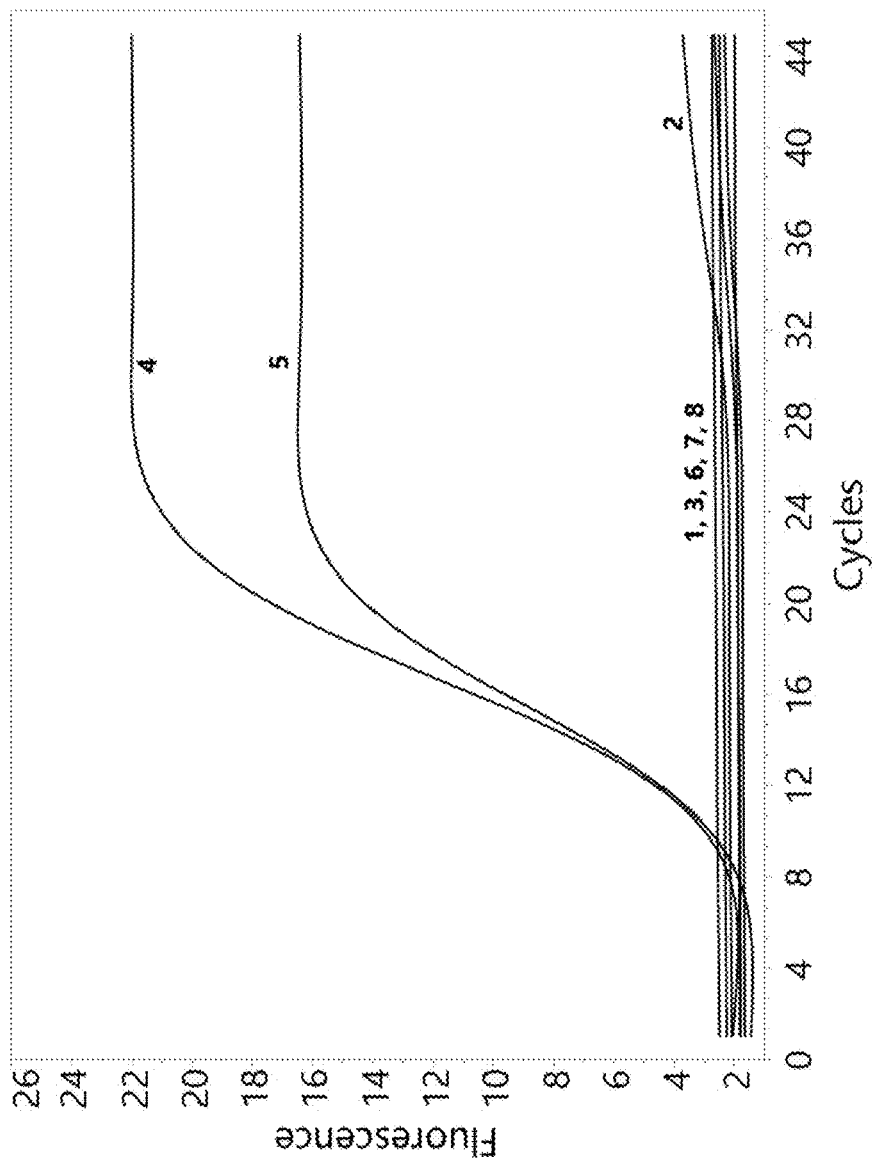
FIG. 17. PCR assays using primers and probe disclosed in TABLE XV that target the rpoB gene were tested against common Gram-positive pathogens: *S. agalactiae, S. pneumoniae, S. pyogenes, E. faecium, E. faecalis, S. aureus*, and *S. epidermidis*. Growth curves are observed only for pathogens within the genus *Enterococcus* (*E. faecium* and *E. faecalis*). No meaningful amplification was observed for non-target organisms.

*faecalis, S. aureus,* and *S. epidermidis.* Gram-negative organisms were also tested and showed no meaningful amplification (data not shown). The concentration of the genomic DNA was roughly 2-10 ng/uL for all samples, besides the no template control that was 0 ng/uL. As shown in FIG. 17, amplification curves are observed only for pathogens within the genus *Enterococcus* (*E. faecium* and *E. faecalis*). No meaningful amplification was observed for non-target organisms (*S. agalactiae, S. pneumoniae, S. pyogenes, S. aureus,* and *S. epidermidis*), thereby demonstrating good inclusivity and exclusivity profiles for this particular combination of primers and probes for detecting *Enterococcus.*

Figure 18:
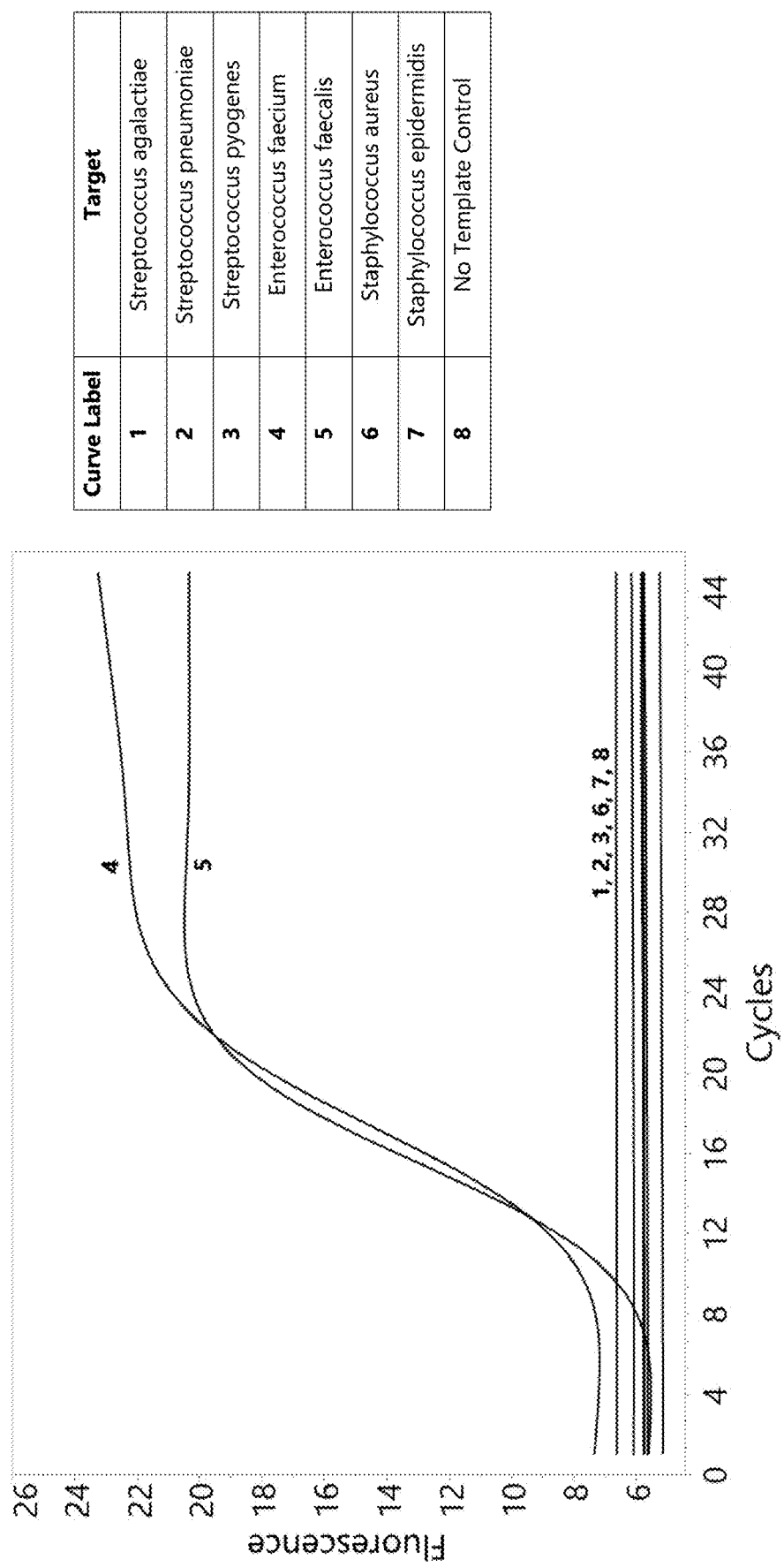
FIG. 18. PCR assays using primers and probes disclosed in TABLE XVI that target the ddl gene were tested against common Gram-positive pathogens. Growth curves are observed only for pathogens within the genus *Enterococcus* (*E. faecium* and *E. faecalis*). No meaningful amplification was observed for non-target organisms.
Figure 19:
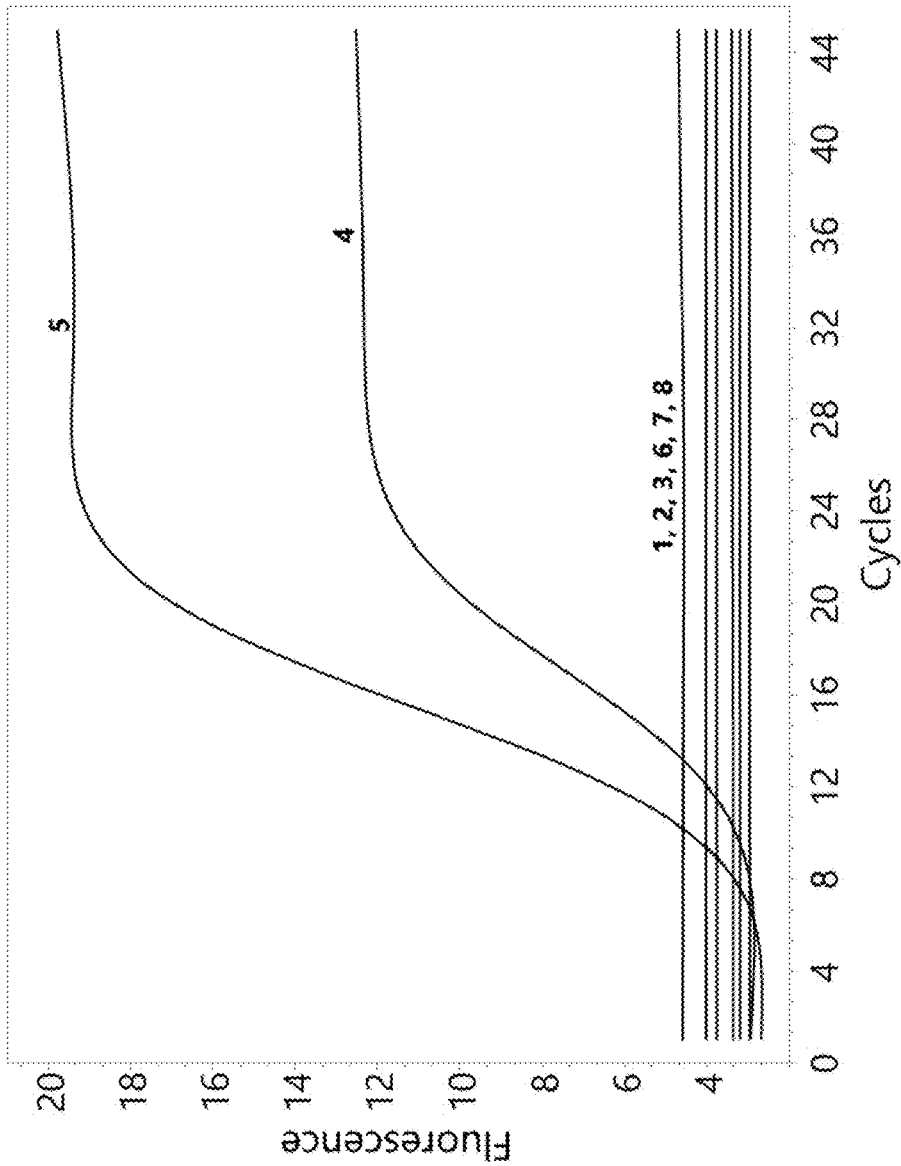
FIG. 19. PCR assays using primers and probe disclosed in TABLE XVII targeting the gyrB gene were tested against common Gram-positive pathogens. Growth curves are observed only for pathogens within the genus *Enterococcus* (*E. faecium* and *E. faecalis*). No meaningful amplification was observed for non-target organisms.

Similar results were obtained in PCR assays using forward primers SEGP1624 (SEQ ID NO: 56) and SEGP1627 (SEQ ID NO: 57), reverse primers SEGP1625 (SEQ ID NO: 58) and SEGP1628 (SEQ ID NO: 59), and probes SEGP1626 (SEQ ID NO: 60) and SEGP1629 (SEQ ID NO: 61) that target the ddl gene (as shown in FIG. 18). Good specificity was also observed in PCR assays using forward primers SEGP2882 (SEQ ID NO: 62) and SEGP2884 (SEQ ID NO: 63), reverse primers SEGP2885 (SEQ ID NO: 64) and SEGP2886 (SEQ ID NO: 65) and probe SEGP2888 (SEQ ID NO: 66) that target the gyrB gene (as shown in FIG. 19). These experiments demonstrate good inclusivity and exclusivity profiles for both combinations of primers and probes for detecting *Enterococcus.*

Example 7 PCR Using Primers/Probes for Detecting *Staphylococcus aureus*

Figure 20:
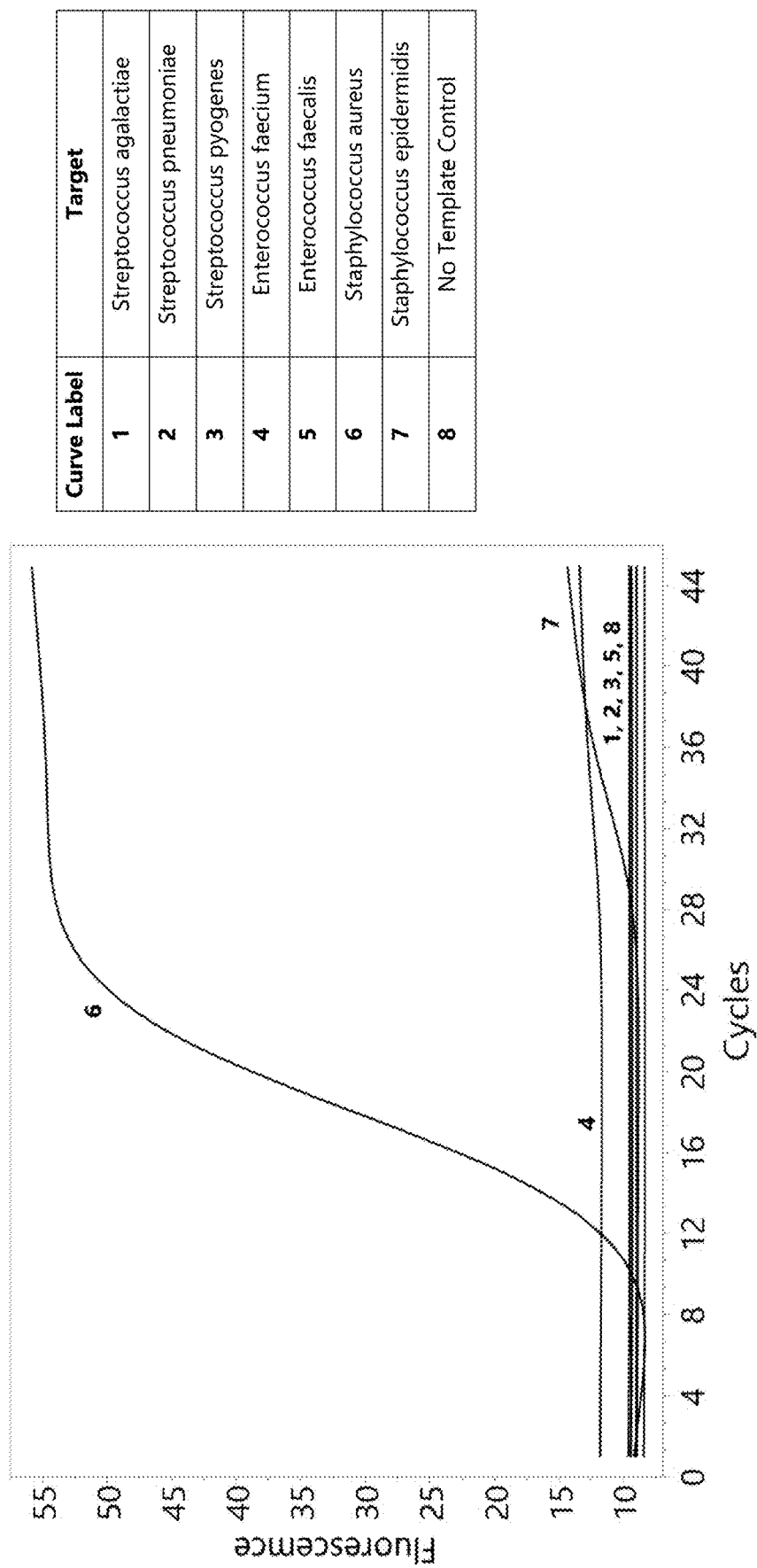
FIG. 20. PCR assays using primers and probe disclosed in TABLE XVIII that target the CPE gene were tested against common Gram-positive pathogens: *S. agalactiae, S. pneumoniae, S. pyogenes, E. faecium, E. faecalis, S. aureus*, and *S. epidermidis*. Growth curve is observed only for pathogens within the species *Staphylococcus aureus*. No meaningful amplification was observed for non-target organisms.

PCR assays using forward primer SEGP1490 (SEQ ID NO: 67), reverse primer SEGP1491 (SEQ ID NO: 68) and probe SEGP1492 (SEQ ID NO: 72) that target the CPE gene were tested against common Gram-positive pathogens: *S. agalactiae, S. pneumoniae, S. pyogenes, E. faecium, E. faecalis, S. aureus,* and *S. epidermidis.* Gram-negative organisms were also tested and showed no meaningful amplification (data not shown). The concentration of the genomic DNA was roughly 2-10 ng/uL for all samples, besides the no template control that was 0 ng/uL. As shown in FIG. 20, meaningful growth curves were observed only for pathogens within the species *Staphylococcus aureus.* No meaningful amplification was observed for non-target organisms (*S. agalactiae, S. pneumoniae, S. pyogenes, E. faecium, E. faecalis,* and *S. epidermidis*), thereby demonstrating good inclusivity and exclusivity profiles for this particular combination of primers and probes for detecting *S. aureus.*

Figure 21:
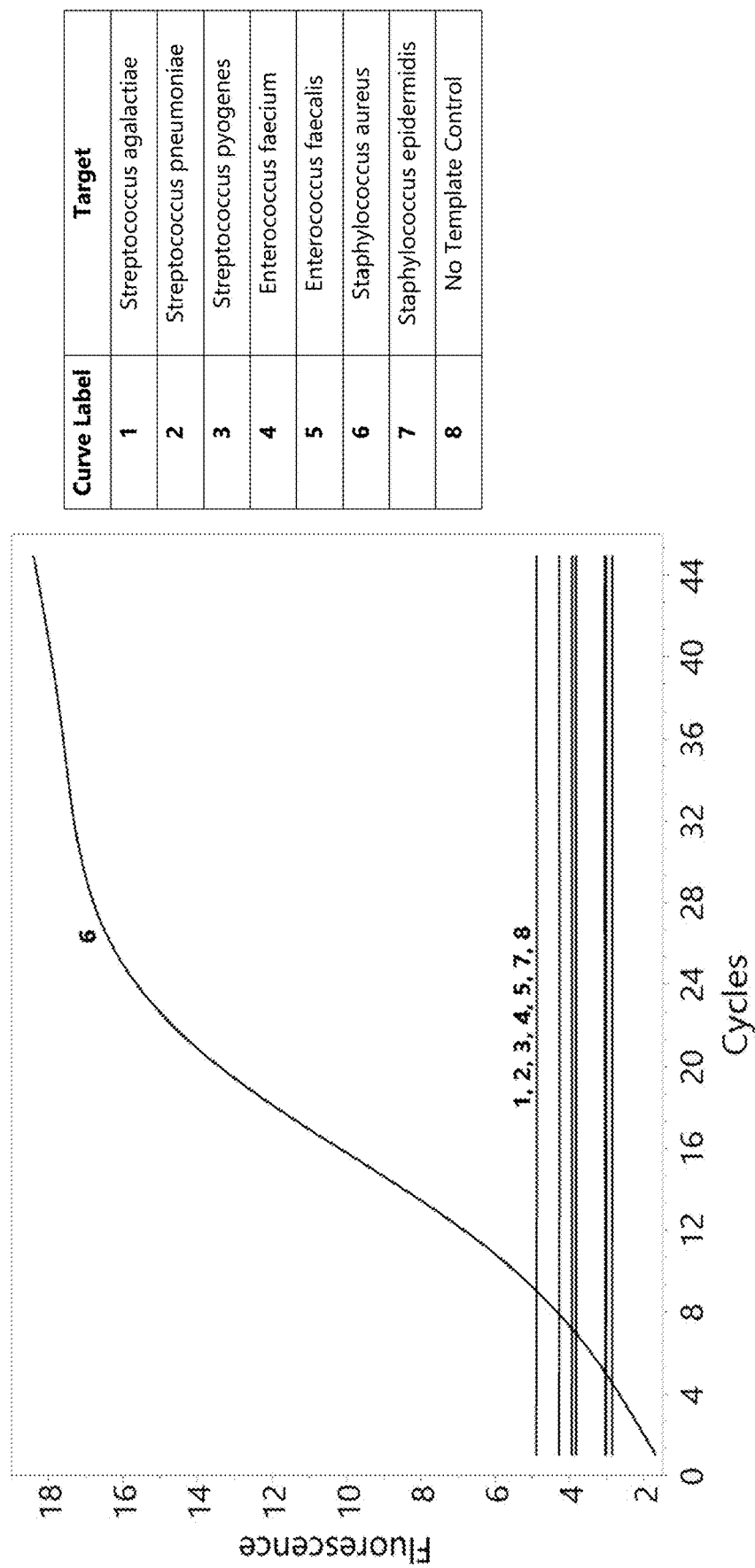
FIG. 21. PCR assays using primers and probe disclosed in TABLE XIX that target the gyrB gene were tested against common Gram-positive pathogens. Growth curve is observed only for pathogens within the species *Staphylococcus aureus*. No meaningful amplification was observed for non-target organisms.
Figure 22:
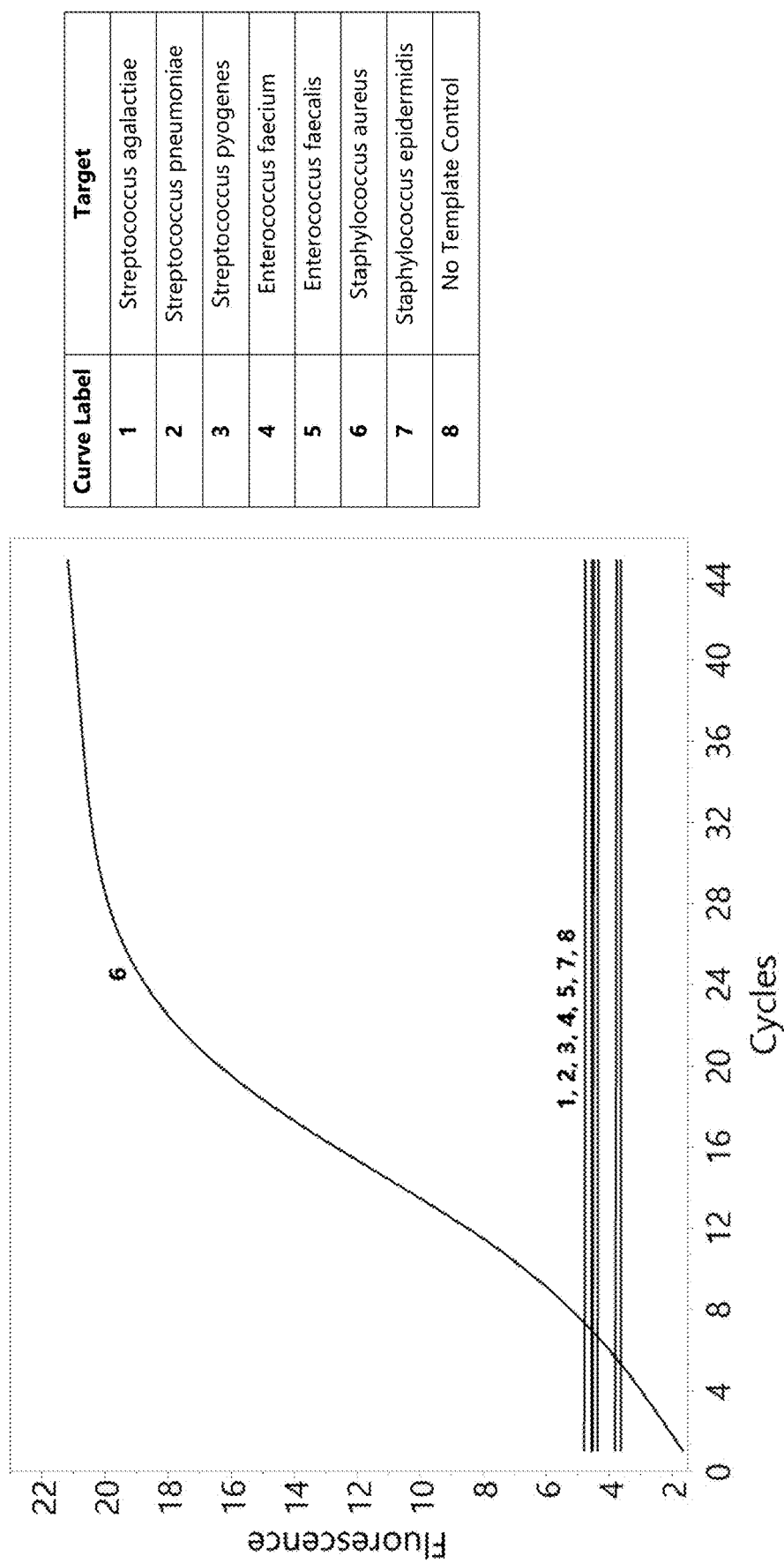
FIG. 22. PCR assays using primers and probe disclosed in TABLE XX that target the ddlA gene were tested against common Gram-positive pathogens. Growth curve is observed only for pathogens within the species *Staphylococcus aureus*. No meaningful amplification was observed for non-target organisms.

Similar results were obtained in PCR assays using forward primer SEGP2792 (SEQ ID NO: 73), reverse primer SEGP2793 (SEQ ID NO: 74), and probe SEGP2794 (SEQ ID NO: 75) that target the gyrB gene (as shown in FIG. 21), and in PCR assays using forward primer SEGP2932 (SEQ ID NO: 76), reverse primer SEGP2933 (SEQ ID NO: 77) and probe SEGP2935 (SEQ ID NO: 78) that target the ddlA gene (as shown in FIG. 22). These experiments demonstrate good inclusivity and exclusivity profiles for both combinations of primers and probes for detecting *S. aureus.*

Example 8 PCR Using Primers/Probes for Detecting *Streptococcus agalactiae*

Figure 23:
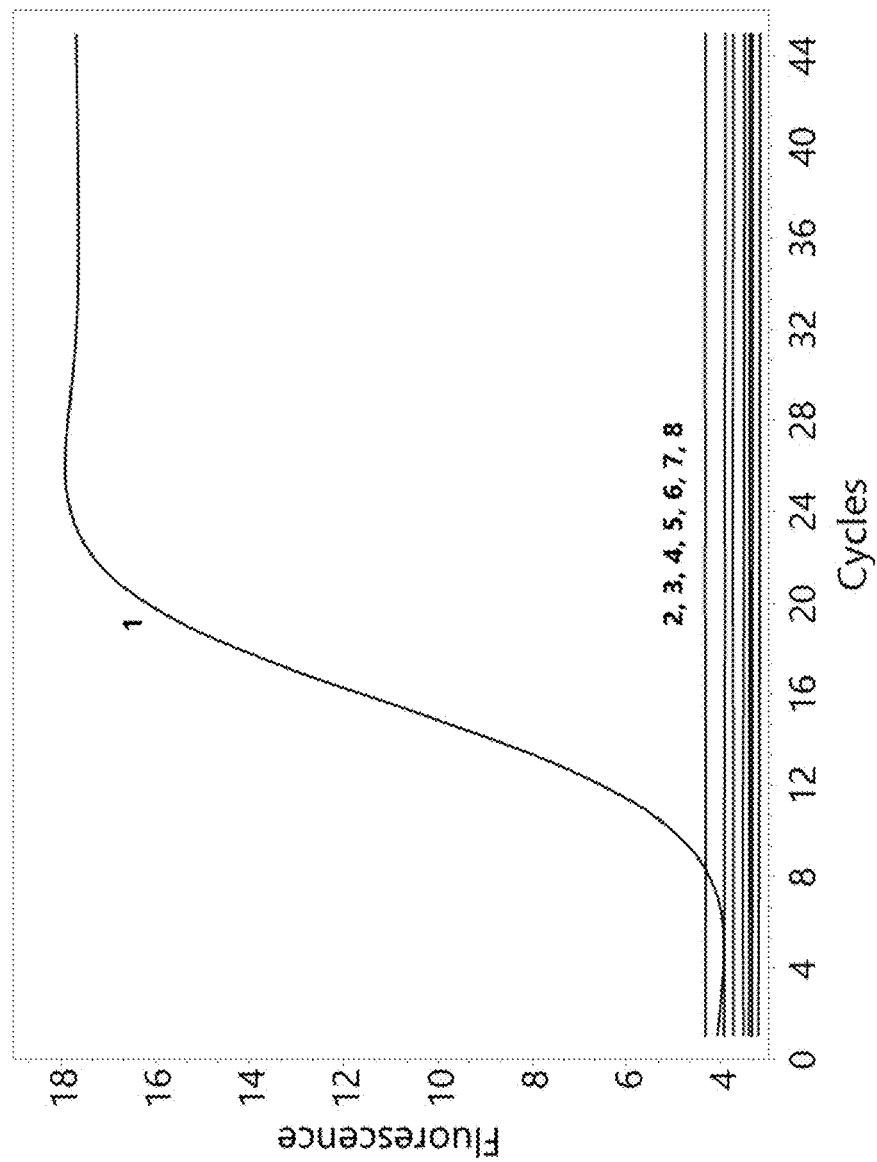
FIG. 23. PCR assays using primers and probe disclosed in TABLE XXII that target the gyrB gene were tested against common Gram-positive pathogens: *S. agalactiae, S. pneumoniae, S. pyogenes, E. faecium, E. faecalis, S. aureus*, and *S. epidermidis*. Growth curve is observed only for pathogens within the species *Streptococcus agalactiae*. No meaningful amplification was observed for non-target organisms.

PCR assays using forward primer SEGP2921 (SEQ ID NO: 121), reverse primer SEGP2922 (SEQ ID NO: 122) and probe SEGP2923 (SEQ ID NO: 123) that target the gyrB gene were tested against common Gram-positive pathogens: *S. agalactiae, S. pneumoniae, S. pyogenes, E. faecium, E. faecalis, S. aureus,* and *S. epidermidis.* Gram-negative organisms were also tested and showed no meaningful amplification (data not shown). The concentration of the genomic DNA was roughly 2-10 ng/uL for all samples, besides the no template control that was 0 ng/uL. As shown on FIG. 23, meaningful growth curves were observed only for pathogens within the species *Streptococcus agalactiae.* No meaningful amplification was observed for non-target organisms (*S. pneumoniae, S. pyogenes, E. faecium, E. faecalis, S. aureus,* and *S. epidermidis*), thereby demonstrating good inclusivity and exclusivity profiles for this particular combination of primers and probes for detecting *S. agalactiae.*

Figure 24:
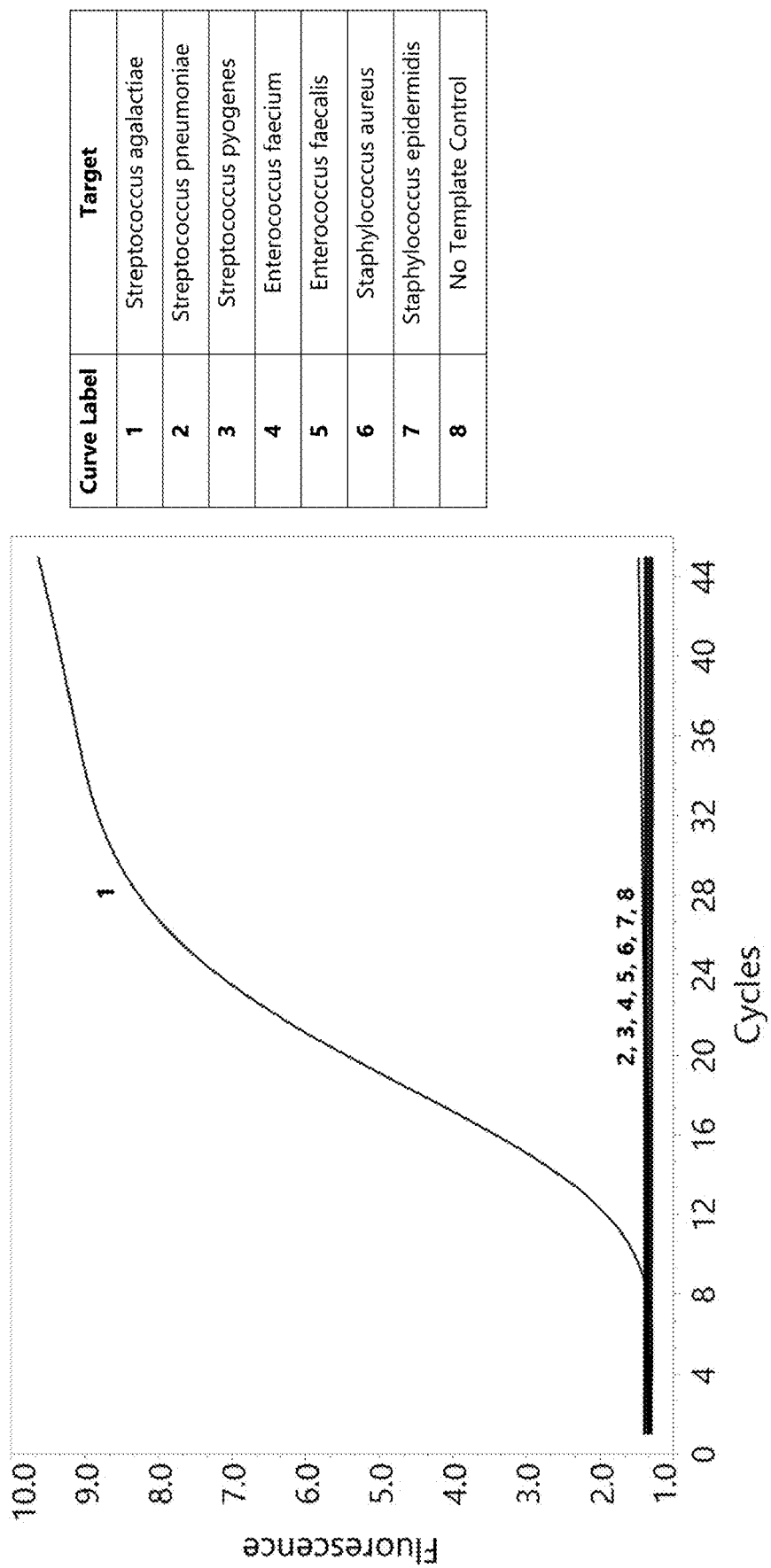
FIG. 24. PCR assays using primers and probe disclosed in TABLE XXIII that target the sip gene were tested against common Gram-positive pathogens. Growth curve is observed only for pathogens within the species *Streptococcus agalactiae*. No meaningful amplification was observed for non-target organisms.
Figure 25:
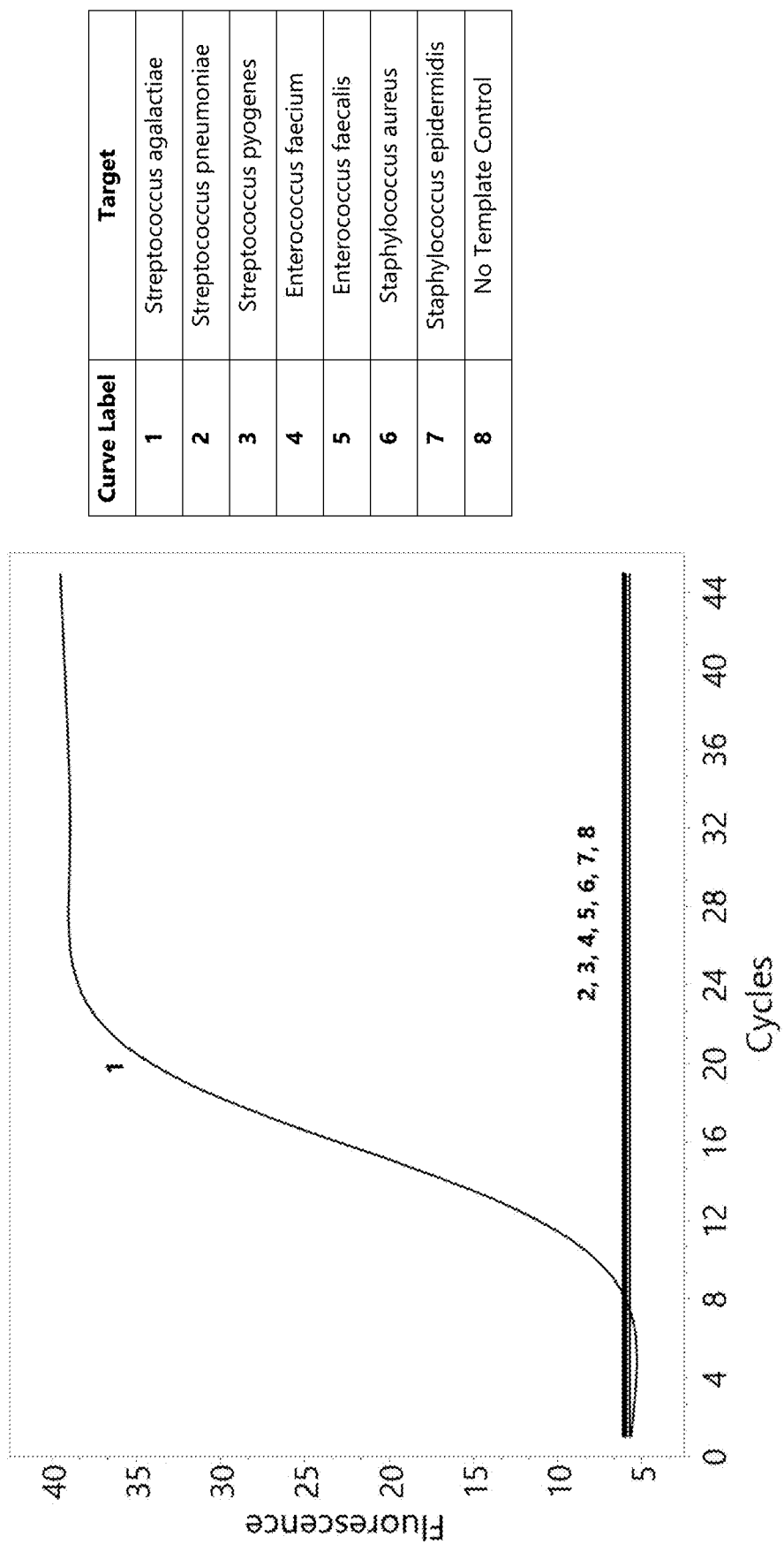
FIG. 25. PCR assays using primers and probe disclosed in TABLE XXIV that target the ddlA gene were tested against common Gram-positive pathogens. Growth curve is observed only for pathogens within the species *Streptococcus agalactiae*. No meaningful amplification was observed for non-target organisms.

Similar results were obtained in PCR assays using forward primer SEGP2204 (SEQ ID NO: 82), reverse primer SEGP2205 (SEQ ID NO: 83), and probe SEGP2206 (SEQ ID NO: 84) that target the sip gene (as shown in FIG. 24), and in PCR assays using forward primer SEGP2947 (SEQ ID NO: 85), reverse primer SEGP2949 (SEQ ID NO: 86) and probe SEGP2951 (SEQ ID NO: 87) that target the ddlA gene (as shown in FIG. 25). These experiments demonstrate good inclusivity and exclusivity profiles for both combinations of primers and probes for detecting *S. agalactiae.*

Example 9 PCR Using Primers/Probes for Detecting *Candida* Genus

Figure 26:
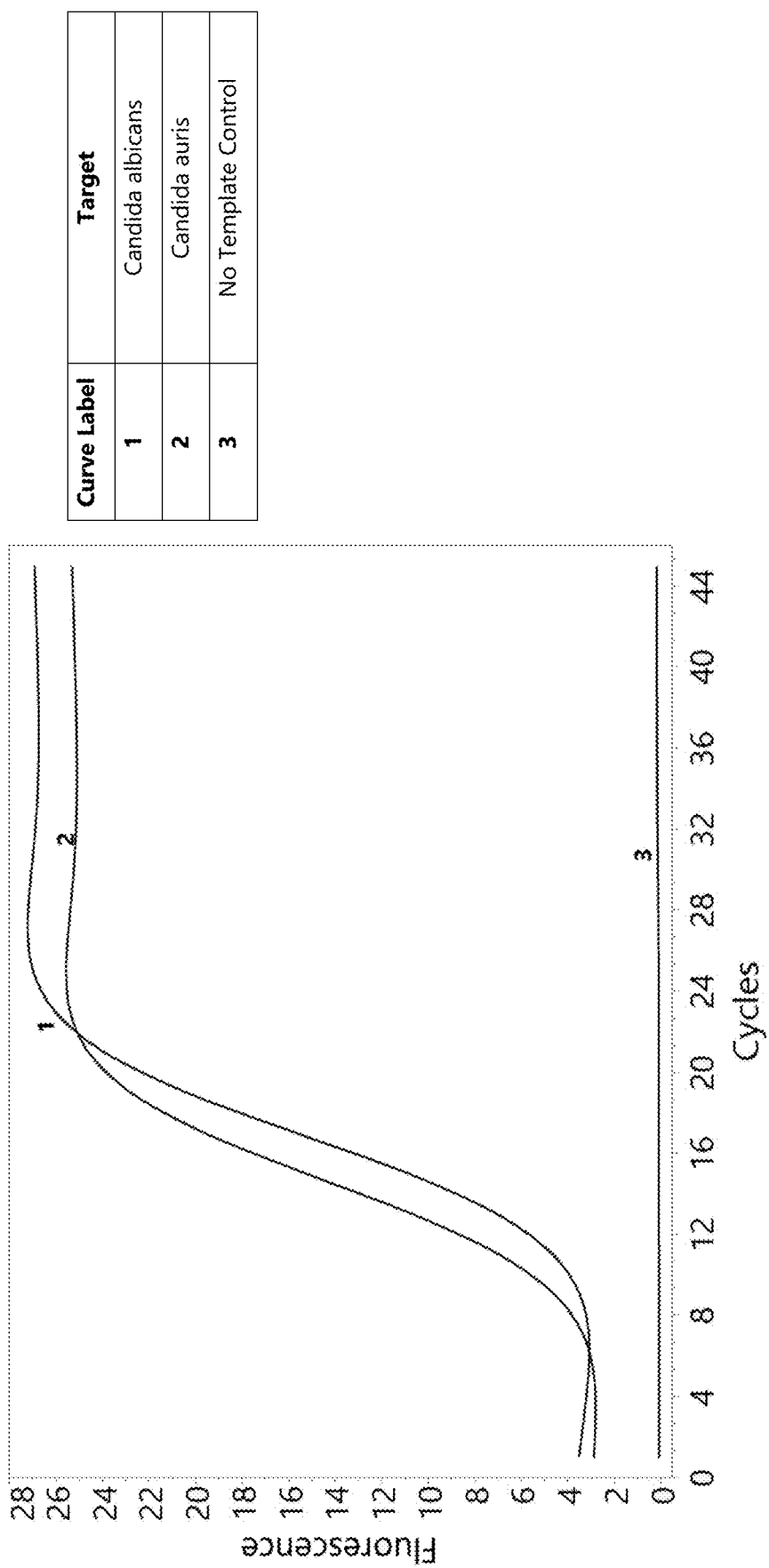
FIG. 26. PCR assays using primers and probe disclosed in TABLE XXVI that target the RDN18 (18 s rRNA) gene were tested against common fungal pathogens: *C. albicans* and *C. auris*. Growth curves are observed only for pathogens within the genus *Candida*. Gram-negative and positive organisms were also tested and showed no meaningful amplification (data not shown).

PCR assays using forward primer SEGP1712 (SEQ ID NO: 88), reverse primer SEGP1713 (SEQ ID NO: 89), and probe SEGP1716 (SEQ ID NO: 90) that target the RDN18 (18 s rRNA) were tested against common fungal pathogens: *Candida albicans* and *Candida auris.* Gram-negative and positive organisms were also tested and showed no meaningful amplification (data not shown). The concentration of the genomic DNA was roughly 2-10 ng/uL for all samples, besides the no template control that was 0 ng/uL. As shown in FIG. 26, meaningful amplification curves were observed only for pathogens within the genus *Candida.* No meaningful amplification was observed for non-target organisms, thereby demonstrating good inclusivity and exclusivity profiles for this particular combination of primers and probes for detecting *Candida.*

Figure 27:
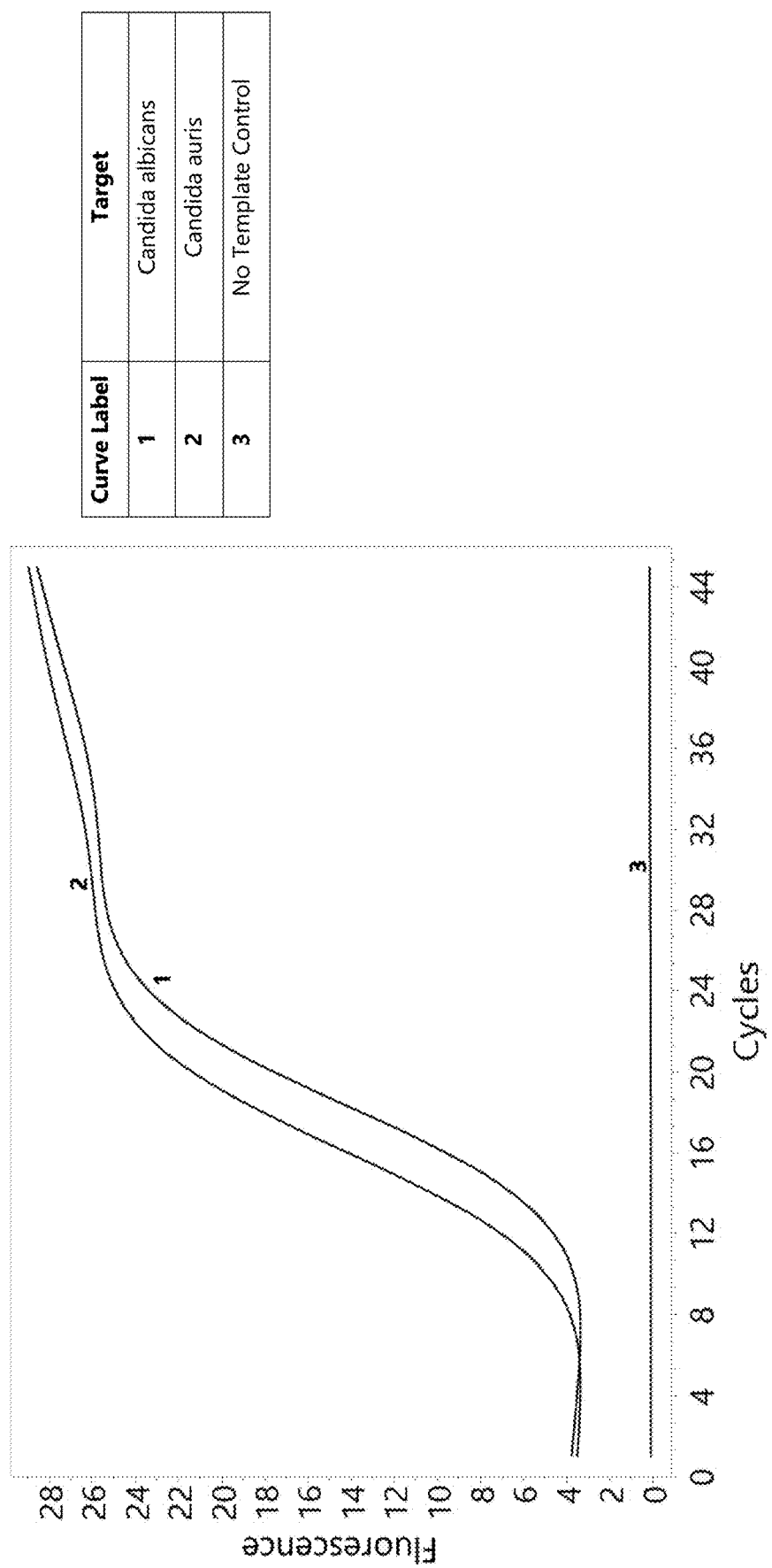
FIG. 27. PCR assays using primers and probe disclosed in TABLE XXVII that target the RDN58 (5.8 srRNA) gene were tested against common fungal pathogens: *C. albicans* and *C. auris*. Growth curves are observed only for pathogens within the genus *Candida*. Gram-negative and positive organisms were also tested and showed no meaningful amplification (data not shown).

PCR assays using forward primer SEGP1718 (SEQ ID NO: 91), reverse primer SEGP1719 (SEQ ID NO: 92), and probe SEGP1722.1 (SEQ ID NO: 93) that target the RDN58 (5.8 s rRNA) gene were tested against *C. albicans* and *C. auris.* Gram-negative and positive organisms were also tested and showed no meaningful amplification (data not shown). The concentration of the genomic DNA was roughly 2-10 ng/uL for all samples, besides the no template control that was 0 ng/uL. As shown in FIG. 27, meaningful amplification curves were observed only for pathogens within the genus *Candida.* No meaningful amplification was observed for non-target organisms, thereby demonstrating good inclusivity and exclusivity profiles for this particular combination of primers and probes for detecting *Candida.*

Example 10 PCR for Detecting Common Gram-Negative and Gram-Positive Pathogens

Figure 28:
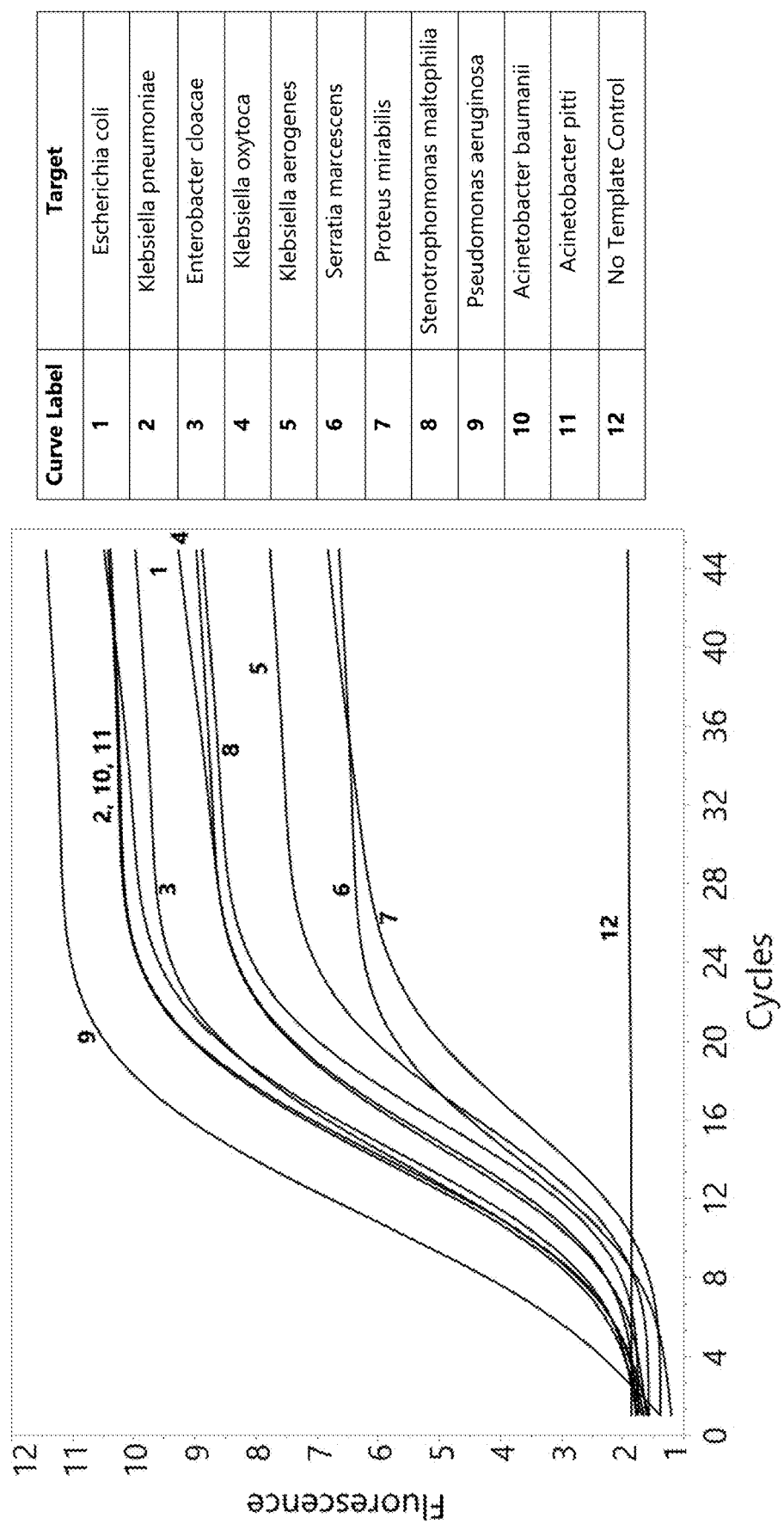
FIG. 28. PCR assays using primers and probe disclosed in TABLE XXVIII that target the 16 s gene were tested against common Gram-negative pathogens: *E. coli, K. pneumoniae, E. cloacae, K. oxytoca, K. aerogenes, S. marcescens, P. mirabilis, S. maltophilia, P. aeruginosa, A. baumannii*, and *A. pittii*. Growth curves are observed for all Gram-negative pathogens.

PCR assays using forward primer SEGP1830 (SEQ ID NO: 94), reverse primer SEGP1831 (SEQ ID NO: 95) and probe SEGP1895.1 (SEQ ID NO: 96) that target the 16 s gene were tested against common Gram-negative pathogens: *E. coli, K. pneumoniae, E. cloacae, K. oxytoca, K. aerogenes, S. marcescens, P. mirabilis, S. maltophilia, P. aeruginosa, A. baumannii,* and *A. pittii.* The concentration of the genomic DNA was roughly 2-10 ng/uL for all samples, besides the no template control that was 0 ng/uL. As shown on FIG. 28, amplification curves were observed for all Gram-negative pathogens, thereby demonstrating this particular combination of primers and probes for the detection of common Gram-negative pathogens.

Figure 29:
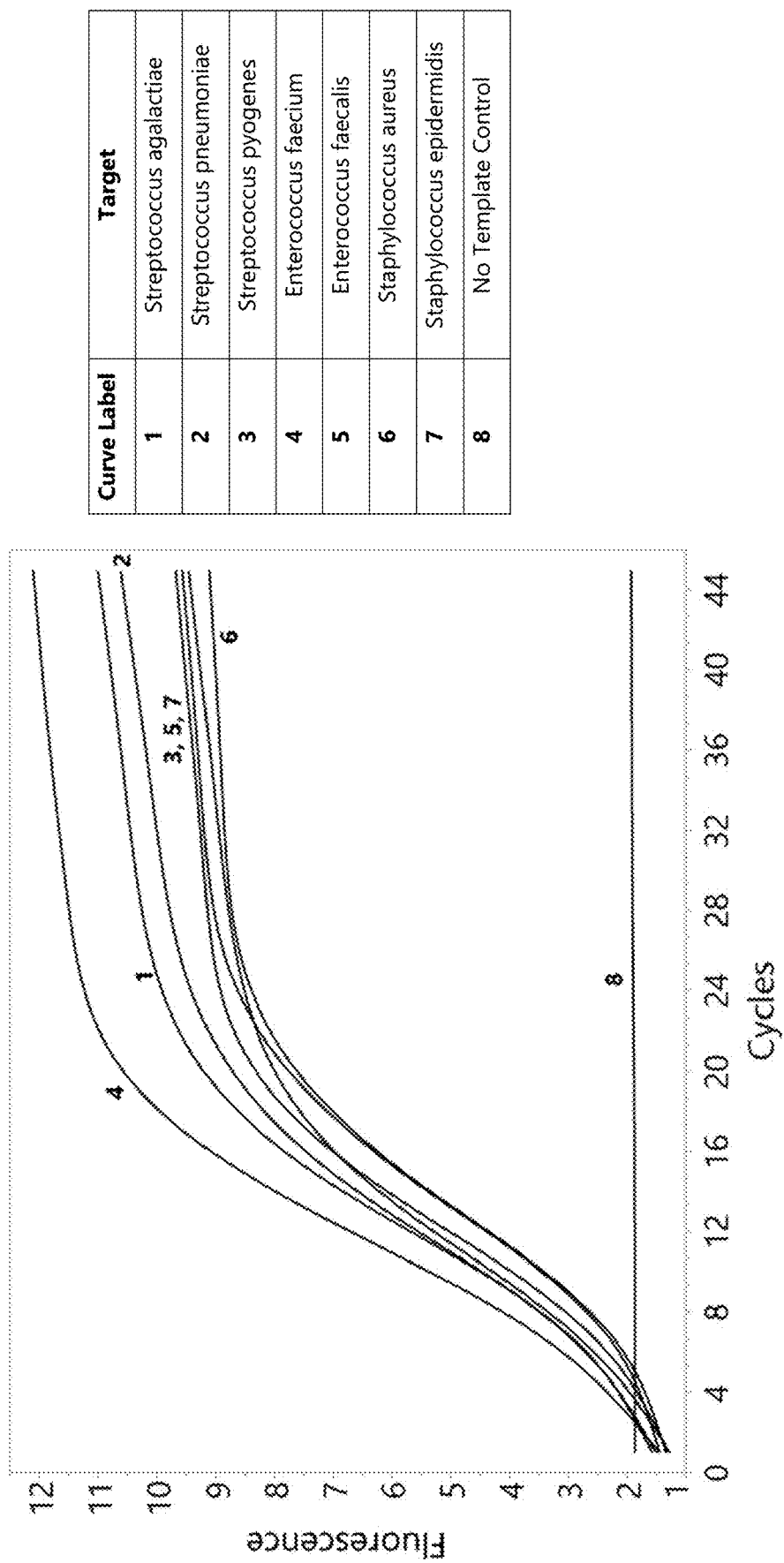
FIG. 29. PCR assays using primers and probe disclosed in TABLE XXVIII that target the 16 s gene were tested against common Gram-positive pathogens: *S. agalactiae, S. pneu-*

This same combination of primers and probe that target the 16 s gene was also tested against common Gram-positive pathogens: S. agalactiae, S. pneumoniae, S. pyogenes, E. faecium, E. faecalis, S. aureus, and S. epidermidis under identical concentrations. As shown on FIG. 29, amplification curves were observed for all Gram-positive pathogens, thereby demonstrating this particular combination of primers and probes for the detection of common Gram-positive pathogens.

Example 11 Interpretation of AST Results

In general, the two most commonly used guidelines for interpreting Antimicrobial Susceptibility Testing (AST) results are guidelines from the: 1) Clinical Laboratory Standards Institute (CLSI), and 2) European Committee on Antimicrobial Susceptibility Testing (EUCAST). The US uses the CLSI guidelines while the European countries use the EUCAST guidelines. The current version from CLSI is M100 ED30, "Performance Standards for Antimicrobial Susceptibility Testing, 30$^{th}$ Edition", and available via URL: clsi.org/standards/products/microbiology/documents/m100. The current version from EUCAST is Version 10, "The European Committee on Antimicrobial Susceptibility Testing. Breakpoint tables for interpretation of MICs and zone diameters. Version 10.0, 2020" and available via URL: www.eucast.org/fileadmin/src/media/PDFs/EUCAST_files/Breakpoint_tables/v_10.0_Breakpo int_Tables.pdf.

In FIGS. 30-1 and 30-2, the established Minimum Inhibitory Concentration (MIC) breakpoints indicated as g/mL for a number of Gram-negative bacterial organisms (Enterobacterales order, P. aeruginosa, Acinetobacter genus, S. maltophilia) as determined by the Clinical and Laboratory Standards Institute (CLSI) document M100 ED 30. Breakpoints are used to interpret MIC results from Antimicrobial Susceptibility Testing, and to classify "groupings" of organisms as either Susceptible, Intermediate, or Resistant (SIR) to a given antimicrobial. Groupings of organisms can be at differing levels, including, but not limited to, species, genus, order, or a specific biochemical property.

In FIG. 31, the established Minimum Inhibitory Concentration (MIC) breakpoints indicated as µg/mL for a number of Gram-positive bacterial organisms (S. aureus and S. lugdunensis, S. epidermidis, Enterococcus genus, S. pneumonia, Streptococcus/β-hemolytic, Viridans Streptococcus) as determined by the Clinical and Laboratory Standards Institute (CLSI) document M100 ED 30. Breakpoints are used to interpret MIC results from Antimicrobial Susceptibility Testing, and to classify "groupings" of organisms as either Susceptible, Intermediate, or Resistant (SIR) to a given antimicrobial. Groupings of organisms can be at differing levels, including, but not limited to, species, genus, order, or a specific biochemical property.

In FIG. 32, the established Minimum Inhibitory Concentration (MIC) breakpoints indicated as g/mL for fungal organisms (Candida albicans, Candida glabrata, Candida krusei, Candida tropicalis, Candida auris) as determined by the Clinical and Laboratory Standards Institute (CLSI) document M60 ED 1. Breakpoints are used to interpret MIC results from Antifungal Susceptibility Testing (AFST), and to classify "groupings" of organisms as either Susceptible, Intermediate, or Resistant (SIR) to a given antifungal. Groupings of organisms can be at differing levels, including, but not limited to, species, genus, order, or a specific biochemical property. Of note is that while AFST is recommended for Candida auris, neither CLSI or CDC currently have established breakpoints for the species; instead, AFST results from closely related Candida spp. and expert opinion are used to determine the susceptibility of C. auris isolates to a given antifungal.

Example 12 PCR ID/AST Assay Protocol

Methods and Materials:
a. Prepare antimicrobial (Abx) Plate ahead of time and store at −80° C. until needed
  i. Diluent—Cation Adjusted Mueller Hinton Broth (CAMHB)
  ii. Final Vol—50 ul/well
  iii. Remove from −80° C. and let thaw at 30 min/Room Temp prior to use

TABLE XXXI

Antimicrobial (Abx) Plate Layout
Antibiotic (Abx) Plate Layout

|   | 1 | 2 | 3 | 4 | 5 | 6 | 7 | 8 | 9 | 10 | 11 | 12 |
|---|---|---|---|---|---|---|---|---|---|----|----|----|
| A | 0 Abx | ¼ Abx | ½ Abx | 1 Abx | 2 Abx | 4 Abx | 0 Abx | ¼ Abx | ½ Abx | 1 Abx | 2 Abx | 4 Abx |
| B | 0 Abx | ¼ Abx | ½ Abx | 1 Abx | 2 Abx | 4 Abx | 0 Abx | ¼ Abx | ½ Abx | 1 Abx | 2 Abx | 4 Abx |
| C | 0 Abx | ¼ Abx | ½ Abx | 1 Abx | 2 Abx | 4 Abx | 0 Abx | ¼ Abx | ½ Abx | 1 Abx | 2 Abx | 4 Abx |
| D | 0 Abx | ¼ Abx | ½ Abx | 1 Abx | 2 Abx | 4 Abx | 0 Abx | ¼ Abx | ½ Abx | 1 Abx | 2 Abx | 4 Abx |
| E | 0 Abx | ¼ Abx | ½ Abx | 1 Abx | 2 Abx | 4 Abx | 0 Abx | ¼ Abx | ½ Abx | 1 Abx | 2 Abx | 4 Abx |
| F | 0 Abx | ¼ Abx | ½ Abx | 1 Abx | 2 Abx | 4 Abx | 0 Abx | ¼ Abx | ½ Abx | 1 Abx | 2 Abx | 4 Abx |
| G | 0 Abx | ¼ Abx | ½ Abx | 1 Abx | 2 Abx | 4 Abx | 0 Abx | ¼ Abx | ½ Abx | 1 Abx | 2 Abx | 4 Abx |
| H | 0 Abx | ¼ Abx | ½ Abx | 1 Abx | 2 Abx | 4 Abx | 0 Abx | ¼ Abx | ½ Abx | 1 Abx | 2 Abx | 4 Abx | b. Overnight cultures in CAMHB—37° C./16-18 hrs/500 rpm
  i. 10 ul glycerol stock+490 ul CAMHB in 2 mL 96-well Deep Well Plate
c. Normalize cultures to 1.00 E+06 CFU/mL by Optical Density (OD)
d. Prepare Test Plate by adding 50 ul normalized test isolate to appropriate wells of Abx Plate as outlined

TABLE XXXII

Test Isolate Layout on Abx Plate
Test Isolate Layout on Antibiotic (Abx) Plate

|   | 1 | 2 | 3 | 4 | 5 | 6 | 7 | 8 | 9 | 10 | 11 | 12 |
|---|---|---|---|---|---|---|---|---|---|----|----|----|
| A |   |   | Isolate_1 |   |   |   |   |   | Isolate_9  |   |   |   |
| B |   |   | Isolate_2 |   |   |   |   |   | Isolate_10 |   |   |   |
| C |   |   | Isolate_3 |   |   |   |   |   | Isolate_11 |   |   |   |
| D |   |   | Isolate_4 |   |   |   |   |   | Isolate_12 |   |   |   |
| E |   |   | Isolate_5 |   |   |   |   |   | Isolate_13 |   |   |   |
| F |   |   | Isolate_6 |   |   |   |   |   | Isolate_14 |   |   |   |

TABLE XXXII-continued

Test Isolate Layout on Abx Plate
Test Isolate Layout on Antibiotic (Abx) Plate

| | 1 | 2 | 3 | 4 | 5 | 6 | 7 | 8 | 9 | 10 | 11 | 12 |
|---|---|---|---|---|---|---|---|---|---|---|---|---|
| G | | | Isolate_7 | | | | | | Isolate_15 | | | |
| H | | | Isolate_8 | | | | | | Isolate_16 | | | | e. Incubate Test Plate at 37° C./4 hrs/no shaking
f. Prepare PCR Reagents according to TABLE XXIX.
g. Add 45 ul Master Mix to each well of a PCR Assay Plate
h. Following incubation, stamp 5 ul/well of Test Plate to PCR Assay Plate
i. Final Vol—50 ul/well
i. For Test Plate, continue incubating at 37° C./12-16 hrs/no shaking to determine reference method Minimum Inhibitory Concentration (MIC)
j. Load PCR Assay Plate to cobas z 480 instrument and run under conditions of TABLE XXX.
k. Following incubation read Test Plate for MIC and determine phenotypic Susceptible/Intermediate/Resistant interpretation.

Example 13 Real-Time PCR ID and AST Assay of Enterobacterales Order

Rapid identification and phenotypic antimicrobial susceptibility testing of Enterobacterales utilizing three distinct target genes, gyrB, rplP, and rpoB, and three classes of antibacterial agents ciprofloxacin (fluoroquinolone), gentamicin (aminoglycoside), and meropenem (carbapenem) was performed. The primer/probe sets used were as follows. For gyrB, SEQ ID NO: 8 (forward primer), SEQ ID NO: 9 (reverse primer), SEQ ID NO: 10 (probe); for rplP, SEQ ID NO: 5 (forward primer), SEQ ID NO: 6 (reverse primer), SEQ ID NO: 7 (probe); for rpoB, SEQ ID NO: 11 (forward primer), SEQ ID NOs: 12-14 (reverse primers), SEQ ID NOs: 15-16 (probe). The antimicrobial susceptibility of K. pneumoniae strains 0143 (antimicrobial resistant strain) and 16565 (antimicrobial sensitive strain) were interpreted according to the Clinical and Laboratory Standards Institute (CLSI) document M100 ED 30 to determine their resistance and susceptibility to the given antimicrobials, respectively. Each strain was inoculated at 5E5 CFU/mL into wells containing various concentrations of the indicated antimicrobials, and after 4 h of incubation were subjected to PCR-based rapid ID/AST testing using the protocol of Example 12.

The results are shown on FIG. 33. The percentages on the Y-axis depicted as "Fold Change Abx level 1" were determined using the calculation $2^{\wedge}-(Abx\_Level\_1\_Ct-Reference\_Ct)$ or $2^{\wedge}-(\Delta Ct)$. The Abx Level indication does not relate to an actual concentration that was used but is rather an indication of which 2-fold dilution is being referred to where Abx Level 1 is the lowest concentration and each Level up is 2-fold higher concentration (see TABLE XXXI). To give an example of how Fold Change is calculated, if the Reference_Ct value (i.e. the Ct value with no antimicrobial added) is 20 and the Abx_Level_1_Ct value is 22, then the Fold Change=$2^{\wedge}-(22-20)=2^{\wedge}-2=\frac{1}{2}\times\frac{1}{2}=25\%$. Based on these calculations, strains resistant to the antimicrobial which have lower $\Delta Ct$ values will have higher "Fold Change" values than strains that are sensitive to the antimicrobial which have higher $\Delta Ct$ values, and in FIG. 33, Abx Level 1 was able to produce the best separation between the resistant strain Kpn 0143 and the sensitive strain Kpn 16565. These data further indicate that all three gene targets (gyrB, rplB, rpoB) can be utilized to obtain correct susceptibility results for both Kpn strains, in determining sensitivity or resistance to ciprofloxacin, gentamicin, and meropenem. However, there may be instances in which any given target gene may perform better or worse for determining sensitivity or resistance to a given antimicrobial. Taken together, these results indicate that different target genes and alleles can be utilized for rapid PCR-based ID/AST of the Enterobacterales Order as long as the primers and probes can exhibit correct inclusivity and exclusivity criteria for Enterobacterales as was shown in Example 2, FIGS. 5-7.

Example 14 Real-Time PCR ID and AST Assay of Pseudomonas aeruginosa

Rapid Identification and phenotypic antimicrobial susceptibility testing of *Pseudomonas aeruginosa* utilizing three distinct target genes, tuf; gyrB, rpoB, and three classes of antibacterial agents, ciprofloxacin, gentamicin, and meropenem, was performed. The primer/probe sets used were as follows. For tuf; SEQ ID NO: 32 (forward primer), SEQ ID NO: 33 (reverse primer), SEQ ID NO: 34 (probe); for gyrB, SEQ ID NO: 35 (forward primer), SEQ ID NO: 36 (reverse primer), SEQ ID NO: 37 (probe); for rpoB, SEQ ID NO: 38 (forward primer), SEQ ID NO: 39 (reverse primer), SEQ ID NO: 40 (probe). The antimicrobial susceptibility of *P. aeruginosa* strains 16657 (resistant) and 17816 (sensitive) were interpreted according to the Clinical and Laboratory Standards Institute (CLSI) document M100 ED 30 to determine their resistance and susceptibility to the given antimicrobials, respectively. Each strain was inoculated at 5E5 CFU/mL into wells containing various concentrations of the indicated antimicrobials, and after 4 h of incubation were subjected to PCR-based rapid ID/AST testing using the protocol of Example 12. The results, as shown in FIG. 34, indicate that all three gene targets can be utilized to obtain correct susceptibility results for both *P. aeruginosa* strains, though some target alleles do seem to perform better for some antimicrobials. Taken together, these results indicate that different target genes and alleles can be utilized for rapid PCR-based ID/AST given they provide the correct inclusivity and exclusivity criteria for *P. aeruginosa* (see FIGS. 11-13).

Example 15 Real-Time PCR ID and AST Assay of Acinetobacter baumanii

Rapid Identification and phenotypic antimicrobial susceptibility testing of *Acinetobacter baumanii* utilizing three distinct target genes, ompA, rpoB, gyrB, and three classes of antibacterial agents, ciprofloxacin, gentamicin, and meropenem, was performed. The primer/probe sets used were as follows. For ompA, SEQ ID NO: 20 (forward primer), SEQ ID NO: 21 (reverse primer), SEQ ID NO: 22 (probe); for rpoB, SEQ ID NO: 23 (forward primer), SEQ ID NO: 24 (reverse primer), SEQ ID NO: 25 (probe); for gyrB, SEQ ID NO: 26 (forward primer), SEQ ID NO: 27 (reverse primer), SEQ ID NO: 28 (probe). The antimicrobial susceptibility of *A. baumannii* strains 17694 (resistant) and 16421 (sensitive) were interpreted according to the Clinical and Laboratory Standards Institute (CLSI) document M100 ED 30 to determine their resistance and susceptibility to the given antimicrobials, respectively. Each strain was inoculated at 5E5 CFU/mL into wells containing various concentrations of the indicated antimicrobials, and after 4 h of incubation were subjected to PCR-based rapid ID/AST testing using the protocol of Example 12. The results, as shown in FIG. 35, indicate that all three gene targets can be utilized to obtain correct susceptibility results for both Abi strains, though some target alleles do seem to perform better for some antimicrobials. Taken together, these results indicate that different target genes and alleles can be utilized for rapid PCR-based ID/AST given they provide the correct inclusivity and exclusivity criteria for *A. baumannii* (see FIGS. 8-10).

Example 16 Real-Time PCR ID and AST Assay of *Staphylococcus aureus*

Rapid Identification and phenotypic antimicrobial susceptibility testing of *Staphylococcus. aureus* utilizing three distinct target genes (gyrB, ddlA, tuf) and one class of antibacterial agent, cefoxitin (cephalosporin) was performed. The primer/probe sets used were as follows. For gyrB, SEQ ID NO: 73 (forward primer), SEQ ID NO: 74 (reverse primer), SEQ ID NO: 75 (probe); for ddlA, SEQ ID NO: 76 (forward primer), SEQ ID NO: 77 (reverse primer), SEQ ID NO: 78 (probe); for tuf; SEQ ID NO: 79 (forward primer), SEQ ID NO: 80 (reverse primer), SEQ ID NO: 81 (probe). The antimicrobial susceptibility of *S. aureus* strains 15509 (resistant) and 16405 (sensitive) were interpreted according to the Clinical and Laboratory Standards Institute (CLSI) document M100 ED 30 to determine their resistance and susceptibility to the given antimicrobials, respectively. Each strain was inoculated at 5E5 CFU/mL into wells containing various concentrations of the indicated antimicrobial, and after 4 h of incubation were subjected to PCR-based rapid ID/AST testing using the protocol of Example 12. The results, as shown in FIG. 36, indicate that all three gene targets can be utilized to obtain correct susceptibility results for both *S. aureus* strains, though some target alleles do seem to perform better. Taken together, these results indicate that different target genes and alleles can be utilized for rapid PCR-based ID/AST given they provide the correct inclusivity and exclusivity criteria for *S. aureus* (see FIGS. 21-22).

Example 17 Real-Time PCR ID and AST Assay of *Enterococcus faecium*

Rapid Identification and phenotypic antimicrobial susceptibility testing of *Enterococcus faecium* utilizing three distinct target genes (rpoB, ddl, gyrB) and two classes of antibacterial agents, ampicillin (beta-lactam) and vancomycin (glycopeptide) was performed. The primer/probe sets used were as follows. For rpoB, SEQ ID NO: 53 (forward primer), SEQ ID NO: 54 (reverse primer), SEQ ID NO: 55 (probe); for ddl, SEQ ID NOs: 56-57 (forward primers), SEQ ID NOs: 58-59 (reverse primers), SEQ ID NOs: 60-61 (probes); for gyrB, SEQ ID NOs: 62-63 (forward primers), SEQ ID NOs: 64-65 (reverse primers), SEQ ID NO: 66 (probe). The antimicrobial susceptibility of *E. faecium* strains 18483 (resistant) and 18446 (sensitive) were interpreted according to the Clinical and Laboratory Standards Institute (CLSI) document M100 ED 30 to determine their resistance and susceptibility to the given antimicrobials, respectively. Each strain was inoculated at 5E5 CFU/mL into wells containing various concentrations of the indicated antimicrobial, and after 4 h of incubation were subjected to PCR-based rapid ID/AST testing using the protocol of Example 12. The results, as shown in FIG. 37, indicate that all three gene targets can be utilized to obtain correct susceptibility results for both *E. faecium* strains, though some target alleles do seem to perform better. Taken together, these results indicate that different target genes and alleles can be utilized for rapid PCR-based ID/AST given they provide the correct inclusivity and exclusivity criteria for *E. faecium* (see FIGS. 17-19).

Example 18 Real-Time PCR ID and AST Assay of *Candida* Genus

Rapid Identification and phenotypic antimicrobial susceptibility testing of *Candida* can be performed with the target genes RDN18 (18 s ribosomal RNA) and RDN58 (5.8 s ribosomal RNA) using the primers and probes as shown in FIG. 38 which are for RDN18: SEQ ID NO: 88 (forward primer), SEQ ID NO: 89 (reverse primer), SEQ ID NO: 90 (probe); and for RDN58: SEQ ID NO: 91 (forward primer), SEQ ID NO: 92 (reverse primer), SEQ ID NO: 93 (probe). The correct inclusivity and exclusivity criteria for *Candida* are shown in FIGS. 26-27.

Example 19 Generic Real-Time PCR ID and AST Assay

Rapid Identification and phenotypic antimicrobial susceptibility testing of any given Gram-negative or Gram-positive bacteria can be performed with the widely conserved 16 s ribosomal RNA gene as target and using the primers and probe as shown in FIG. 39, which are SEQ ID NO: 94 (forward primer), SEQ ID NO: 95 (reverse primer), and SEQ ID NO: 96 (probe).

Example 20 Multiplex PCR ID Assay with Breakpoint Groups

FIG. 40A shows the inclusivity and exclusivity performance of a Gram-negative pathogen PCR multiplex master mix. The *Acinetobacter* PCR detection set utilized forward primer SEGP2603 (SEQ ID NO: 20), reverse primer SEGP2606 (SEQ ID NO: 21) and probe SEGP2769 (SEQ ID NO: 22) that targets the ompA gene (see TABLE V) and assay results are reported in channel 1. The *Pseudomonas aeruginosa* PCR detection set utilized forward primer SEGP2341 (SEQ ID NO: 32), reverse primer SEGP2342 (SEQ ID NO: 33) and probe SEGP2343 (SEQ ID NO: 34) that targets the tuf gene (see TABLE VIII) and assay results are reported in channel 2. The Enterobacterales PCR detection set utilized forward primer SEGP1899 (SEQ ID NO: 8), reverse primer SEGP1901 (SEQ ID NO: 9) and probe SEGP2016 (SEQ ID NO: 10) and targets the gyrB gene (see TABLE III) and assay results are reported in channel 3. General bacterial PCR detection set utilized forward primer SEGP1830 (SEQ ID NO: 94), reverse primer SEGP1831 (SEQ ID NO: 95) and probe SEGP1895.1 (SEQ ID NO: 96) targets the 16 s rRNA gene (see TABLE XXVIII) and assay results are reported in channel 4. Lastly, a generic internal control PCR detection set utilized forward primer SEGP1952 (ACAACCGCGCCATACATGTCAAGA<t_BB_dC>; SEQ ID NO: 97), reverse primer SEGP1953 (GTCGGGCCGCTTATACAGTACCA<t_BB_dC>; SEQ ID NO: 98) and probe SEGP1954 (<CY5.5>TGCGCGTCCCG<BHQ_2>TTTTGATACTTC GTAACGGTGC<Phos>; SEQ ID NO: 99) and assay results are reported in channel 5. The breakpoint groups, channels, and dye wavelengths are summarized in FIG. 40B. The concentration of the genomic DNA was roughly 2-10 ng/uL for all samples. The multiplex reaction was tested against genomic DNA isolated from common Gram-negative pathogens: *E. coli*, *K. pneumoniae*, *E. cloacae*, *K. oxytoca*, *K. aerogenes*, *S. marcescens*, *P. mirabilis*, *S. maltophilia*, *P. aeruginosa*, *A. baumannii*, and *A. pittii*. Additionally, no meaningful amplification was observed with genomic DNA isolated from common Gram-positive pathogens (data not shown). As designed, amplification curves are observed in the correct channel for desired pathogens, indicating the multiplex reaction has very strong inclusivity and exclusivity.

FIG. 41A shows the inclusivity and exclusivity performance of a Gram-positive pathogen PCR multiplex master mix. The *Streptococcus* PCR detection set utilized forward primer SEGP1705 (SEQ ID NO: 100), reverse primer SEGP1706 (SEQ ID NO: 101) and probe SEGP1709.1 (SEQ ID NO: 102) that targets the tuf gene (see TABLE XXV) and assay results are reported in channel 1. The *Staphylococcus* PCR detection set utilized forward primer SEGP1835 (SEQ ID NO: 79), reverse primer SEGP1836 (SEQ ID NO: 80) and probe SEGP1838 (SEQ ID NO: 81) that targets the tuf gene (see TABLE XXI) and assay results are reported in channel 2. The *Enterococcus* PCR detection set utilized forward primer SEGP2522 (SEQ ID NO: 53), reverse primer SEGP2525 (SEQ ID NO: 54) and probe SEGP2770 (SEQ ID NO: 55) that targets the rpoB gene (see TABLE XV) and assay results are reported in channel 3. General bacterial PCR detection set utilized forward primer SEGP1830 (SEQ ID NO: 94), reverse primer SEGP1831 (SEQ ID NO: 95) and probe SEGP1895.1 (SEQ ID NO: 96) that targets the 16 s rRNA gene (see TABLE XXVIII) and assay results are reported in channel 4. Lastly, a generic internal control PCR detection set utilized forward primer SEGP1952 (SEQ ID NO: 97), reverse primer SEGP1953 (SEQ ID NO: 98) and probe SEGP1954 (SEQ ID NO: 99) and assay results are reported in channel 5. The breakpoint groups, channels, and dye wavelengths are summarized in FIG. 41B. The concentration of the genomic DNA was roughly 2-10 ng/uL for all samples. The multiplex reaction was tested against purified genomic DNA from common Gram-positive pathogens: *S. agalactiae*, *S. pneumoniae*, *S. pyogenes*, *E. faecium*, *E. faecalis*, *S. aureus*, and *S. epidermidis*. Additionally, no meaningful amplification was observed with genomic DNA isolated from common Gram-negative pathogens (data not shown). As designed, amplification curves are observed in the correct channel for desired pathogens, indicating the multiplex reaction has very strong inclusivity and exclusivity.

Example 21 Analysis of PCR-AST Assay

FIG. 42 contains graphs from a series of PCR-AST assays on diverse Gram-negative strains showing different thresholds that can be used to distinguish between susceptible and resistant isolates of multiple pathogen groups separated into different channels and interpreted using statistical separation of populations as outlined in FIG. 4. The thresholds associated with ciprofloxacin susceptibility are shown for A) *Acinetobacter baumannii* (Abi) using primers/probe of SEQ ID NOs: 17-19 that target the ompA gene, B) Enterobacteriaceae (Entero) using primers/probe of SEQ ID NOs: 1-3 that target the rplP gene, and C) *Pseudomonas aeruginosa* (Pae) using primers/probe as shown in TABLE XXXIII and target the O-antigen acetylase gene, and are based on change in Ct value at 2 ug/mL ciprofloxacin relative to no ciprofloxacin control (ΔCt), Relative Fluorescence Intensity (RFI) at 0.5 ug/mL ciprofloxacin and ΔCt at 1 ug/mL ciprofloxacin, and Slope prior to the Ct fluorescence value at 0.5 ug/mL ciprofloxacin (Slope) and ΔCt at 1 ug/mL ciprofloxacin.

TABLE XXXIII

Oligonucleotides for detecting *Pseudomonas aeruginosa* Primers and Probes that hybridize to O-antigen acetylase gene in *P. aeruginosa*

| Oligonucleotide Type | Oligonucleotide Name | SEQ ID NO: | Sequence | Modifications |
|---|---|---|---|---|
| Forward primer | RM_PFP01 | 130 | ACGTTTTCCCTTCGCTG<t_BB_dA> | t_BB_dA = t-butylbenzyl-dA |
| Reverse primer 1 | RMPRP02 | 131 | GTACAGTGACCAGCCAT<t_BB_dC> | t_BB_dC = t-butylbenzyl-dC |
| Reverse primer 2 | RMPRP04 | 132 | GCGAAACAATCCAGGCCAT<t_BB_dC> | t_BB_dC = t-butylbenzyl-dC |
| Probe | RM_P04 | 133 | <FAM_Thr>CCTACG<BHQ_2>TGAATGCGCTGTTCGATGCGTTGGC<Phos> | <FAM_Thr>: Fluorophore <BHQ_2>: Quencher <Phos>: Phosphate |

FIG. 43A) shows the distribution of the resistant and susceptible isolates that were tested for Abi, Pae, and for the Enterobacteriaceae family subdivided into the strains *E. cloacae* (Ecl), *E. Coli* (Eco), *K. aerogenes* (Kae), and *K. pneumonia* (Kpn). The sensitivity, specificity, and categorical agreement for ciprofloxacin across species using the thresholds in FIG. 42 are shown in FIG. 43B). Sensitivity is defined as Total Positives/(Total Positives+False Negatives); Specificity is defined as Total Negatives/(Total Negatives+False Positives); Categorical Agreement is defined as (Total Positives+Total Negatives)/(Total Positives+False Negatives+Total Negatives+False Positives).

FIG. 44 contains graphs from a second PCR-AST assay where thresholds associated with gentamicin susceptibility are shown for A) Abi, B) Entero, and C) Pae, using the respective primers/probe sets, and are based on Inflection cycle at 1 ug/mL gentamicin, changes in Absolute Fluorescence Intensity (ΔAFI) at 1 ug/mL gentamicin and 8 ug/mL gentamicin, and Goodness of Fit for the curve fit to the raw fluorescence data at 16 ug/mL gentamicin and ΔAFI at 4 ug/mL gentamicin. FIG. 45A) shows the distribution of the resistant and susceptible isolates that were tested for Abi, Pae, and for the Enterobacteriaceae strains *Enterobacter cloacae* (Ecl), *Escherichia coli* (Eco), *Klebsiella aerogenes* (Kae) and *Klebsiella pneumonia* (Kpn). The sensitivity, specificity and categorical agreement for gentamicin across species using the thresholds in FIG. 44 are seen in FIG. 45B).

FIG. 46 contains graphs from a third PCR-AST assay where thresholds associated with meropenem susceptibility are shown for A) Abi, B) Entero, and C) Pae, using the respective primers/probe sets, and are based on change in Ct value at 4 ug/mL meropenem relative to no meropenem control (ΔCt), change in Ct value at 4 ug/mL meropenem relative to the lowest meropenem concentration at 0.25 ug/mL (ΔAbx-Ct) and the absolute Ct value (Ct) at 0.25 ug/mL meropenem, and the Absolute Fluorescence Intensity (AFI) at 1 ug/mL meropenem and ΔCt at 4 ug/mL meropenem. FIG. 47A) shows the distribution of the resistant and susceptible isolates that were tested for Abi, Pae, and for the Enterobacteriaceae strains Ecl, Eco, Kae and Kpn. The sensitivity, specificity and categorical agreement for gentamicin across species using the thresholds in FIG. 46 are seen in FIG. 47B).

Example 22 Multiplex ID-AST PCR Assay of Polymicrobial Samples

A. Kpn/Abi Multiplex PCR ID-AST assay was performed in a polymicrobial sample where a 1:1 ratio of two Gram-negative organisms, *Klebsiella pneumonia* (Kpn) and *Acinetobacter baumannii* (Abi) with different susceptibility combinations were co-incubated together in the absence or presence of three different antibiotics, ciprofloxacin, gentamicin and meropenem, at varying concentrations. Detection of the Kpn signal was from an ATTO-labeled probe and detection of the Abi signal was from a HEX-labeled probe. Primers and probes used in this assay are shown in TABLE XXXIV and the results are shown on FIG. 49. Each species displayed the appropriate phenotype in the corresponding detection channel as indicated by a delta-Ct threshold that separates susceptible (sensitive) and resistant strains, thereby providing accurate antimicrobial susceptibility results for this polymicrobial situation.

TABLE XXXIV

Oligonucleotides Used in Kpn and Abi ID-AST Assay
Primers and Probes used in polymicrobial ID-AST assay with *Klebsiella pneumoniae* and *Acinetobacter baumannii*

| Oligonucleotide Type | Oligonucleotide Name | SEQ ID NO: | Sequence | Modifications |
|---|---|---|---|---|
| Forward primers | SEGP1899 | 8 | TGTCGAATTCTTATGACTCCTCCAG | |
| | SEGP1813 | 29 | TAACCCTAACGCTACTGCACGT | |
| Reverse primers | SEGP1901 | 9 | CGCGAGCGCTTCGTCGA | |
| | SEGP1815 | 30 | GGTTGATCCCAAGCGAAACCT | |
| Probes | SEGP2016 | 10 | <HEX>CCGGTCTGC<ZEN>ACCACATGGTATTCGAGGTGG<3IABkFQ> | <HEX>: Fluorophore<br><ATTO>: Fluorophore |
| | SEGP1951 | 31 | <ATTO>TCGAAGGT<BHQ_2>CACACAGATAACACT<Phos> | <ZEN>: Quencher<br><BHQ_2>: Quencher<br><3IABkFQ>: 3' Blocker<br><Phos>: 3' Blocker |

FIG. 48A) describes the workflow for testing bacteria isolates directly from positive blood culture samples, which were created by spiking a fixed concentration of bacteria into whole blood, separating red blood cells, inoculating plasma containing bacteria into a commercial blood culture bottle, incubating overnight, and then following the PCR-AST assay protocol as described in EXAMPLE 12 for testing isolates known for being resistant or susceptible to gentamicin. FIG. 48B) shows the results of this experiment where the change in Ct value (ΔCt) are used to distinguish between resistant and susceptible isolates, showing that phenotypic results can be obtained on bacteria directly from positive blood culture.

B. Kpn/Sar Multiplex PCR ID-AST assay was performed in a polymicrobial sample where a 1:1 ratio of one Gram-negative organism *Klebsiella pneumonia* (Kpn) and one Gram-positive organism *Staphylococcus aureus* (Sar) with different susceptibility combinations were co-incubated together in the absence or presence of three different antibiotics, ciprofloxacin, cefoxitin and meropenem, at varying concentrations. Detection of the Kpn signal was from a HEX-labeled probe and detection of the Sar signal was from a FAM-labeled probe. Primers and probes used in this assay are shown in TABLE XXXV and the results are shown on FIG. 50. N/A indicates that there is no clinically relevant interpretation for the corresponding bacteria-drug combination. Each species displayed the appropriate phenotype in the corresponding detection channel as indicated by a delta-Ct threshold that separates susceptible (sensitive) and resistant strains, thereby providing accurate antimicrobial susceptibility results for this polymicrobial situation.

TABLE XXXV

Oligonucleotides Used in Kpn and Sar ID-AST Assay
Primers and Probes used in polymicrobial ID-AST assay with *Klebsiella pneumoniae* and *Staphylococcus aureus*

| Oligonucleotide Type | Oligonucleotide Name | SEQ ID NO: | Sequence | Modifications |
|---|---|---|---|---|
| Forward primers | SEGP1899 | 8 | TGTCGAATTCTTATGACTCCTCCAGTA | |
| | SEGP1835 | 79 | CCGTGTTGAACGTGGTCAAATCAA | |
| Reverse primers | SEGP1901 | 9 | CGCGAGCGCTTCGTCGA | |
| | SEGP1836 | 80 | AGCAGCTAATACTTGACCACGTTGTA | |
| Probes | SEGP2016 | 10 | <HEX>CCGGTCTGC<ZEN>ACCACATGGTATTCGAGGTGG<3IABkFQ> | <HEX>: Fluorophore |
| | SEGP1838 | 81 | <FAM>AGACTACGC<ZEN>TGAAGCTGGTGAC<3IABkFQ> | <FAM>: Fluorophore<br><ZEN>: Quencher<br><3IABkFQ>: 3' Blocker |

C. Kpn/Cal Multiplex PCR ID-AST assay was performed in a polymicrobial sample where a 1:1 ratio of one Gram-negative organism, *Klebsiella pneumonia* (Kpn), and one fungal organism, *Candida albicans* (Cal) with different susceptibility combinations were co-incubated together in the absence or presence of two different antibiotics, ciprofloxacin and meropenem, at varying concentrations. Detection of the Kpn signal was from a HEX-labeled probe and detection of the Cal signal was from a FAM-labeled probe. Primers and probes used in this assay are shown in TABLE XXXVI and the results are shown on FIG. 51. N/A indicates that there is no clinically relevant interpretation for the corresponding organism-drug combination. Cal susceptibility for fluconazole is indicated. The Kpn strains displayed the appropriate phenotype in the corresponding detection channel as indicated by a delta-Ct threshold that separates susceptible and resistant isolates, providing accurate antimicrobial susceptibility results.

D. Efs/Sar Multiplex PCR ID-AST assay was performed in a polymicrobial sample where a 1:1 ratio of two Gram-positive organisms, *Enterococcus faecalis* (Efs) and *Staphylococcus aureus* (Sar), with different susceptibility combinations were co-incubated together in the absence or presence of vancomycin at varying concentrations. Detection of the Efs signal was from a HEX-labeled probe and detection of the Sar signal was from a FAM-labeled probe. Primers and probes used in this assay are shown in TABLE XXXVII and the results are shown on FIG. 52. Both species displayed the appropriate phenotype in the corresponding detection channel as indicated by a delta-Ct threshold that separates susceptible and resistant isolates, providing accurate antimicrobial susceptibility results for this polymicrobial situation.

TABLE XXXVI

Oligonucleotides Used in Kpn and Cal ID-AST Assay
Primers and Probes used in polymicrobial ID-AST assay with *Klebsiella pneumoniae* and *Candida albicans*

| Oligonucleotide Type | Oligonucleotide Name | SEQ ID NO: | Sequence | Modifications |
|---|---|---|---|---|
| Forward primers | SEGP1899 | 8 | TGTCGAATTCTTATGACTCCTCCAGTA | |
| | SEGP1712 | 88 | CGTTTTCATTAATCAAGAACGAAAGTTA | |
| Reverse primers | SEGP1901 | 9 | CGCGAGCGCTTCGTCGA | |
| | SEGP1713 | 89 | ACCGATCCCTAGTCGGCATA | |
| Probes | SEGP2016 | 10 | <HEX>CCGGTCTGC<ZEN>ACCACATGGTATTCGAGGTGG<3IABkFQ> | <HEX>: Fluorophore |
| | SEGP1716 | 90 | <FAM>AGACTACGA<ZEN>CGGTATCTGATCATCTTCGATCCC<3IABkFQ> | <FAM>: Fluorophore<br><ZEN>: Quencher<br><3IABkFQ>: 3' Blocker |

TABLE XXXVII

Oligonucleotides Used in Efs and Sar ID-AST Assay
Primers and Probes used in polymicrobial ID-AST assay with Enterococcus faecalis and Staphylococcus aureus

| Oligonucleotide Type | Oligonucleotide Name | SEQ ID NO: | Sequence | Modifications |
|---|---|---|---|---|
| Forward primers | SEGP1624 | 56 | CGTAGCATTCTATGATTATGAAGCC | |
| | SEGP1835 | 79 | CCGTGTTGAACGTGGTCAAATCAAA | |
| Reverse primers | SEGP1625 | 58 | CATCGTGTAAGCTAACTTCG | |
| | SEGP1836 | 80 | AGCAGCTAATACTTGACCACGTTGTA | |
| Probes | SEGP1626 | 60 | <HEX>CAGATTCCA<ZEN>GCCGAAGT GCC<3IABkFQ> | <HEX>: Fluorophore |
| | SEGP1838 | 81 | <FAM>AGACTACGC<ZEN>TGAAGCT GGTGAC<3IABkFQ> | <FAM>: Fluorophore <ZEN>: Quencher <3IABkFQ>: 3' Blocker |

E. Sar/Cal Multiplex PCR ID-AST assay was performed in a polymicrobial sample where a 1:1 ratio of one Gram-positive organism, *Staphylococcus aureus* (Sar) and one fungal organism *Candida albicans* (Cal), with different susceptibility combinations were co-incubated together in the absence or presence of cefoxitin at varying concentrations. Detection of the Sar signal was from a FAM-labeled probe and detection of the Cal signal was from a HEX-labeled probe. Primers and probes used in this assay are shown in TABLE XXXVIII and the results are shown on FIG. 53. N/A indicates that there is no clinically relevant interpretation for the corresponding organism-drug combination. Cal susceptibility for fluconazole is indicated. The Sar strains displayed the appropriate phenotype in the corresponding detection channel as indicated by a delta-Ct threshold that separates susceptible and resistant isolates, providing accurate antimicrobial susceptibility results.

Example 23 PCR Assays for Determining Mechanism of Carbapenem Resistance

PCR assays that target the blaKPC, blaVIM, blaNDM, and blaOXA-48 genes were tested against Gram-negative pathogens with known mechanisms of carbapenem resistance: *K. pneumoniae, E. cloacae, P. aeruginosa, A. baumannii, E. coli* and *K. aerogenes*. The primers and probes used in this assay are listed in TABLE XXXIX. The concentration of the genomic DNA was roughly 2-10 ng/L for all samples other than the no template control. The results of the experiment are shown on FIG. 54. Growth curves, depicted as Positive (Pos) in the figure were observed only for the targeted resistance mechanism. No meaningful amplification was observed for non-target resistance mechanisms, thereby demonstrating good inclusivity and exclusivity profiles for this particular combination of primers and probes for detecting common mechanisms of carbapenem resistance.

TABLE XXXVIII

Oligonucleotides Used in Sar and Cal ID-AST Assay
Primers and Probes used in polymicrobial ID-AST assay with Staphylococcus aureus and Candida albicans

| Oligonucleotide Type | Oligonucleotide Name | SEQ ID NO: | Sequence | Modifications |
|---|---|---|---|---|
| Forward primers | SEGP1835 | 79 | CCGTGTTGAACGTGGTCAAATC AAA | |
| | SEGP1712 | 88 | CGTTTTCATTAATCAAGAACGAA AGTTA | |
| Reverse primers | SEGP1836 | 80 | AGCAGCTAATACTTGACCACGTT GTA | |
| | SEGP1713 | 89 | ACCGATCCCTAGTCGGCATA | |
| Probes | SEGP1838 | 81 | <FAM>AGACTACGC<ZEN>TGAA GCTGGTGAC<3IABkFQ> | <HEX>: Fluorophore <FAM>: Fluorophore |
| | SEGP1717 | 134 | <HEX>AGACTACGA<ZEN>CGGT ATCTGATCATCTTCGATCCC<3IA BkFQ> | <ZEN>: Quencher <3IABkFQ>: 3' Blocker |

TABLE XXXIX

Oligonucleotides Used in Carbapenem Resistance PCR Assay

| Gene Target | Oligonucleotide Type | Oligonucleotide Name | SEQ ID NO: | Sequence | Modifications |
|---|---|---|---|---|---|
| blaKPC | Forward Primer | SEGP2124 | 103 | GCGATACCACGTTCCGTCTG | |
| blaVIM | | SEGP2135 | 104 | CCGAGTGGTGAGTATCCGAC | |
| blaNDM | | SEGP2127 | 105 | TTTGGCGATCTGGTTTTCCG | |
| blaOXA-48 | | SEGP2133 | 106 | GGCACGTATGAGCAAGATGC | |
| blaKPC | Reverse Primer | SEGP2125 | 107 | CGGTCGTGTTTCCCTTTAGC | |
| blaVIM | | SEGP2136 | 108 | GAATGCGTGGGAATCTCGTTC | |
| blaNDM | | SEGP2128 | 109 | ATCAAACCGTTGGAAGCGAC | |
| blaOXA-48 | | SEGP2134 | 110 | GTTTGACAATACGCTGGCTGC | |
| blaKPC | Probe | SEGP2126 | 111 | <CFR_635>AGCGGCAGCAGTTT<BHQ_2>GTTGATTG<Phos> | <CFR_635>: Fluorophore <BHQ_2>: Quencher <phos>: 3, Blocker |
| blaVIM | | SEGP2137 | 112 | <CFR_635>CGCTGTATCAATCAA<BHQ_2>AAGCAACTCATCA<Phos> | |
| blaNDM | | SEGP2129 | 113 | <CFR_635>AGACATTCGGTGCGA<BHQ_2>GCTGGC<Phos> | |
| blaOXA-48 | | SEGP2346 | 114 | <CFR_635>TCGGGCAATGT<BHQ_2>AGACAGTTTCTGGCTCGACG<Phos> | |

Example 24 Species-Specific PCR ID-AST Assays

PCR assays using forward primer SEGP2164 (SEQ ID NO: 115), reverse primer SEGP2166 (SEQ ID NO: 116) and probe SEGP2167 (SEQ ID NO: 117) that target the citC gene of P. stuartii, and also forward primer SEGP2119 (SEQ ID NO: 118), reverse primer SEGP2121 (SEQ ID NO: 119) and probe SEGP2120 (SEQ ID NO: 120) that target the invA gene of Salmonella were tested against common Gram-negative pathogens: E. coli, K. pneumoniae, E. cloacae, K. oxytoca, K. aerogenes, S. marcescens, P. mirabilis, C. freundii, P. stuartii, P. rettgeri, S. enterica, S. maltophilia, P. aeruginosa, A. baumannii, and A. pittii. The sequences are shown in TABLE XL. Gram-positive organisms were also tested and showed no meaningful amplification (data not shown). The concentration of the genomic DNA was roughly 2-10 ng/uL for all samples, besides the no template control which was 0 ng/uL. As shown in FIG. 55, meaningful amplification curves were species-specific. No meaningful amplification was observed for non-target organisms, thereby demonstrating good inclusivity and exclusivity profiles for the four combinations of primers and probes for detecting the respective Gram-negative target species. These results represent non-limiting examples of species specific detection sets that allow improved breakpoint based AST calling for some specific species within the order Enterobacterales. CLSI guidelines indicate that some Enterobacterales species such as those shown here are resistant to specific aminoglycoside drugs, while the majority of Enterobacterales species are not.

TABLE XL

Oligonucleotides for detecting P. stuartii and Salmonella
Primers and Probes targeting citC gene of P. Stuartii and invA gene of Salmonella

| Oligonucleotide Type | Oligonucleotide Name | SEQ ID NO: | Sequence | Modifications |
|---|---|---|---|---|
| Forward primer | SEGP2164 | 115 | GCCATCGTGATGAATGCCAATCC | |
| | SEGP2119 | 118 | TGACCATTTCAATGGGAACTCTGC | |
| Reverse primer | SEGP2166 | 116 | TCAGAGCCTTTGTGGATAGTGAGA | |
| | SEGP2121 | 119 | AGATCGCCAATCAGTCCTAACGA | |
| Probe | SEGP2167 | 117 | <FAM>TTGGCTACA<ZEN>TTTATTTGTCGTCAAAGAAGATACCTCACGCTTCC<3IABkFQ> | <FAM>: Fluorophore <ZEN>: Quencher <3IABkFQ>: 3' Blocker |
| | SEGP2120 | 120 | <FAM>CAAAGGCGA<ZEN>GCAGCCGCTCAGTATTGAGGA<3IABkFQ> | |

PCR assays using forward primer SEGP2921 (SEQ ID NO: 121), reverse primer SEGP2922 (SEQ ID NO: 122) and probe SEGP2923 (SEQ ID NO: 123) that target the gyrB gene of *S. agalactiae*, forward primer SEGP2947 (SEQ ID NO: 85), reverse primer SEGP2949 (SEQ ID NO: 86) and probe SEGP2951 (SEQ ID NO: 87) that target the ddlA gene of *S. agalactiae*, forward primer SEGP2777 (SEQ ID NO: 124), reverse primer SEGP2778 (SEQ ID NO: 125) and probe SEGP2779 (SEQ ID NO: 126) that target the tuf gene of *S. pneumoniae* and forward primer SEGP2113 (SEQ ID NO: 127), reverse primer SEGP2114 (SEQ ID NO: 128) and probe SEGP2115 (SEQ ID NO: 129) that target the speB gene of *S. pyogenes* were tested against common Gram-positive pathogens: *S. agalactiae*, *S. pneumoniae*, *S. pyogenes*, *E. faecium*, *E. faecalis*, *S. aureus*, and *S. epidermidis*. The sequences are shown in TABLE XLI. Gram-negative organisms were also tested and showed no meaningful amplification (data not shown). The concentration of the genomic DNA was roughly 2-10 ng/uL for all samples, besides the no template control which was 0 ng/uL. As shown in FIG. 56, meaningful amplification curves were species-specific. No meaningful amplification was observed for non-target organisms, thereby demonstrating good inclusivity and exclusivity profiles for the four combinations of primers and probes for detecting the respective Gram-positive target species. These results represent non-limiting examples of species-specific detection sets that allow improved breakpoint based AST calling for some specific species within the *Staphylococcus* and *Streptococcus* genera (see CLSI breakpoint tables in FIG. 31), by having these ID-wells amore general ID/AST detection set such as those shown in FIG. 41 can be utilized.

Example 25 Interpretation of PCR ID-AST Assay Data

FIG. 58 depicts a workflow of a PCR ID-AST assay data interpretation strategy wherein a sigmoidal function is fit to the raw PCR curve data followed by calculation of curve parameters and features. Features are then compared between the presence of various antibiotic concentrations and the no-antibiotic reference to derive relative feature changes. Regression modeling of feature values and changes across antibiotic levels are also used to generate additional features that correspond to the feature dose-response relationship, and may include the use of Ordinary Least Squares, Ridge Regression, Lasso, Elastic Net, Bayesian Regression, or Logistic Regression models. Features are then assembled into a data frame and are input into separate machine learning algorithms along with the ground truth MIC, or ground truth S/I/R, in order to train predictive models, which may include Neural Networks, Tree-Based Models, Support Vector Machine, or Nearest-Neighbor classifiers. Training consists of splitting the data into a training set and a hold-out test set, followed by splitting the training set into k-folds with crossvalidation to search the appropriate hyperparameter space for each type of classifier. Models are then selected based on average crossvalidation scores as well as performance on the held-out test set. Trained models then participate as an ensemble to return the final predicted MIC, which can be based on unweighted voting, weighted voting, average probabilities, weighted probabilities, or interpreted by a downstream classifier of the aforementioned classifier types.

TABLE XLI

Oligonucleotides for detecting S. agalactiae, S. pneumoniae and S. pyogenes
Primers and Probes targeting gyrB gene of S. agalactiae, ddlA gene of S. agalactiae, tuf gene of S. pneumonia, speB gene of S. pyogenes

| Oligonucleotide Type | Oligonucleotide Name | SEQ ID NO: | Sequence | Modifications |
|---|---|---|---|---|
| Forward primer | SEGP2921 | 121 | ACCACTGTATTTGATTTTGATAAATTAGCCAAA | |
| | SEGP2947 | 85 | CACAAGAATTTGATGAAATGCCATCTTCA | |
| | SEGP2777 | 124 | GTGACTCTAAATACGAAGACATCGTT | |
| | SEGP2113 | 127 | CGGAAGAAGCCGTCAGAGAC | |
| Reverse primer | SEGP2922 | 122 | TTCTCATTGATAAACTCAACGTATGAACCTA | |
| | SEGP2949 | 86 | ACAATTGCATTATCATCATAGATATCACTTGGA | |
| | SEGP2778 | 125 | GCAATGGTTTGTCAGTGTCACG | |
| | SEGP2114 | 128 | ATGGTGCTGACGGACGTAAC | |
| Probe | SEGP2923 | 123 | <FAM>ACTAAGAAT<ZEN>CTCCATTTCAGACAAGCGAGAAGGTCAAGAAGTTG<3IABkFQ> | <FAM>: Fluorophore |
| | SEGP2951 | 87 | <FAM>TAATGACAA<ZEN>ACCAAACTGTTGATTTAGACAAAATGGTTCGTCCA<3IABkFQ> | <ZEN>: Quencher |
| | SEGP2779 | 126 | <FAM>TGAACACAG<ZEN>TTGATGAGTATATCCCA<3IABkFQ> | <3IABkFQ>: 3' Blocker |
| | SEGP2115 | 129 | <FAM>CACCCCAAC<ZEN>CCCAGTTAACA<3IABkFQ> | |

The impact of using species-specific primer/probe sets in making accurate calls in PCR ID-AST assays can be seen in FIG. 57. In the left panel, use of non-species-specific primers and probes may result in the inability to discriminate between susceptible and resistant strains. In contrast, in the right panel, the use of species-specific primer/probe sets that provide identification enables separate interpretation for each individual species, leading to improved Categorical Agreement to the CLSI breakpoint guidelines.

FIG. 59 shows a diagram indicating how Species ID, Antimicrobial Susceptibility Testing, Resistance Mechanism detection, and Universal 16 s rRNA phenotypic information is combined to return a result, wherein Species ID is used to select the appropriate algorithm for MIC prediction which is then compared to the appropriate breakpoints from regulatory bodies to determine susceptibility information. Detection of a resistance mechanism associated with the antibiotic that was tested can then influence the susceptibility result that is returned depending on whether its presence is consistent with the predicted MIC. In the absence of a Species ID, the 16 s rRNA phenotypic information can be used to return a generic MIC with no susceptibility result, which can be used in conjunction with a Species ID that is determined in an alternative fashion, such as mass spectrometry.

There are specific examples of using algorithmic elements to improve breakpoint based AST calling. One example is the use of resistance mechanism detection to adjust phenotype result calling. Each resistance mechanism can have one or more antibiotic substrates associated with its activity which are known a priori. These mechanisms can also have different time-frames in which their activity can be detected. Some of these resistance mechanisms do not have robust activity within 4 hours and can only be detected phenotypically after much longer incubation times (12-24 hours). For these resistance mechanisms an organism may be identified as susceptible to a given drug simply because the resistance mechanism has not manifested sufficiently within a 4 hour time frame. Detection of these types of resistance mechanisms via separate PCR wells allows for the correction of discordant phenotypic results. A specific example is *Serratia marcescens* that sometimes encodes a SME carbapenemase resistance mechanism which is inducible, but not within a 4 hour time frame. Thus these resistant *S. marcescens* strains will appear to be phenotypically susceptible to meropenem, but detection of the SME gene will allow the correct phenotypic prediction which is meropenem resistance. Another example is the use of phenotypic susceptibility from one or more antibiotics to predict susceptibility for other antibiotics. Because resistance mechanisms often have overlapping substrate specificity this means that susceptibility to some antibiotics is directly correlated with susceptibility to other antibiotics. Likewise, resistance to some antibiotics is directly correlated with resistance to other antibiotics. This is similar to the Expert Rules system that many AST product manufacturers employ whereas data collected from the PCR ID-AST assays of the present invention would be employed as an adjunct to other methods of phenotypic result interpretation. A specific example would be a strain that is susceptible to the antibiotic ertapenem will always be susceptible to the antibiotic meropenem due to the nature of carbapenemase and their substrate specificity which is always higher for degradation of ertapenem. Similarly, any strain that is resistant to meropenem will also be resistant to ertapenem for the same reason.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The invention claimed is:

1. A method to simultaneously identify and determine the antimicrobial susceptibility for one or more antimicrobial(s) of two or more different microorganisms in a polymicrobial biological sample comprising:

a) obtaining the polymicrobial biological sample in which the two or more different microorganisms are believed to be present;

b) optionally culturing the polymicrobial biological sample under conditions that facilitate growth of the two or more different microorganisms and optionally normalizing the cultured polymicrobial biological sample such that the two or more different microorganisms reach a desired concentration;

c) adding the polymicrobial biological sample in two or more reaction wells, whereby the one or more antimicrobial(s) is absent in at least one reaction well, and whereby the one or more antimicrobial(s) is present in one or more reaction wells at one concentration or at more than one varying concentrations, wherein in at least one reaction well, the concentration of the one or more antimicrobial(s) is either the Minimum Inhibitory Concentration (MIC) or the concentration used to classify the two or more different microorganisms as Sensitive, Intermediate or Resistant to the one or more antimicrobial(s);

d) incubating the polymicrobial biological sample in the presence or absence of the one or more antimicrobial(s) for a period of time required to detect inhibition of growth;

e) performing a quantitative 5' nuclease (TaqMan) real-time PCR assay in each of the two or more reaction wells, whereby, each PCR assay comprises:
  (i) an amplifying step with at least a first set of primers and a second set of primers, wherein the first set of primers selectively anneals to a first target gene in a first microorganism and produces a first amplification product if the first microorganism is present in the polymicrobial biological sample, wherein the first microorganism is bacteria in the taxonomic Order Enterobacterales and the first target gene is gyrB, and wherein the second set of primers selectively anneals to a second target gene in a second microorganism and produces a second amplification product if the second microorganism is present in the polymicrobial biological sample, wherein the second microorganism is *Acinetobacter baumannii* and the second target gene is ompA, and
  (ii) a hybridizing step wherein a first TaqMan probe labeled with a first fluorescent dye selectively anneals to the first amplification product and generates a first fluorescent signal and a second TaqMan probe labeled with a second fluorescent dye selectively anneals to the second amplification product and generates a second fluorescent signal;

f) identifying the two or more different microorganisms whereby detection of the first fluorescent signal is indicative of the presence of the first microorganism and detection of the second fluorescent signal is indicative of the presence of the second microorganism; and g) determining the antimicrobial susceptibility of the two or more different microorganisms by comparing the first and second fluorescent signals detected in the at least one reaction well where the one or more antimicrobial(s) is absent to the first and second fluorescent signals detected in the one or more reaction well(s) where the one or more antimicrobial(s) is present;

wherein steps e), f), and g), are all performed simultaneously in each of the two or more reaction wells.

2. The method of claim 1 wherein the bacteria in the taxonomic Order Enterobacterales is selected from *Escherichia coli, Klebsiella pneumoniae, Enterobacter cloacae, Klebsiella oxytoca, Klebsiella aerogenes, Serratia marcescens*, or *Proteus mirabilis*.

3. The method of claim 2 wherein the bacteria is *Klebsiella pneumoniae*.

4. The method of claim 1 wherein the first set of primers that selectively anneals to gyrB comprise a forward primer having a nucleotide sequence of SEQ ID NO: 8 and a reverse primer having a nucleotide sequence of SEQ ID NO: 9 and the first TaqMan probe that selectively anneals to the first amplification product of gyrB has a nucleotide sequence of SEQ ID NO: 10.

5. The method of claim 1 wherein the second set of primers that selectively anneals to ompA comprise a forward primer having a nucleotide sequence of SEQ ID NO: 29 and a reverse primer having a nucleotide sequence of SEQ ID NO: 30 and the second TaqMan probe that selectively anneals to the second amplification product of ompA has a nucleotide sequence of SEQ ID NO: 31.

* * * * *

```
                         SEQUENCE LISTING

<160> NUMBER OF SEQ ID NOS: 134

<210> SEQ ID NO 1
<211> LENGTH: 19
<212> TYPE: DNA
<213> ORGANISM: Artificial Sequence
<220> FEATURE:
<223> OTHER INFORMATION: Enterobacteriales rplP Forward Primer RM_ENTF
<220> FEATURE:
<221> NAME/KEY: modified_base
<222> LOCATION: (19)..(19)
<223> OTHER INFORMATION: t-butylbenzyl-dC

<400> SEQUENCE: 1
taatcggcag tttcgctgc                                                      19

<210> SEQ ID NO 2
<211> LENGTH: 20
<212> TYPE: DNA
<213> ORGANISM: Artificial Sequence
<220> FEATURE:
<223> OTHER INFORMATION: Enterobacteriales rplP Reverse Primer RM_ENTRP
<220> FEATURE:
<221> NAME/KEY: modified_base
<222> LOCATION: (20)..(20)
<223> OTHER INFORMATION: t-butylbenzyl-dA

<400> SEQUENCE: 2
gttcccggac aaaccgatca                                                     20

<210> SEQ ID NO 3
<211> LENGTH: 33
<212> TYPE: DNA
<213> ORGANISM: Artificial Sequence
<220> FEATURE:
<223> OTHER INFORMATION: Enterobacteriales rplP Probe 1 RM_ETP02
```

```
<220> FEATURE:
<221> NAME/KEY: misc_feature
<223> OTHER INFORMATION: 5'-Cy5.5
<220> FEATURE:
<221> NAME/KEY: misc_feature
<223> OTHER INFORMATION: 3'-Phosphate
<220> FEATURE:
<221> NAME/KEY: misc_feature
<222> LOCATION: (11)..(12)
<223> OTHER INFORMATION: BHQ-2 Quencher

<400> SEQUENCE: 3
ttcacgggcc agctcttccg gaacaccgtc cat                                   33

<210> SEQ ID NO 4
<211> LENGTH: 33
<212> TYPE: DNA
<213> ORGANISM: Artificial Sequence
<220> FEATURE:
<223> OTHER INFORMATION: Enterobacteriales rplP Probe 2 RM_ETP02B
<220> FEATURE:
<221> NAME/KEY: misc_feature
<223> OTHER INFORMATION: 5'-Cy5.5
<220> FEATURE:
<221> NAME/KEY: misc_feature
<223> OTHER INFORMATION: 3'-Phosphate
<220> FEATURE:
<221> NAME/KEY: misc_feature
<222> LOCATION: (11)..(12)
<223> OTHER INFORMATION: BHQ-2 Quencher

<400> SEQUENCE: 4
ctggatcagg gcaacccaat actccacgtt acc                                   33

<210> SEQ ID NO 5
<211> LENGTH: 24
<212> TYPE: DNA
<213> ORGANISM: Artificial Sequence
<220> FEATURE:
<223> OTHER INFORMATION: Enterobacteriales rplP Forward Primer SEGP2891

<400> SEQUENCE: 5
aattccgtaa aatgcacaaa ggcc                                             24

<210> SEQ ID NO 6
<211> LENGTH: 23
<212> TYPE: DNA
<213> ORGANISM: Artificial Sequence
<220> FEATURE:
<223> OTHER INFORMATION: Enterobacteriales rplP Reverse Primer SEGP2892

<400> SEQUENCE: 6
gcttaactgc acgggtcata gca                                              23

<210> SEQ ID NO 7
<211> LENGTH: 30
<212> TYPE: DNA
<213> ORGANISM: Artificial Sequence
<220> FEATURE:
<223> OTHER INFORMATION: Enterobacteriales rplP Probe SEGP2893
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher
```

-continued

<400> SEQUENCE: 7
tggtcgtctg actgcacgtc agatcgaagc                                              30

<210> SEQ ID NO 8
<211> LENGTH: 27
<212> TYPE: DNA
<213> ORGANISM: Artificial Sequence
<220> FEATURE:
<223> OTHER INFORMATION: Enterobacteriales gyrB Forward Primer SEGP1899

<400> SEQUENCE: 8
tgtcgaattc ttatgactcc tccagta                                                 27

<210> SEQ ID NO 9
<211> LENGTH: 17
<212> TYPE: DNA
<213> ORGANISM: Artificial Sequence
<220> FEATURE:
<223> OTHER INFORMATION: Enterobacteriales gyrB Reverse Primer SEGP1901

<400> SEQUENCE: 9
cgcgagcgct tcgtcga                                                            17

<210> SEQ ID NO 10
<211> LENGTH: 30
<212> TYPE: DNA
<213> ORGANISM: Artificial Sequence
<220> FEATURE:
<223> OTHER INFORMATION: Enterobacteriales gyrB Probe SEGP2016
<220> FEATURE:
<221> NAME/KEY: misc_feature
<223> OTHER INFORMATION: 5'-HEX
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 10
ccggtctgca ccacatggta ttcgaggtgg                                              30

<210> SEQ ID NO 11
<211> LENGTH: 24
<212> TYPE: DNA
<213> ORGANISM: Artificial Sequence
<220> FEATURE:
<223> OTHER INFORMATION: Enterobacteriales rpoB Forward Primer SEGP2799

<400> SEQUENCE: 11
tggtaaacgt ccacaagttc tgga                                                    24

<210> SEQ ID NO 12
<211> LENGTH: 23
<212> TYPE: DNA
<213> ORGANISM: Artificial Sequence
<220> FEATURE:
<223> OTHER INFORMATION: Enterobacteriales rpoB Reverse Primer 1
      SEGP2800

<400> SEQUENCE: 12
catactgccc ttcaggatct tgc                                                     23

<210> SEQ ID NO 13
<211> LENGTH: 25
<212> TYPE: DNA

```
<213> ORGANISM: Artificial Sequence
<220> FEATURE:
<223> OTHER INFORMATION: Enterobacteriales rpoB Reverse Primer 2
      SEGP2802

<400> SEQUENCE: 13
gtagctgaca tattgcagtt cagca                                           25

<210> SEQ ID NO 14
<211> LENGTH: 20
<212> TYPE: DNA
<213> ORGANISM: Artificial Sequence
<220> FEATURE:
<223> OTHER INFORMATION: Enterobacteriales rpoB Reverse Primer 3
      SEGP2821

<400> SEQUENCE: 14
ccgttctgac cgtccggatc                                                 20

<210> SEQ ID NO 15
<211> LENGTH: 44
<212> TYPE: DNA
<213> ORGANISM: Artificial Sequence
<220> FEATURE:
<223> OTHER INFORMATION: Enterobacteriales rpoB Probe 1 SEGP2804
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 15
tatctccttt ctatccagct tgactcgttt cagaagttta tcga                      44

<210> SEQ ID NO 16
<211> LENGTH: 44
<212> TYPE: DNA
<213> ORGANISM: Artificial Sequence
<220> FEATURE:
<223> OTHER INFORMATION: Enterobacteriales rpoB Probe 2 SEGP2822
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 16
tctcctttct atccagctgg attcattcca gaaattcatt gaac                      44

<210> SEQ ID NO 17
<211> LENGTH: 18
<212> TYPE: DNA
<213> ORGANISM: Artificial Sequence
<220> FEATURE:
<223> OTHER INFORMATION: A. Baumannii ompA Forward Primer RM_AFP01

<400> SEQUENCE: 17
ttggtggtca cttgaagc                                                   18
```

<210> SEQ ID NO 18
<211> LENGTH: 19
<212> TYPE: DNA
<213> ORGANISM: Artificial Sequence
<220> FEATURE:
<223> OTHER INFORMATION: A. Baumannii ompA Reverse Primer RM_ARP02

<400> SEQUENCE: 18
tttctggctt gtattggtc                                                19

<210> SEQ ID NO 19
<211> LENGTH: 27
<212> TYPE: DNA
<213> ORGANISM: Artificial Sequence
<220> FEATURE:
<223> OTHER INFORMATION: A. Baumannii ompA Probe RM_P02
<220> FEATURE:
<221> NAME/KEY: misc_feature
<223> OTHER INFORMATION: 5'-HEX
<220> FEATURE:
<221> NAME/KEY: misc_feature
<223> OTHER INFORMATION: 3'-Phosphate
<220> FEATURE:
<221> NAME/KEY: misc_feature
<222> LOCATION: (7)..(8)
<223> OTHER INFORMATION: BHQ-2 Quencher

<400> SEQUENCE: 19
actccagttg ctccacaacc acaagag                                       27

<210> SEQ ID NO 20
<211> LENGTH: 30
<212> TYPE: DNA
<213> ORGANISM: Artificial Sequence
<220> FEATURE:
<223> OTHER INFORMATION: A. Baumannii ompA Forward Primer SEGP2603

<400> SEQUENCE: 20
ttatctttag ctcgtgctaa ctctgttaaa                                    30

<210> SEQ ID NO 21
<211> LENGTH: 27
<212> TYPE: DNA
<213> ORGANISM: Artificial Sequence
<220> FEATURE:
<223> OTHER INFORMATION: A. Baumannii ompA Reverse Primer SEGP2606

<400> SEQUENCE: 21
gcacgacctt ctttagtttt gttgtca                                       27

<210> SEQ ID NO 22
<211> LENGTH: 36
<212> TYPE: DNA
<213> ORGANISM: Artificial Sequence
<220> FEATURE:
<223> OTHER INFORMATION: A. Baumannii ompA Probe SEGP2769
<220> FEATURE:
<221> NAME/KEY: misc_feature
<223> OTHER INFORMATION: 5'-ATTO
<220> FEATURE:
<221> NAME/KEY: misc_feature
<223> OTHER INFORMATION: 3'-Phosphate
<220> FEATURE:
<221> NAME/KEY: misc_feature
<222> LOCATION: (8)..(9)
<223> OTHER INFORMATION: BHQ-2 Quencher

<400> SEQUENCE: 22
tctactcaag gtttcgcttg ggatcaaccg attgct                             36

```
<210> SEQ ID NO 23
<211> LENGTH: 26
<212> TYPE: DNA
<213> ORGANISM: Artificial Sequence
<220> FEATURE:
<223> OTHER INFORMATION: A. Baumannii rpoB Forward Primer SEGP2590

<400> SEQUENCE: 23
catactcata taccgaaaag aaacgg                                          26

<210> SEQ ID NO 24
<211> LENGTH: 26
<212> TYPE: DNA
<213> ORGANISM: Artificial Sequence
<220> FEATURE:
<223> OTHER INFORMATION: A. Baumannii rpoB Reverse Primer SEGP2593

<400> SEQUENCE: 24
ctatactcaa caaattctaa agcagc                                          26

<210> SEQ ID NO 25
<211> LENGTH: 19
<212> TYPE: DNA
<213> ORGANISM: Artificial Sequence
<220> FEATURE:
<223> OTHER INFORMATION: A. Baumannii rpoB Probe SEGP2594
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 25
cgcgaagata tcggtctcc                                                  19

<210> SEQ ID NO 26
<211> LENGTH: 32
<212> TYPE: DNA
<213> ORGANISM: Artificial Sequence
<220> FEATURE:
<223> OTHER INFORMATION: A. Baumannii gyrB Forward Primer SEGP2626

<400> SEQUENCE: 26
acagaacaaa ccaatgaaaa ggcttatgat tc                                   32

<210> SEQ ID NO 27
<211> LENGTH: 23
<212> TYPE: DNA
<213> ORGANISM: Artificial Sequence
<220> FEATURE:
<223> OTHER INFORMATION: A. Baumannii gyrB Reverse Primer SEGP2628

<400> SEQUENCE: 27
accatatggt gtaaaccggt acc                                             23

<210> SEQ ID NO 28
<211> LENGTH: 42
<212> TYPE: DNA
<213> ORGANISM: Artificial Sequence
<220> FEATURE:
<223> OTHER INFORMATION: A. Baumannii gyrB Probe SEGP2629
<220> FEATURE:
<221> NAME/KEY: misc_feature
```

```
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 28
aaagtattac gtggattaga tgcagttcgt aaacgtccgg gt                           42

<210> SEQ ID NO 29
<211> LENGTH: 20
<212> TYPE: DNA
<213> ORGANISM: Artificial Sequence
<220> FEATURE:
<223> OTHER INFORMATION: A Baumannii Gene X Forward Primer SEGP1813

<400> SEQUENCE: 29
accctaacgc tactgcacgt                                                   20

<210> SEQ ID NO 30
<211> LENGTH: 21
<212> TYPE: DNA
<213> ORGANISM: Artificial Sequence
<220> FEATURE:
<223> OTHER INFORMATION: A. Baumannii Gene X Reverse Primer SEGP1815

<400> SEQUENCE: 30
ggttgatccc aagcgaaacc t                                                 21

<210> SEQ ID NO 31
<211> LENGTH: 23
<212> TYPE: DNA
<213> ORGANISM: Artificial Sequence
<220> FEATURE:
<223> OTHER INFORMATION: A. Baumannii Gene X Probe SEGP1951
<220> FEATURE:
<221> NAME/KEY: misc_feature
<223> OTHER INFORMATION: 5'-ATTO
<220> FEATURE:
<221> NAME/KEY: misc_feature
<223> OTHER INFORMATION: 3'-Phosphate
<220> FEATURE:
<221> NAME/KEY: misc_feature
<222> LOCATION: (8)..(9)
<223> OTHER INFORMATION: BHQ-2 Quencher

<400> SEQUENCE: 31
tcgaaggtca cacagataac act                                               23

<210> SEQ ID NO 32
<211> LENGTH: 18
<212> TYPE: DNA
<213> ORGANISM: Artificial Sequence
<220> FEATURE:
<223> OTHER INFORMATION: P. Aeruginosa tuf Forward Primer SEGP2341

<400> SEQUENCE: 32
ccgtgcagaa gctggtag                                                     18

<210> SEQ ID NO 33
<211> LENGTH: 21
<212> TYPE: DNA
<213> ORGANISM: Artificial Sequence
<220> FEATURE:
<223> OTHER INFORMATION: P. Aeruginosa tuf Reverse Primer SEGP2342
```

```
<400> SEQUENCE: 33
gagatcgaga acacgtcttc g                                              21

<210> SEQ ID NO 34
<211> LENGTH: 24
<212> TYPE: DNA
<213> ORGANISM: Artificial Sequence
<220> FEATURE:
<223> OTHER INFORMATION: P. Aeruginosa tuf Probe SEGP2343
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 34
ttccggagcc ggttcgtgcc atcg                                           24

<210> SEQ ID NO 35
<211> LENGTH: 23
<212> TYPE: DNA
<213> ORGANISM: Artificial Sequence
<220> FEATURE:
<223> OTHER INFORMATION: P. Aeruginosa gyrB Forward Primer SEGP2630

<400> SEQUENCE: 35
ggagtacaac atcgacaagc tgc                                            23

<210> SEQ ID NO 36
<211> LENGTH: 18
<212> TYPE: DNA
<213> ORGANISM: Artificial Sequence
<220> FEATURE:
<223> OTHER INFORMATION: P. Aeruginosa gyrB Reverse Primer SEGP2631

<400> SEQUENCE: 36
cgctcgatca gctcgggc                                                  18

<210> SEQ ID NO 37
<211> LENGTH: 36
<212> TYPE: DNA
<213> ORGANISM: Artificial Sequence
<220> FEATURE:
<223> OTHER INFORMATION: P. Aeruginosa gyrB Probe SEGP2632
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 37
cacaacatca tcatcatgac cgatgctgac gtcgac                              36

<210> SEQ ID NO 38
<211> LENGTH: 20
<212> TYPE: DNA
<213> ORGANISM: Artificial Sequence
<220> FEATURE:
<223> OTHER INFORMATION: P. Aeruginosa rpoB Forward Primer SEGP2634
```

<400> SEQUENCE: 38
ggcgtgctga agatcgtcaa                                        20

<210> SEQ ID NO 39
<211> LENGTH: 19
<212> TYPE: DNA
<213> ORGANISM: Artificial Sequence
<220> FEATURE:
<223> OTHER INFORMATION: P. Aeruginosa rpoB Reverse Primer SEGP2637

<400> SEQUENCE: 39
accggcatga tcaccgaga                                         19

<210> SEQ ID NO 40
<211> LENGTH: 25
<212> TYPE: DNA
<213> ORGANISM: Artificial Sequence
<220> FEATURE:
<223> OTHER INFORMATION: P. Aeruginosa rpoB Probe SEGP2640
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 40
cgcatccagc cgggcgacaa gatgg                                  25

<210> SEQ ID NO 41
<211> LENGTH: 20
<212> TYPE: DNA
<213> ORGANISM: Artificial Sequence
<220> FEATURE:
<223> OTHER INFORMATION: S. Maltophilia fdnG Forward Primer SEGP2532

<400> SEQUENCE: 41
ccaagctcga caagccgtac                                        20

<210> SEQ ID NO 42
<211> LENGTH: 20
<212> TYPE: DNA
<213> ORGANISM: Artificial Sequence
<220> FEATURE:
<223> OTHER INFORMATION: S. Maltophilia fdnG Reverse Primer SEGP2538

<400> SEQUENCE: 42
gcttggagaa cgcgctgatc                                        20

<210> SEQ ID NO 43
<211> LENGTH: 29
<212> TYPE: DNA
<213> ORGANISM: Artificial Sequence
<220> FEATURE:
<223> OTHER INFORMATION: S. Maltophilia fdnG Probe SEGP2544
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)

<223> OTHER INFORMATION: ZEN Quencher

<400> SEQUENCE: 43
tgcaggcgta cgagctgatg aacgaaggc                                29

<210> SEQ ID NO 44
<211> LENGTH: 19
<212> TYPE: DNA
<213> ORGANISM: Artificial Sequence
<220> FEATURE:
<223> OTHER INFORMATION: S. Maltophilia gyrB Forward Primer SEGP2578

<400> SEQUENCE: 44
tgcagtggac cgactccta                                           19

<210> SEQ ID NO 45
<211> LENGTH: 20
<212> TYPE: DNA
<213> ORGANISM: Artificial Sequence
<220> FEATURE:
<223> OTHER INFORMATION: S. Maltophilia gyrB Reverse Primer SEGP2579

<400> SEQUENCE: 45
ctgcttggcg atgccgttct                                          20

<210> SEQ ID NO 46
<211> LENGTH: 22
<212> TYPE: DNA
<213> ORGANISM: Artificial Sequence
<220> FEATURE:
<223> OTHER INFORMATION: S. Maltophilia gyrB Probe SEGP2580
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 46
gacgatgtac tgcttcacca ac                                       22

<210> SEQ ID NO 47
<211> LENGTH: 18
<212> TYPE: DNA
<213> ORGANISM: Artificial Sequence
<220> FEATURE:
<223> OTHER INFORMATION: S. Maltophilia tuf Forward Primer SEGP2572

<400> SEQUENCE: 47
gcaccaagcc gcacgtca                                            18

<210> SEQ ID NO 48
<211> LENGTH: 18
<212> TYPE: DNA
<213> ORGANISM: Artificial Sequence
<220> FEATURE:
<223> OTHER INFORMATION: S. Maltophilia tuf Reverse Primer SEGP2573

<400> SEQUENCE: 48
gtgcgcggtc gagatcgt                                            18

<210> SEQ ID NO 49
<211> LENGTH: 18

```
<212> TYPE: DNA
<213> ORGANISM: Artificial Sequence
<220> FEATURE:
<223> OTHER INFORMATION: S. Maltophilia tuf Probe SEGP2574
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 49
caagaccacg ctgaccgc                                                 18

<210> SEQ ID NO 50
<211> LENGTH: 22
<212> TYPE: DNA
<213> ORGANISM: Artificial Sequence
<220> FEATURE:
<223> OTHER INFORMATION: Enterococcus tuf Forward Primer SEGP1632

<400> SEQUENCE: 50
gacaaaccat tcatgatgcc ag                                            22

<210> SEQ ID NO 51
<211> LENGTH: 21
<212> TYPE: DNA
<213> ORGANISM: Artificial Sequence
<220> FEATURE:
<223> OTHER INFORMATION: Enterococcus tuf Reverse Primer SEGP1631

<400> SEQUENCE: 51
aacttcgtca ccaacgcgaa c                                             21

<210> SEQ ID NO 52
<211> LENGTH: 22
<212> TYPE: DNA
<213> ORGANISM: Artificial Sequence
<220> FEATURE:
<223> OTHER INFORMATION: Enterococcus tuf Probe SEGP1633
<220> FEATURE:
<221> NAME/KEY: misc_feature
<223> OTHER INFORMATION: 5'-HEX
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 52
ctggacgtgg tactgttgct ac                                            22

<210> SEQ ID NO 53
<211> LENGTH: 23
<212> TYPE: DNA
<213> ORGANISM: Artificial Sequence
<220> FEATURE:
<223> OTHER INFORMATION: Enterococcus rpoB Forward Primer SEGP2522

<400> SEQUENCE: 53
ccgtccagtg gtagcaagta tca                                           23

<210> SEQ ID NO 54
```

```
<211> LENGTH: 25
<212> TYPE: DNA
<213> ORGANISM: Artificial Sequence
<220> FEATURE:
<223> OTHER INFORMATION: Enterococcus rpoB Reverse Primer SEGP2525

<400> SEQUENCE: 54
accatagtga gagtagtgaa cgtca                                          25

<210> SEQ ID NO 55
<211> LENGTH: 32
<212> TYPE: DNA
<213> ORGANISM: Artificial Sequence
<220> FEATURE:
<223> OTHER INFORMATION: Enterococcus rpoB Probe SEGP2770
<220> FEATURE:
<221> NAME/KEY: misc_feature
<223> OTHER INFORMATION: 5'-HEX
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 55
ttgactcgtg accgtgccgg ttatgaagtt cg                                  32

<210> SEQ ID NO 56
<211> LENGTH: 25
<212> TYPE: DNA
<213> ORGANISM: Artificial Sequence
<220> FEATURE:
<223> OTHER INFORMATION: Enterococcus ddl Forward Primer 1 SEGP1624

<400> SEQUENCE: 56
cgtagcattc tatgattatg aagcc                                          25

<210> SEQ ID NO 57
<211> LENGTH: 23
<212> TYPE: DNA
<213> ORGANISM: Artificial Sequence
<220> FEATURE:
<223> OTHER INFORMATION: Enterococcus ddl Forward Primer 2 SEGP1627

<400> SEQUENCE: 57
gacaggaaag aaactaggag gac                                            23

<210> SEQ ID NO 58
<211> LENGTH: 20
<212> TYPE: DNA
<213> ORGANISM: Artificial Sequence
<220> FEATURE:
<223> OTHER INFORMATION: Enterococcus ddl Reverse Primer 1 SEGP1625

<400> SEQUENCE: 58
catcgtgtaa gctaacttcg                                                20

<210> SEQ ID NO 59
<211> LENGTH: 18
<212> TYPE: DNA
<213> ORGANISM: Artificial Sequence
<220> FEATURE:
<223> OTHER INFORMATION: Enterococcus ddl Reverse Primer 2 SEGP1628

<400> SEQUENCE: 59
aaacagacac atcgtgct                                                  18
```

```
<210> SEQ ID NO 60
<211> LENGTH: 20
<212> TYPE: DNA
<213> ORGANISM: Artificial Sequence
<220> FEATURE:
<223> OTHER INFORMATION: Enterococcus ddl Probe 1 SEGP1626
<220> FEATURE:
<221> NAME/KEY: misc_feature
<223> OTHER INFORMATION: 5'-HEX
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 60
cagattccag ccgaagtgcc                                              20

<210> SEQ ID NO 61
<211> LENGTH: 22
<212> TYPE: DNA
<213> ORGANISM: Artificial Sequence
<220> FEATURE:
<223> OTHER INFORMATION: Enterococcus ddl Probe 2 SEGP1629
<220> FEATURE:
<221> NAME/KEY: misc_feature
<223> OTHER INFORMATION: 5'-HEX
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 61
cacttctgcc gccatacaac aa                                           22

<210> SEQ ID NO 62
<211> LENGTH: 33
<212> TYPE: DNA
<213> ORGANISM: Artificial Sequence
<220> FEATURE:
<223> OTHER INFORMATION: Enterococcus gyrB Forward Primer 1 SEGP2882

<400> SEQUENCE: 62
agcaacgatc ctgaaaaatg cgaattgttc atc                               33

<210> SEQ ID NO 63
<211> LENGTH: 33
<212> TYPE: DNA
<213> ORGANISM: Artificial Sequence
<220> FEATURE:
<223> OTHER INFORMATION: Enterococcus gyrB Forward Primer 2 SEGP2884

<400> SEQUENCE: 63
agtaaagatc cggaaaaatg cgaattattt atc                               33

<210> SEQ ID NO 64
<211> LENGTH: 24
<212> TYPE: DNA
<213> ORGANISM: Artificial Sequence
<220> FEATURE:
<223> OTHER INFORMATION: Enterococcus gyrB Reverse Primer 1 SEGP2885

<400> SEQUENCE: 64
```
aaagaccgga tctcttcatt tgcc                                              24

<210> SEQ ID NO 65
<211> LENGTH: 24
<212> TYPE: DNA
<213> ORGANISM: Artificial Sequence
<220> FEATURE:
<223> OTHER INFORMATION: Enterococcus gyrB Reverse Primer 2 SEGP2886

<400> SEQUENCE: 65
aatgaccgaa tttcttcatt ggct                                              24

<210> SEQ ID NO 66
<211> LENGTH: 40
<212> TYPE: DNA
<213> ORGANISM: Artificial Sequence
<220> FEATURE:
<223> OTHER INFORMATION: Enterococcus gyrB Probe SEGP2888
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 66
ccaattcgtg ggaaaatctt gaatgttgag aaagcaagca                             40

<210> SEQ ID NO 67
<211> LENGTH: 27
<212> TYPE: DNA
<213> ORGANISM: Artificial Sequence
<220> FEATURE:
<223> OTHER INFORMATION: S. Aureus CPE Forwad Primer SEGP1490

<400> SEQUENCE: 67
aagataagct tattgaacaa ggacatc                                           27

<210> SEQ ID NO 68
<211> LENGTH: 23
<212> TYPE: DNA
<213> ORGANISM: Artificial Sequence
<220> FEATURE:
<223> OTHER INFORMATION: S. Aureus CPE Reverse Primer SEGP1491

<400> SEQUENCE: 68
cttgaggtga attgttgtga acc                                               23

<210> SEQ ID NO 69
<211> LENGTH: 30
<212> TYPE: DNA
<213> ORGANISM: Artificial Sequence
<220> FEATURE:
<223> OTHER INFORMATION: S. Aureus CPE Probe SEGP1493
<220> FEATURE:
<221> NAME/KEY: misc_feature
<223> OTHER INFORMATION: 5'-HEX
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 69
ttaggaatca attatggaag tcgacctcgt                                              30

<210> SEQ ID NO 70
<211> LENGTH: 27
<212> TYPE: DNA
<213> ORGANISM: Artificial Sequence
<220> FEATURE:
<223> OTHER INFORMATION: S. Aureus capN Forward Primer SEGP1490

<400> SEQUENCE: 70
aagataagct tattgaacaa ggacatc                                                 27

<210> SEQ ID NO 71
<211> LENGTH: 23
<212> TYPE: DNA
<213> ORGANISM: Artificial Sequence
<220> FEATURE:
<223> OTHER INFORMATION: S. Aureus capN Reverse Primer SEGP1491

<400> SEQUENCE: 71
cttgaggtga attgttgtga acc                                                     23

<210> SEQ ID NO 72
<211> LENGTH: 30
<212> TYPE: DNA
<213> ORGANISM: Artificial Sequence
<220> FEATURE:
<223> OTHER INFORMATION: S. Aureus capN Probe SEGP1492
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 72
ttaggaatca attatggaag tcgacctcgt                                              30

<210> SEQ ID NO 73
<211> LENGTH: 20
<212> TYPE: DNA
<213> ORGANISM: Artificial Sequence
<220> FEATURE:
<223> OTHER INFORMATION: S. Aureus gyrB Forward Primer SEGP2792

<400> SEQUENCE: 73
cacaagtcgc acgtacagtg                                                         20

<210> SEQ ID NO 74
<211> LENGTH: 29
<212> TYPE: DNA
<213> ORGANISM: Artificial Sequence
<220> FEATURE:
<223> OTHER INFORMATION: S. Aureus gyrB Reverse Primer SEGP2793

<400> SEQUENCE: 74
attcttcagg acttttacta gagcaatcg                                               29

<210> SEQ ID NO 75
<211> LENGTH: 26
<212> TYPE: DNA
<213> ORGANISM: Artificial Sequence
<220> FEATURE:

```
<223> OTHER INFORMATION: S. Aureus gyrB Probe SEGP2794
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 75
taaatcagcg ttagatgtag caagtc                                        26

<210> SEQ ID NO 76
<211> LENGTH: 31
<212> TYPE: DNA
<213> ORGANISM: Artificial Sequence
<220> FEATURE:
<223> OTHER INFORMATION: S. Aureus ddlA Forward Primer SEGP2932

<400> SEQUENCE: 76
atctactgat gagcttcatt tagaaaatgg a                                  31

<210> SEQ ID NO 77
<211> LENGTH: 24
<212> TYPE: DNA
<213> ORGANISM: Artificial Sequence
<220> FEATURE:
<223> OTHER INFORMATION: S. Aureus ddlA Reverse Primer SEGP2933

<400> SEQUENCE: 77
tcaaaaagtc cttgaatcgt gcca                                          24

<210> SEQ ID NO 78
<211> LENGTH: 44
<212> TYPE: DNA
<213> ORGANISM: Artificial Sequence
<220> FEATURE:
<223> OTHER INFORMATION: S. Aureus ddlA Probe SEGP2935
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 78
cgcttgagat ttcacagcta ttgaaagaaa gtagttcagg acaa                    44

<210> SEQ ID NO 79
<211> LENGTH: 25
<212> TYPE: DNA
<213> ORGANISM: Artificial Sequence
<220> FEATURE:
<223> OTHER INFORMATION: S. Aureus tuf Forward Primer SEGP1835

<400> SEQUENCE: 79
ccgtgttgaa cgtggtcaaa tcaaa                                         25

<210> SEQ ID NO 80
<211> LENGTH: 26
<212> TYPE: DNA
<213> ORGANISM: Artificial Sequence
```

```
<220> FEATURE:
<223> OTHER INFORMATION: S. Aureus tuf Reverse Primer SEGP1836

<400> SEQUENCE: 80
agcagctaat acttgaccac gttgta                                           26

<210> SEQ ID NO 81
<211> LENGTH: 22
<212> TYPE: DNA
<213> ORGANISM: Artificial Sequence
<220> FEATURE:
<223> OTHER INFORMATION: S. Aureus tuf Probe SEGP1838
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 81
agactacgct gaagctggtg ac                                               22

<210> SEQ ID NO 82
<211> LENGTH: 20
<212> TYPE: DNA
<213> ORGANISM: Artificial Sequence
<220> FEATURE:
<223> OTHER INFORMATION: S. Agalactiae sip Forward Primer SEGP2204

<400> SEQUENCE: 82
atcctgagac aacactgaca                                                  20

<210> SEQ ID NO 83
<211> LENGTH: 21
<212> TYPE: DNA
<213> ORGANISM: Artificial Sequence
<220> FEATURE:
<223> OTHER INFORMATION: S. Agalactiae sip Reverse Primer SEGP2205

<400> SEQUENCE: 83
ttgctggtgt ttctattttc a                                                21

<210> SEQ ID NO 84
<211> LENGTH: 25
<212> TYPE: DNA
<213> ORGANISM: Artificial Sequence
<220> FEATURE:
<223> OTHER INFORMATION: S. Agalactiae sip Probe SEGP2206
<220> FEATURE:
<221> NAME/KEY: misc_feature
<223> OTHER INFORMATION: 5'-Cy5.5
<220> FEATURE:
<221> NAME/KEY: misc_feature
<223> OTHER INFORMATION: 3'-Phosphate
<220> FEATURE:
<221> NAME/KEY: misc_feature
<222> LOCATION: (11)..(12)
<223> OTHER INFORMATION: BHQ-2 Quencher

<400> SEQUENCE: 84
atcagaagag tcatactgcc acttc                                            25

<210> SEQ ID NO 85
<211> LENGTH: 29
<212> TYPE: DNA
```

```
<213> ORGANISM: Artificial Sequence
<220> FEATURE:
<223> OTHER INFORMATION: S. Agalactiae ddlA Forward Primer SEGP2947

<400> SEQUENCE: 85
cacaagaatt tgatgaaatg ccatcttca                                     29

<210> SEQ ID NO 86
<211> LENGTH: 33
<212> TYPE: DNA
<213> ORGANISM: Artificial Sequence
<220> FEATURE:
<223> OTHER INFORMATION: S. Agalactiae ddlA Reverse Primer SEGP2949

<400> SEQUENCE: 86
acaattgcat tatcatcata gatatcactt gga                                33

<210> SEQ ID NO 87
<211> LENGTH: 44
<212> TYPE: DNA
<213> ORGANISM: Artificial Sequence
<220> FEATURE:
<223> OTHER INFORMATION: S. Agalactiae ddlA Probe SEGP2951
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 87
taatgacaaa ccaaactgtt gatttagaca aaatggttcg tcca                    44

<210> SEQ ID NO 88
<211> LENGTH: 28
<212> TYPE: DNA
<213> ORGANISM: Artificial Sequence
<220> FEATURE:
<223> OTHER INFORMATION: Candida 18s rRNA Forward Primer SEGP1712

<400> SEQUENCE: 88
cgttttcatt aatcaagaac gaaagtta                                      28

<210> SEQ ID NO 89
<211> LENGTH: 20
<212> TYPE: DNA
<213> ORGANISM: Artificial Sequence
<220> FEATURE:
<223> OTHER INFORMATION: Candida 18s rRNA Reverse Primer SEGP1713

<400> SEQUENCE: 89
accgatccct agtcggcata                                               20

<210> SEQ ID NO 90
<211> LENGTH: 33
<212> TYPE: DNA
<213> ORGANISM: Artificial Sequence
<220> FEATURE:
<223> OTHER INFORMATION: Candida 18s rRNA Probe SEGP1716
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
```

-continued

```
<220> FEATURE:
<221> NAME/KEY: misc_feature
<222> LOCATION: (9)..(10)
<223> OTHER INFORMATION: ZEN Quencher

<400> SEQUENCE: 90
agactacgac ggtatctgat catcttcgat ccc                            33

<210> SEQ ID NO 91
<211> LENGTH: 21
<212> TYPE: DNA
<213> ORGANISM: Artificial Sequence
<220> FEATURE:
<223> OTHER INFORMATION: Candida 5.8s rRNA Forward Primer SEGP1718

<400> SEQUENCE: 91
acaacggatc tcttggttct c                                         21

<210> SEQ ID NO 92
<211> LENGTH: 23
<212> TYPE: DNA
<213> ORGANISM: Artificial Sequence
<220> FEATURE:
<223> OTHER INFORMATION: Candida 5.8s rRNA Reverse Primer SEGP1719

<400> SEQUENCE: 92
gcaatgtgcg ttcaaagatt cga                                       23

<210> SEQ ID NO 93
<211> LENGTH: 30
<212> TYPE: DNA
<213> ORGANISM: Artificial Sequence
<220> FEATURE:
<223> OTHER INFORMATION: Candida 5.8s rRNA Probe SEGP1722.1
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Phosphate
<220> FEATURE:
<221> NAME/KEY: misc_feature
<222> LOCATION: (9)..(10)
<223> OTHER INFORMATION: BHQ-2 Quencher

<400> SEQUENCE: 93
tcgatgaaga acgcagcgaa atgcgatacg                                30

<210> SEQ ID NO 94
<211> LENGTH: 19
<212> TYPE: DNA
<213> ORGANISM: Artificial Sequence
<220> FEATURE:
<223> OTHER INFORMATION: Generic Bacteria 16s rRNA Forward Primer
      SEGP1830

<400> SEQUENCE: 94
tcctacggga ggcagcagt                                            19

<210> SEQ ID NO 95
<211> LENGTH: 26
<212> TYPE: DNA
<213> ORGANISM: Artificial Sequence
<220> FEATURE:
<223> OTHER INFORMATION: Generic Bacteria 16s rRNA Reverse Primer
      SEGP1831

<400> SEQUENCE: 95
```
ggactaccag ggtatctaat cctgtt                                             26

<210> SEQ ID NO 96
<211> LENGTH: 23
<212> TYPE: DNA
<213> ORGANISM: Artificial Sequence
<220> FEATURE:
<223> OTHER INFORMATION: Generic Bacteria 16s rRNA Probe SEGP1895.1
<220> FEATURE:
<221> NAME/KEY: misc_feature
<223> OTHER INFORMATION: 5'-CFR 635
<220> FEATURE:
<221> NAME/KEY: misc_feature
<223> OTHER INFORMATION: 3'-Phosphate
<220> FEATURE:
<221> NAME/KEY: misc_feature
<222> LOCATION: (15)..(16)
<223> OTHER INFORMATION: BHQ-2 Quencher

<400> SEQUENCE: 96
cgtattaccg cggctgctgg cac                                                23

<210> SEQ ID NO 97
<211> LENGTH: 25
<212> TYPE: DNA
<213> ORGANISM: Artificial Sequence
<220> FEATURE:
<223> OTHER INFORMATION: Internal Control Forward Primer SEGP1952
<220> FEATURE:
<221> NAME/KEY: modified_base
<222> LOCATION: (25)..(25)
<223> OTHER INFORMATION: t-butylbenzyl-dC

<400> SEQUENCE: 97
acaaccgcgc catacatgtc aagac                                              25

<210> SEQ ID NO 98
<211> LENGTH: 24
<212> TYPE: DNA
<213> ORGANISM: Artificial Sequence
<220> FEATURE:
<223> OTHER INFORMATION: Internal Control Reverse Primer SEGP1953
<220> FEATURE:
<221> NAME/KEY: modified_base
<222> LOCATION: (24)..(24)
<223> OTHER INFORMATION: t-butylbenzyl-dC

<400> SEQUENCE: 98
gtcgggccgc ttatacagta ccac                                               24

<210> SEQ ID NO 99
<211> LENGTH: 33
<212> TYPE: DNA
<213> ORGANISM: Artificial Sequence
<220> FEATURE:
<223> OTHER INFORMATION: Internal Control Probe SEGP1954
<220> FEATURE:
<221> NAME/KEY: misc_feature
<223> OTHER INFORMATION: 5'-Cy5.5
<220> FEATURE:
<221> NAME/KEY: misc_feature
<223> OTHER INFORMATION: 3'-Phosphate
<220> FEATURE:
<221> NAME/KEY: misc_feature
<222> LOCATION: (11)..(2)
<223> OTHER INFORMATION: BHQ-2 Quencher

<400> SEQUENCE: 99
tgcgcgtccc gttttgatac ttcgtaacgg tgc                                     33

```
<210> SEQ ID NO 100
<211> LENGTH: 23
<212> TYPE: DNA
<213> ORGANISM: Artificial Sequence
<220> FEATURE:
<223> OTHER INFORMATION: Streptococcus tuf Forward Primer SEGP1705

<400> SEQUENCE: 100
gtacagttgc ttcaggacgt atc                                             23

<210> SEQ ID NO 101
<211> LENGTH: 21
<212> TYPE: DNA
<213> ORGANISM: Artificial Sequence
<220> FEATURE:
<223> OTHER INFORMATION: Streptococcus tuf Reverse Primer SEGP1706

<400> SEQUENCE: 101
acgttcgatt tcatcacgtt g                                               21

<210> SEQ ID NO 102
<211> LENGTH: 28
<212> TYPE: DNA
<213> ORGANISM: Artificial Sequence
<220> FEATURE:
<223> OTHER INFORMATION: Streptococcus tuf Probe SEGP1709.1
<220> FEATURE:
<221> NAME/KEY: misc_feature
<223> OTHER INFORMATION: 5'-ATTO
<220> FEATURE:
<221> NAME/KEY: misc_feature
<223> OTHER INFORMATION: 3'-Phosphate
<220> FEATURE:
<221> NAME/KEY: misc_feature
<222> LOCATION: (7)..(8)
<223> OTHER INFORMATION: BHQ-2 Quencher

<400> SEQUENCE: 102
ttccgtaaac aacttgacga aggtcttg                                        28

<210> SEQ ID NO 103
<211> LENGTH: 20
<212> TYPE: DNA
<213> ORGANISM: Artificial Sequence
<220> FEATURE:
<223> OTHER INFORMATION: blaKPC Forward Primer SEGP2124

<400> SEQUENCE: 103
gcgataccac gttccgtctg                                                 20

<210> SEQ ID NO 104
<211> LENGTH: 20
<212> TYPE: DNA
<213> ORGANISM: Artificial Sequence
<220> FEATURE:
<223> OTHER INFORMATION: blaVIM Forward Primer SEGP2135

<400> SEQUENCE: 104
ccgagtggtg agtatccgac                                                 20

<210> SEQ ID NO 105
<211> LENGTH: 20
<212> TYPE: DNA
<213> ORGANISM: Artificial Sequence
<220> FEATURE:
<223> OTHER INFORMATION: blaNDM Forward Primer SEGP2127

<400> SEQUENCE: 105
```

-continued tttggcgatc tggttttccg                                            20

<210> SEQ ID NO 106
<211> LENGTH: 20
<212> TYPE: DNA
<213> ORGANISM: Artificial Sequence
<220> FEATURE:
<223> OTHER INFORMATION: blaOXA-48 Forward Primer SEGP2133

<400> SEQUENCE: 106
ggcacgtatg agcaagatgc                                            20

<210> SEQ ID NO 107
<211> LENGTH: 20
<212> TYPE: DNA
<213> ORGANISM: Artificial Sequence
<220> FEATURE:
<223> OTHER INFORMATION: blaKPC Reverse Primer SEGP2125

<400> SEQUENCE: 107
cggtcgtgtt tccctttagc                                            20

<210> SEQ ID NO 108
<211> LENGTH: 21
<212> TYPE: DNA
<213> ORGANISM: Artificial Sequence
<220> FEATURE:
<223> OTHER INFORMATION: blaVIM Reverse Primer SEGP2136

<400> SEQUENCE: 108
gaatgcgtgg gaatctcgtt c                                          21

<210> SEQ ID NO 109
<211> LENGTH: 20
<212> TYPE: DNA
<213> ORGANISM: Artificial Sequence
<220> FEATURE:
<223> OTHER INFORMATION: blaNDM Reverse Primer SEGP2128

<400> SEQUENCE: 109
atcaaaccgt tggaagcgac                                            20

<210> SEQ ID NO 110
<211> LENGTH: 21
<212> TYPE: DNA
<213> ORGANISM: Artificial Sequence
<220> FEATURE:
<223> OTHER INFORMATION: blaOXA-48 Reverse Primer SEGP2134

<400> SEQUENCE: 110
gtttgacaat acgctggctg c                                          21

<210> SEQ ID NO 111
<211> LENGTH: 22
<212> TYPE: DNA
<213> ORGANISM: Artificial Sequence
<220> FEATURE:
<223> OTHER INFORMATION: blaKPC Probe SEGP2126
<220> FEATURE:
<221> NAME/KEY: misc_feature
<223> OTHER INFORMATION: 5'-CFR 635
<220> FEATURE:
<221> NAME/KEY: misc_feature
<223> OTHER INFORMATION: 3'-Phosphate
<220> FEATURE:
<221> NAME/KEY: misc_feature
<222> LOCATION: (14)..(15)
<223> OTHER INFORMATION: BHQ-2 Quencher

<400> SEQUENCE: 111
agcggcagca gtttgttgat tg                                            22

<210> SEQ ID NO 112
<211> LENGTH: 28
<212> TYPE: DNA
<213> ORGANISM: Artificial Sequence
<220> FEATURE:
<223> OTHER INFORMATION: blaVIM Probe SEGP2137
<220> FEATURE:
<221> NAME/KEY: misc_feature
<223> OTHER INFORMATION: 5'-CFR 635
<220> FEATURE:
<221> NAME/KEY: misc_feature
<223> OTHER INFORMATION: 3'-Phosphate
<220> FEATURE:
<221> NAME/KEY: misc_feature
<222> LOCATION: (15)..(16)
<223> OTHER INFORMATION: BHQ-2 Quencher

<400> SEQUENCE: 112
cgctgtatca atcaaaagca actcatca                                      28

<210> SEQ ID NO 113
<211> LENGTH: 21
<212> TYPE: DNA
<213> ORGANISM: Artificial Sequence
<220> FEATURE:
<223> OTHER INFORMATION: blaNDM Probe SEGP2129
<220> FEATURE:
<221> NAME/KEY: misc_feature
<223> OTHER INFORMATION: 5'-CFR 635
<220> FEATURE:
<221> NAME/KEY: misc_feature
<223> OTHER INFORMATION: 3'-Phosphate
<220> FEATURE:
<221> NAME/KEY: misc_feature
<222> LOCATION: (15)..(16)
<223> OTHER INFORMATION: BHQ-2 Quencher

<400> SEQUENCE: 113
agacattcgg tgcgagctgg c                                             21

<210> SEQ ID NO 114
<211> LENGTH: 31
<212> TYPE: DNA
<213> ORGANISM: Artificial Sequence
<220> FEATURE:
<223> OTHER INFORMATION: blaOXA-48 Probe SEGP2346
<220> FEATURE:
<221> NAME/KEY: misc_feature
<223> OTHER INFORMATION: 5'-CFR 635
<220> FEATURE:
<221> NAME/KEY: misc_feature
<223> OTHER INFORMATION: 3'-Phosphate
<220> FEATURE:
<221> NAME/KEY: misc_feature
<222> LOCATION: (11)..(12)
<223> OTHER INFORMATION: BHQ-2 Quencher

<400> SEQUENCE: 114
tcgggcaatg tagacagttt ctggctcgac g                                  31

<210> SEQ ID NO 115
<211> LENGTH: 23
<212> TYPE: DNA
<213> ORGANISM: Artificial Sequence
<220> FEATURE:
<223> OTHER INFORMATION: P. Stuartii citC Forward Primer SEGP2164

-continued

<400> SEQUENCE: 115
gccatcgtga tgaatgccaa tcc                                    23

<210> SEQ ID NO 116
<211> LENGTH: 24
<212> TYPE: DNA
<213> ORGANISM: Artificial Sequence
<220> FEATURE:
<223> OTHER INFORMATION: P. Stuartii citC Reverse Primer SEGP2166

<400> SEQUENCE: 116
tcagagcctt tgtggatagt gaga                                   24

<210> SEQ ID NO 117
<211> LENGTH: 44
<212> TYPE: DNA
<213> ORGANISM: Artificial Sequence
<220> FEATURE:
<223> OTHER INFORMATION: P. Stuartii citC Probe SEGP2167
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 117
ttggctacat ttatttgtcg tcaaagaaga tacctcacgc ttcc              44

<210> SEQ ID NO 118
<211> LENGTH: 24
<212> TYPE: DNA
<213> ORGANISM: Artificial Sequence
<220> FEATURE:
<223> OTHER INFORMATION: Salmonella invA Forward Primer SEGP2119

<400> SEQUENCE: 118
tgaccatttc aatgggaact ctgc                                   24

<210> SEQ ID NO 119
<211> LENGTH: 23
<212> TYPE: DNA
<213> ORGANISM: Artificial Sequence
<220> FEATURE:
<223> OTHER INFORMATION: Salmonella invA Reverse Primer SEGP2121

<400> SEQUENCE: 119
agatcgccaa tcagtcctaa cga                                    23

<210> SEQ ID NO 120
<211> LENGTH: 30
<212> TYPE: DNA
<213> ORGANISM: Artificial Sequence
<220> FEATURE:
<223> OTHER INFORMATION: Salmonella invA Probe SEGP2120
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

```
<400> SEQUENCE: 120
caaaggcgag cagccgctca gtattgagga                                          30

<210> SEQ ID NO 121
<211> LENGTH: 33
<212> TYPE: DNA
<213> ORGANISM: Artificial Sequence
<220> FEATURE:
<223> OTHER INFORMATION: S. Agalactiae gyrB Forward Primer SEGP2921

<400> SEQUENCE: 121
accactgtat ttgattttga taaattagcc aaa                                      33

<210> SEQ ID NO 122
<211> LENGTH: 31
<212> TYPE: DNA
<213> ORGANISM: Artificial Sequence
<220> FEATURE:
<223> OTHER INFORMATION: S. Agalactiae gyrB Reverse Primer SEGP2922

<400> SEQUENCE: 122
ttctcattga taaactcaac gtatgaacct a                                        31

<210> SEQ ID NO 123
<211> LENGTH: 44
<212> TYPE: DNA
<213> ORGANISM: Artificial Sequence
<220> FEATURE:
<223> OTHER INFORMATION: S. Agalactiae gyrB Probe SEGP2923
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 123
actaagaatc tccatttcag acaagcgaga aggtcaagaa gttg                          44

<210> SEQ ID NO 124
<211> LENGTH: 26
<212> TYPE: DNA
<213> ORGANISM: Artificial Sequence
<220> FEATURE:
<223> OTHER INFORMATION: S. Pneumoniae tuf Forward Primer SEGP2777

<400> SEQUENCE: 124
gtgactctaa atacgaagac atcgtt                                              26

<210> SEQ ID NO 125
<211> LENGTH: 22
<212> TYPE: DNA
<213> ORGANISM: Artificial Sequence
<220> FEATURE:
<223> OTHER INFORMATION: S. Pneumoniae tuf Reverse Primer SEGP2778

<400> SEQUENCE: 125
gcaatggttt gtcagtgtca cg                                                  22

<210> SEQ ID NO 126
<211> LENGTH: 26
<212> TYPE: DNA
```

```
<213> ORGANISM: Artificial Sequence
<220> FEATURE:
<223> OTHER INFORMATION: S. Pneumoniae tuf Probe SEGP2779
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 126
tgaacacagt tgatgagtat atccca                                          26

<210> SEQ ID NO 127
<211> LENGTH: 20
<212> TYPE: DNA
<213> ORGANISM: Artificial Sequence
<220> FEATURE:
<223> OTHER INFORMATION: S. Pyogenes speB Forward Primer SEGP2113

<400> SEQUENCE: 127
cggaagaagc cgtcagagac                                                 20

<210> SEQ ID NO 128
<211> LENGTH: 20
<212> TYPE: DNA
<213> ORGANISM: Artificial Sequence
<220> FEATURE:
<223> OTHER INFORMATION: S. Pyogenes speB Reverse Primer SEGP2114

<400> SEQUENCE: 128
atggtgctga cggacgtaac                                                 20

<210> SEQ ID NO 129
<211> LENGTH: 20
<212> TYPE: DNA
<213> ORGANISM: Artificial Sequence
<220> FEATURE:
<223> OTHER INFORMATION: S. Pyogenes speB Probe SEGP2115
<220> FEATURE:
<221> NAME/KEY: misc_feature
<223> OTHER INFORMATION: 5'-FAM
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 129
caccccaacc ccagttaaca                                                 20

<210> SEQ ID NO 130
<211> LENGTH: 18
<212> TYPE: DNA
<213> ORGANISM: Artificial Sequence
<220> FEATURE:
<223> OTHER INFORMATION: P. aeruginosa O-antigen acetylase Forward
      Primer RM_PFP01

<400> SEQUENCE: 130
acgttttccc ttcgctga                                                   18

<210> SEQ ID NO 131
```

```
<211> LENGTH: 18
<212> TYPE: DNA
<213> ORGANISM: Artificial Sequence
<220> FEATURE:
<223> OTHER INFORMATION: P. aeruginosa O-antigen acetylase Reverse
      Primer 1 RM_PRP02

<400> SEQUENCE: 131
gtacagtgac cagccatc                                                      18

<210> SEQ ID NO 132
<211> LENGTH: 19
<212> TYPE: DNA
<213> ORGANISM: Artificial Sequence
<220> FEATURE:
<223> OTHER INFORMATION: P. aeruginosa O-antigen acetylase Reverse
      Primer 2 RM_PRP04

<400> SEQUENCE: 132
gcgaaacaat ccaggccat                                                     19

<210> SEQ ID NO 133
<211> LENGTH: 31
<212> TYPE: DNA
<213> ORGANISM: Artificial Sequence
<220> FEATURE:
<223> OTHER INFORMATION: P. aeruginosa O-antigen acetylase Probe RM_P04
<220> FEATURE:
<221> NAME/KEY: misc_feature
<223> OTHER INFORMATION: 5' FAM_Thr
<220> FEATURE:
<221> NAME/KEY: misc_feature
<223> OTHER INFORMATION: 3' Phosphate
<220> FEATURE:
<221> NAME/KEY: misc_feature
<222> LOCATION: (6)..(7)
<223> OTHER INFORMATION: BHQ-2 Quencher

<400> SEQUENCE: 133
cctacgtgaa tgcgctgttc gatgcgttgg c                                       31

<210> SEQ ID NO 134
<211> LENGTH: 33
<212> TYPE: DNA
<213> ORGANISM: Artificial Sequence
<220> FEATURE:
<223> OTHER INFORMATION: Candida 18s rRNA Probe SEGP1717
<220> FEATURE:
<221> NAME/KEY: misc_feature
<223> OTHER INFORMATION: 5'-HEX
<220> FEATURE:
<221> NAME/KEY: misc_feature
<223> OTHER INFORMATION: 3'-Blocker
<220> FEATURE:
<221> NAME/KEY: misc_feature
<222> LOCATION: (9)..(10)
<223> OTHER INFORMATION: ZEN Quencher

<400> SEQUENCE: 134
agactacgac ggtatctgat catcttcgat ccc                                     33
```